United States Patent
Woolfson et al.

(10) Patent No.: US 8,771,302 B2
(45) Date of Patent: Jul. 8, 2014

(54) METHOD AND APPARATUS FOR RESECTING AND REPLACING AN AORTIC VALVE

(75) Inventors: Steven B. Woolfson, Boston, MA (US); Richard B. Streeter, Winchester, MA (US); Daniel C. Taylor, Brighton, MA (US); William E. Cohn, Chestnut Hill, MA (US)

(73) Assignee: Medtronic, Inc., Minneapolis, MN (US)

( * ) Notice: Subject to any disclaimer, the term of this patent is extended or adjusted under 35 U.S.C. 154(b) by 1273 days.

(21) Appl. No.: 11/784,438

(22) Filed: Apr. 6, 2007

(65) Prior Publication Data

US 2007/0185513 A1 Aug. 9, 2007

Related U.S. Application Data

(60) Division of application No. 10/414,741, filed on Apr. 16, 2003, now Pat. No. 7,201,761, which is a continuation-in-part of application No. 09/896,259, filed on Jun. 29, 2001, now Pat. No. 6,769,434.

(60) Provisional application No. 60/373,042, filed on Apr. 16, 2002, provisional application No. 60/425,891, filed on Nov. 13, 2002.

(51) Int. Cl.
*A61B 17/32* (2006.01)
*A61B 17/14* (2006.01)

(52) U.S. Cl.
USPC .......................................... 606/170; 606/180

(58) Field of Classification Search
USPC ......... 606/167, 170, 171, 174, 180, 184, 185, 606/159; 623/2.11
See application file for complete search history.

(56) References Cited

U.S. PATENT DOCUMENTS

| 3,334,629 A | 8/1967 | Cohn |
| 3,540,431 A | 11/1970 | Mobin-Uddin |

(Continued)

FOREIGN PATENT DOCUMENTS

| CN | 2007-100074433 | 1/2007 |
| DE | 2246526 | 3/1973 |

(Continued)

OTHER PUBLICATIONS

Andersen, H.R. et al. "Transluminal implantation of artificial heart valves. Description of a new expandable aortic valve and initial results with implantation by catheter technique in closed chest pigs." Euro. Heart J. (1992) 13:704-708.

(Continued)

*Primary Examiner* — Tuan V Nguyen

(57) ABSTRACT

Apparatus for resecting a diseased heart valve, the apparatus including: a body portion; a first handle and a second handle; a cutting blade; a set of retaining arms; a pass-off tool having a first attachment device configured to selectively engage the first handle attached to the body portion so as to allow placement of the second handle of the body portion adjacent to the diseased heart valve, and a controller tool, having a second attachment device at the distal end thereof, the second attachment device configured to selectively engage the second handle attached to the body portion so as to allow positioning of the body portion adjacent to the diseased heart valve, a cutting blade actuator configured to cause the cutting blade to selectively rotate, and a retaining arm actuator configured to selectively position the set of retaining arms from the contracted state to the expanded state.

16 Claims, 51 Drawing Sheets

(56) References Cited

U.S. PATENT DOCUMENTS

| | | | |
|---|---|---|---|
| 3,548,417 A | 12/1970 | Kisher | |
| 3,628,535 A | 12/1971 | Ostrowsky et al. | |
| 3,642,004 A | 2/1972 | Osthagen et al. | |
| 3,671,979 A | 6/1972 | Moulopoulos | |
| 3,755,823 A | 9/1973 | Hancock | |
| 3,795,246 A | 3/1974 | Sturgeon | |
| 3,839,741 A | 10/1974 | Haller | |
| 3,868,956 A | 3/1975 | Alfidi et al. | |
| 3,874,388 A | 4/1975 | King et al. | |
| 4,233,690 A | 11/1980 | Akins | |
| 4,291,420 A | 9/1981 | Reul | |
| 4,373,216 A | 2/1983 | Klawitter | |
| 4,406,022 A | 9/1983 | Roy | |
| 4,425,908 A | 1/1984 | Simon | |
| 4,501,030 A | 2/1985 | Lane | |
| 4,535,483 A | 8/1985 | Klawitter et al. | |
| 4,580,568 A | 4/1986 | Gianturco | |
| 4,586,923 A | 5/1986 | Gould et al. | |
| 4,605,407 A | 8/1986 | Black et al. | |
| 4,610,688 A | 9/1986 | Silvestrini et al. | |
| 4,612,011 A | 9/1986 | Kautzky | |
| 4,643,732 A | 2/1987 | Pietsch et al. | |
| 4,647,283 A | 3/1987 | Carpentier et al. | |
| 4,648,881 A | 3/1987 | Carpentier et al. | |
| 4,662,885 A | 5/1987 | DiPisa, Jr. | |
| 4,665,906 A | 5/1987 | Jervis | |
| 4,681,908 A | 7/1987 | Broderick et al. | |
| 4,692,164 A | 9/1987 | Dzemeshkevich et al. | |
| 4,710,192 A | 12/1987 | Liotta et al. | |
| 4,762,128 A | 8/1988 | Rosenbluth | |
| 4,819,751 A | 4/1989 | Shimada et al. | |
| 4,829,990 A | 5/1989 | Thuroff et al. | |
| 4,834,755 A | 5/1989 | Silvestrini et al. | |
| 4,872,874 A | 10/1989 | Taheri | |
| 4,909,252 A | 3/1990 | Goldberger | |
| 4,917,102 A | 4/1990 | Miller et al. | |
| 4,954,126 A | 9/1990 | Wallsten | |
| 5,002,559 A | 3/1991 | Tower | |
| 5,041,130 A | 8/1991 | Cosgrove et al. | |
| 5,059,203 A * | 10/1991 | Husted | 606/159 |
| 5,061,273 A | 10/1991 | Yock | |
| 5,069,679 A | 12/1991 | Taheri | |
| 5,071,424 A * | 12/1991 | Reger | 606/159 |
| 5,074,871 A * | 12/1991 | Groshong | 606/170 |
| 5,080,668 A | 1/1992 | Bolz et al. | |
| 5,100,425 A * | 3/1992 | Fischell et al. | 606/159 |
| 5,161,547 A | 11/1992 | Tower | |
| 5,192,297 A | 3/1993 | Hull | |
| 5,217,483 A | 6/1993 | Tower | |
| 5,232,445 A | 8/1993 | Bonzel | |
| 5,266,073 A | 11/1993 | Wall | |
| 5,272,909 A | 12/1993 | Nguyen et al. | |
| 5,282,847 A | 2/1994 | Trescony et al. | |
| 5,327,774 A | 7/1994 | Nguyen et al. | |
| 5,350,398 A | 9/1994 | Pavcnik et al. | |
| 5,360,444 A | 11/1994 | Kusuhara | |
| 5,389,106 A | 2/1995 | Tower | |
| 5,411,055 A | 5/1995 | Kane et al. | |
| 5,415,633 A | 5/1995 | Lazarus et al. | |
| 5,415,656 A * | 5/1995 | Tihon et al. | 606/46 |
| 5,415,664 A | 5/1995 | Pinchuk | |
| 5,431,676 A | 7/1995 | Dubrul et al. | |
| 5,449,384 A | 9/1995 | Johnson | |
| 5,476,510 A | 12/1995 | Eberhardt et al. | |
| 5,489,294 A | 2/1996 | McVenes et al. | |
| 5,489,297 A | 2/1996 | Duran | |
| 5,496,346 A | 3/1996 | Horzewski et al. | |
| 5,507,767 A | 4/1996 | Maeda et al. | |
| 5,545,209 A | 8/1996 | Roberts et al. | |
| 5,545,211 A | 8/1996 | An et al. | |
| 5,549,665 A | 8/1996 | Vesely | |
| 5,571,175 A | 11/1996 | Vanney et al. | |
| 5,575,818 A | 11/1996 | Pinchuk | |
| 5,580,922 A | 12/1996 | Park et al. | |
| 5,591,185 A | 1/1997 | Kilmer et al. | |
| 5,591,187 A | 1/1997 | Dekel | |
| 5,591,195 A | 1/1997 | Taheri et al. | |
| 5,599,305 A | 2/1997 | Hermann et al. | |
| 5,607,464 A | 3/1997 | Trescony et al. | |
| 5,616,149 A * | 4/1997 | Barath | 606/159 |
| 5,639,274 A | 6/1997 | Fischell et al. | |
| 5,645,559 A | 7/1997 | Hachtman et al. | |
| 5,665,098 A | 9/1997 | Kelly et al. | |
| 5,667,523 A | 9/1997 | Bynon et al. | |
| 5,674,277 A | 10/1997 | Freitag | |
| 5,690,662 A | 11/1997 | Chiu et al. | |
| 5,695,498 A | 12/1997 | Tower | |
| 5,702,368 A | 12/1997 | Stevens et al. | |
| 5,713,953 A | 2/1998 | Vallana et al. | |
| 5,716,370 A | 2/1998 | Williamson, IV et al. | |
| 5,728,068 A | 3/1998 | Leone et al. | |
| 5,746,709 A | 5/1998 | Rom et al. | |
| 5,756,476 A | 5/1998 | Epstein | |
| 5,766,151 A | 6/1998 | Valley et al. | |
| 5,769,812 A | 6/1998 | Stevens et al. | |
| 5,782,809 A | 7/1998 | Umeno et al. | |
| 5,800,456 A | 9/1998 | Maeda et al. | |
| 5,817,126 A | 10/1998 | Imran | |
| 5,824,041 A | 10/1998 | Lenker | |
| 5,824,043 A | 10/1998 | Cottone, Jr. | |
| 5,824,053 A | 10/1998 | Khosravi et al. | |
| 5,824,056 A | 10/1998 | Rosenberg | |
| 5,824,061 A | 10/1998 | Quijano et al. | |
| 5,824,064 A | 10/1998 | Taheri | |
| 5,827,237 A | 10/1998 | Macoviak et al. | |
| 5,827,324 A | 10/1998 | Cassell et al. | |
| 5,843,121 A | 12/1998 | Yoon | |
| 5,843,158 A | 12/1998 | Lenker et al. | |
| 5,851,232 A | 12/1998 | Lois | |
| 5,855,601 A | 1/1999 | Bessler et al. | |
| 5,855,602 A | 1/1999 | Angell | |
| 5,861,028 A | 1/1999 | Angell | |
| 5,868,768 A | 2/1999 | Wicherski et al. | |
| 5,876,367 A | 3/1999 | Kaganov et al. | |
| 5,876,448 A | 3/1999 | Thompson et al. | |
| 5,888,201 A | 3/1999 | Stinson et al. | |
| 5,891,191 A | 4/1999 | Stinson | |
| 5,906,619 A | 5/1999 | Olson et al. | |
| 5,907,893 A | 6/1999 | Zadno-Azizi et al. | |
| 5,913,842 A | 6/1999 | Boyd et al. | |
| 5,916,193 A | 6/1999 | Stevens et al. | |
| 5,944,738 A | 8/1999 | Amplatz et al. | |
| 5,968,068 A | 10/1999 | Dehdashtian et al. | |
| 5,972,030 A | 10/1999 | Garrison et al. | |
| 5,980,570 A | 11/1999 | Simpson | |
| 5,984,957 A | 11/1999 | Laptewicz, Jr. et al. | |
| 5,984,959 A | 11/1999 | Robertson et al. | |
| 5,997,573 A | 12/1999 | Quijano et al. | |
| 6,010,531 A | 1/2000 | Donlon et al. | |
| 6,019,790 A | 2/2000 | Holmberg et al. | |
| 6,022,370 A | 2/2000 | Tower | |
| 6,029,671 A | 2/2000 | Stevens et al. | |
| 6,033,419 A | 3/2000 | Hamblin et al. | |
| 6,042,589 A | 3/2000 | Marianne | |
| 6,042,598 A | 3/2000 | Tsugita et al. | |
| 6,042,607 A | 3/2000 | Williamson, IV | |
| 6,051,014 A | 4/2000 | Jang | |
| 6,059,809 A | 5/2000 | Amor et al. | |
| 6,080,173 A | 6/2000 | Williamson, IV et al. | |
| 6,110,201 A | 8/2000 | Quijano et al. | |
| 6,132,473 A | 10/2000 | Williams et al. | |
| 6,139,572 A | 10/2000 | Campbell et al. | |
| 6,146,366 A | 11/2000 | Schachar | |
| 6,159,239 A | 12/2000 | Greenhalgh | |
| 6,162,208 A | 12/2000 | Hipps | |
| 6,162,245 A | 12/2000 | Jayaraman | |
| 6,174,327 B1 | 1/2001 | Mertens et al. | |
| 6,200,322 B1 | 3/2001 | Branch et al. | |
| 6,200,336 B1 | 3/2001 | Pavcnik et al. | |
| 6,203,550 B1 | 3/2001 | Olson | |
| 6,217,585 B1 | 4/2001 | Houser et al. | |
| 6,218,662 B1 | 4/2001 | Tchakarov et al. | |
| 6,221,006 B1 | 4/2001 | Dubrul et al. | |
| 6,235,045 B1 | 5/2001 | Barbut et al. | |

(56) References Cited

U.S. PATENT DOCUMENTS

| | | |
|---|---|---|
| 6,241,757 B1 | 6/2001 | An et al. |
| 6,248,116 B1 | 6/2001 | Chevilon |
| 6,258,114 B1 | 7/2001 | Konya et al. |
| 6,258,115 B1 | 7/2001 | Dubrul |
| 6,258,120 B1 | 7/2001 | McKenzie et al. |
| 6,277,555 B1 | 8/2001 | Duran et al. |
| 6,287,291 B1* | 9/2001 | Bigus et al. .................. 604/523 |
| 6,309,382 B1 | 10/2001 | Garrison et al. |
| 6,309,399 B1 | 10/2001 | Barbut et al. |
| 6,309,417 B1 | 10/2001 | Spence et al. |
| 6,334,869 B1 | 1/2002 | Leonhardt et al. |
| 6,338,735 B1 | 1/2002 | Stevens |
| 6,348,063 B1 | 2/2002 | Yassour et al. |
| 6,352,708 B1 | 3/2002 | Duran et al. |
| 6,371,970 B1 | 4/2002 | Khosravi et al. |
| 6,371,983 B1 | 4/2002 | Lane |
| 6,379,383 B1 | 4/2002 | Palmaz et al. |
| 6,380,457 B1 | 4/2002 | Yurek et al. |
| 6,383,171 B1 | 5/2002 | Gifford et al. |
| 6,395,014 B1 | 5/2002 | Macoviak et al. |
| 6,398,807 B1 | 6/2002 | Chouinard et al. |
| 6,409,750 B1 | 6/2002 | Hyodoh et al. |
| 6,464,707 B1 | 10/2002 | Bjerken |
| 6,468,303 B1 | 10/2002 | Amplatz et al. |
| 6,468,660 B2 | 10/2002 | Ogle |
| 6,475,239 B1 | 11/2002 | Campbell et al. |
| 6,494,909 B2 | 12/2002 | Greenhalgh |
| 6,497,711 B1* | 12/2002 | Plaia et al. .................. 606/159 |
| 6,503,272 B2 | 1/2003 | Duerig et al. |
| 6,508,833 B2 | 1/2003 | Pavcnik et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,562,031 B2 | 5/2003 | Chandrasekaran et al. |
| 6,562,058 B2 | 5/2003 | Seguin et al. |
| 6,585,758 B1 | 7/2003 | Chouinard et al. |
| 6,592,546 B1 | 7/2003 | Barbut et al. |
| 6,613,077 B2 | 9/2003 | Gilligan et al. |
| 6,622,604 B1 | 9/2003 | Chouinard et al. |
| 6,626,903 B2* | 9/2003 | McGuckin et al. .............. 606/45 |
| 6,635,068 B1 | 10/2003 | Dubrul et al. |
| 6,652,571 B1 | 11/2003 | White et al. |
| 6,652,578 B2 | 11/2003 | Bailey et al. |
| 6,656,213 B2 | 12/2003 | Solem |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,698 B2 | 1/2004 | McGuckin, Jr. et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,692,513 B2 | 2/2004 | Streeter et al. |
| 6,695,878 B2 | 2/2004 | McGuckin, Jr. et al. |
| 6,702,851 B1 | 3/2004 | Chinn et al. |
| 6,719,789 B2 | 4/2004 | Cox |
| 6,730,377 B2 | 5/2004 | Wang |
| 6,736,846 B2 | 5/2004 | Cox |
| 6,752,828 B2 | 6/2004 | Thornton |
| 6,758,855 B2 | 7/2004 | Fulton, III et al. |
| 6,769,434 B2 | 8/2004 | Liddicoat et al. |
| 6,786,925 B1 | 9/2004 | Schoon |
| 6,790,229 B1 | 9/2004 | Berreklouw |
| 6,792,979 B2 | 9/2004 | Konya et al. |
| 6,797,002 B2 | 9/2004 | Spence |
| 6,821,297 B2 | 11/2004 | Snyders |
| 6,830,575 B2 | 12/2004 | Stenzel et al. |
| 6,830,585 B1 | 12/2004 | Artof |
| 6,846,325 B2 | 1/2005 | Liddicoat |
| 6,866,650 B2 | 3/2005 | Stevens |
| 6,872,223 B2 | 3/2005 | Roberts |
| 6,875,231 B2 | 4/2005 | Anduiza et al. |
| 6,883,522 B2 | 4/2005 | Spence et al. |
| 6,887,266 B2 | 5/2005 | Williams et al. |
| 6,890,330 B2 | 5/2005 | Streeter et al. |
| 6,896,690 B1 | 5/2005 | Lambrecht et al. |
| 6,913,600 B2 | 7/2005 | Valley et al. |
| 6,929,653 B2 | 8/2005 | Streeter |
| 6,936,066 B2 | 8/2005 | Palmaz et al. |
| 6,939,365 B1 | 9/2005 | Fogarty et al. |
| 6,951,571 B1 | 10/2005 | Srivastava |
| 6,974,474 B2 | 12/2005 | Pavcnik et al. |
| 6,974,476 B2 | 12/2005 | McGuckin et al. |
| 6,986,742 B2 | 1/2006 | Hart et al. |
| 6,989,027 B2 | 1/2006 | Allen et al. |
| 6,989,028 B2 | 1/2006 | Lashinski et al. |
| 6,991,649 B2 | 1/2006 | Sievers |
| 7,018,401 B1 | 3/2006 | Hyodoh et al. |
| 7,041,128 B2 | 5/2006 | McGuckin, Jr. et al. |
| 7,044,966 B2 | 5/2006 | Svanidze et al. |
| 7,048,014 B2 | 5/2006 | Hyodoh et al. |
| 7,097,659 B2 | 8/2006 | Woolfson et al. |
| 7,101,396 B2 | 9/2006 | Artof et al. |
| 7,105,016 B2 | 9/2006 | Shiu et al. |
| 7,115,141 B2 | 10/2006 | Menz et al. |
| 7,128,759 B2 | 10/2006 | Osborne et al. |
| 7,147,663 B1 | 12/2006 | Berg et al. |
| 7,153,324 B2 | 12/2006 | Case et al. |
| 7,160,319 B2 | 1/2007 | Chouinard et al. |
| 7,175,656 B2 | 2/2007 | Khairkhahan |
| 7,186,265 B2 | 3/2007 | Sharkawy et al. |
| 7,195,641 B2 | 3/2007 | Palmaz et al. |
| 7,198,646 B2 | 4/2007 | Figulla et al. |
| 7,201,761 B2 | 4/2007 | Woolfson et al. |
| 7,201,772 B2 | 4/2007 | Schwammenthal et al. |
| 7,252,682 B2 | 8/2007 | Seguin |
| 7,300,457 B2 | 11/2007 | Palmaz |
| 7,300,463 B2 | 11/2007 | Liddicoat |
| 7,316,706 B2 | 1/2008 | Bloom et al. |
| 7,329,278 B2 | 2/2008 | Seguin |
| 7,335,218 B2 | 2/2008 | Wilson et al. |
| 7,338,520 B2 | 3/2008 | Bailey et al. |
| 7,377,938 B2 | 5/2008 | Sarac et al. |
| 7,381,218 B2 | 6/2008 | Schreck |
| 7,384,411 B1 | 6/2008 | Condado |
| 7,442,204 B2 | 10/2008 | Schwammenthal et al. |
| 7,470,284 B2 | 12/2008 | Lambrecht et al. |
| 7,481,838 B2 | 1/2009 | Carpentier et al. |
| 7,544,206 B2 | 6/2009 | Cohn et al. |
| 7,547,322 B2 | 6/2009 | Sarac et al. |
| 7,556,646 B2 | 7/2009 | Yang et al. |
| 7,780,723 B2 | 8/2010 | Taylor |
| 2001/0001314 A1 | 5/2001 | Davison et al. |
| 2001/0002445 A1 | 5/2001 | Vesely |
| 2001/0007956 A1 | 7/2001 | Letac et al. |
| 2001/0010017 A1 | 7/2001 | Letac et al. |
| 2001/0011189 A1 | 8/2001 | Drasler et al. |
| 2001/0021872 A1 | 9/2001 | Bailey et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0044647 A1 | 11/2001 | Pinchuk et al. |
| 2002/0010508 A1 | 1/2002 | Chobotov |
| 2002/0029014 A1 | 3/2002 | Jayaraman |
| 2002/0032480 A1 | 3/2002 | Spence et al. |
| 2002/0032481 A1 | 3/2002 | Gabbay |
| 2002/0035396 A1 | 3/2002 | Heath |
| 2002/0042650 A1 | 4/2002 | Vardi et al. |
| 2002/0052651 A1 | 5/2002 | Myers et al. |
| 2002/0058995 A1 | 5/2002 | Stevens |
| 2002/0072789 A1 | 6/2002 | Hackett et al. |
| 2002/0095209 A1 | 7/2002 | Zadno-Azizi et al. |
| 2002/0099439 A1 | 7/2002 | Schwartz et al. |
| 2002/0103533 A1 | 8/2002 | Langberg et al. |
| 2002/0107565 A1 | 8/2002 | Greenhalgh |
| 2002/0111674 A1 | 8/2002 | Chouinard et al. |
| 2002/0123802 A1 | 9/2002 | Snyders |
| 2002/0133183 A1 | 9/2002 | Lentz et al. |
| 2002/0138138 A1 | 9/2002 | Yang |
| 2002/0151970 A1 | 10/2002 | Garrison et al. |

(56) References Cited

U.S. PATENT DOCUMENTS

| | | |
|---|---|---|
| 2002/0161392 A1 | 10/2002 | Dubrul |
| 2002/0161394 A1 | 10/2002 | Macoviak et al. |
| 2002/0173842 A1 | 11/2002 | Buchanan |
| 2002/0193871 A1 | 12/2002 | Beyersdorf et al. |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0040771 A1 | 2/2003 | Hyodoh et al. |
| 2003/0040772 A1 | 2/2003 | Hyodoh et al. |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0069492 A1 | 4/2003 | Abrams et al. |
| 2003/0100939 A1 | 5/2003 | Yodfat et al. |
| 2003/0109924 A1 | 6/2003 | Cribier |
| 2003/0125795 A1 | 7/2003 | Pavcnik et al. |
| 2003/0130726 A1 | 7/2003 | Thorpe et al. |
| 2003/0130729 A1 | 7/2003 | Paniagua et al. |
| 2003/0139804 A1 | 7/2003 | Hankh et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0181850 A1 | 9/2003 | Diamond et al. |
| 2003/0191519 A1 | 10/2003 | Lombardi et al. |
| 2003/0199913 A1 | 10/2003 | Dubrul et al. |
| 2003/0199963 A1 | 10/2003 | Tower et al. |
| 2003/0199971 A1 | 10/2003 | Tower et al. |
| 2003/0212410 A1 | 11/2003 | Stenzel et al. |
| 2003/0225445 A1 | 12/2003 | Derus et al. |
| 2004/0019374 A1 | 1/2004 | Hojeibane et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049262 A1 | 3/2004 | Obermiller et al. |
| 2004/0049266 A1 | 3/2004 | Anduiza et al. |
| 2004/0082904 A1 | 4/2004 | Houde et al. |
| 2004/0088045 A1 | 5/2004 | Cox |
| 2004/0092858 A1 | 5/2004 | Wilson et al. |
| 2004/0092989 A1 | 5/2004 | Wilson et al. |
| 2004/0093005 A1 | 5/2004 | Durcan |
| 2004/0093060 A1 | 5/2004 | Seguin et al. |
| 2004/0093075 A1 | 5/2004 | Kuehne |
| 2004/0097788 A1 | 5/2004 | Mourles et al. |
| 2004/0098112 A1 | 5/2004 | DiMatteo et al. |
| 2004/0106976 A1 | 6/2004 | Bailey et al. |
| 2004/0106990 A1 | 6/2004 | Spence et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0122514 A1 | 6/2004 | Fogarty et al. |
| 2004/0122516 A1 | 6/2004 | Fogarty |
| 2004/0127979 A1 | 7/2004 | Wilson |
| 2004/0138742 A1 | 7/2004 | Myers et al. |
| 2004/0138743 A1 | 7/2004 | Myers et al. |
| 2004/0153146 A1 | 8/2004 | Lashinski et al. |
| 2004/0167573 A1 | 8/2004 | Williamson |
| 2004/0167620 A1 | 8/2004 | Ortiz |
| 2004/0186563 A1 | 9/2004 | Iobbi |
| 2004/0193261 A1 | 9/2004 | Berreklouw |
| 2004/0210240 A1 | 10/2004 | Saint |
| 2004/0210304 A1 | 10/2004 | Seguin et al. |
| 2004/0210307 A1 | 10/2004 | Khairkhahan |
| 2004/0215333 A1 | 10/2004 | Duran |
| 2004/0215339 A1 | 10/2004 | Drasler et al. |
| 2004/0225353 A1 | 11/2004 | McGuckin, Jr. |
| 2004/0225354 A1 | 11/2004 | Allen |
| 2004/0254636 A1 | 12/2004 | Flagle et al. |
| 2004/0260322 A1 | 12/2004 | Rudko et al. |
| 2004/0260394 A1 | 12/2004 | Douk et al. |
| 2004/0267357 A1 | 12/2004 | Allen et al. |
| 2005/0010246 A1 | 1/2005 | Streeter |
| 2005/0010285 A1 | 1/2005 | Lambrecht et al. |
| 2005/0010287 A1 | 1/2005 | Macoviak |
| 2005/0015112 A1 | 1/2005 | Cohn et al. |
| 2005/0027348 A1 | 2/2005 | Case et al. |
| 2005/0033398 A1 | 2/2005 | Seguin |
| 2005/0043790 A1 | 2/2005 | Seguin |
| 2005/0049692 A1 | 3/2005 | Numamoto |
| 2005/0049696 A1 | 3/2005 | Siess |
| 2005/0055088 A1 | 3/2005 | Liddicoat et al. |
| 2005/0060029 A1 | 3/2005 | Le |
| 2005/0060030 A1 | 3/2005 | Lashinski et al. |
| 2005/0075584 A1 | 4/2005 | Cali |
| 2005/0075659 A1 | 4/2005 | Realyvasquez et al. |
| 2005/0075712 A1 | 4/2005 | Biancucci |
| 2005/0075717 A1 | 4/2005 | Nguyen |
| 2005/0075719 A1 | 4/2005 | Bergheim |
| 2005/0075724 A1 | 4/2005 | Svanidze |
| 2005/0075727 A1 | 4/2005 | Wheatley |
| 2005/0075730 A1 | 4/2005 | Myers |
| 2005/0075731 A1 | 4/2005 | Artof |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0085900 A1 | 4/2005 | Case et al. |
| 2005/0096568 A1 | 5/2005 | Kato |
| 2005/0096692 A1 | 5/2005 | Linder et al. |
| 2005/0096724 A1 | 5/2005 | Stenzel et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0107871 A1 | 5/2005 | Realyvasquez et al. |
| 2005/0113910 A1 | 5/2005 | Paniagua |
| 2005/0119688 A1 | 6/2005 | Berheim |
| 2005/0131438 A1 | 6/2005 | Cohn |
| 2005/0137686 A1 | 6/2005 | Salahieh |
| 2005/0137688 A1 | 6/2005 | Salahieh et al. |
| 2005/0137692 A1 | 6/2005 | Haug |
| 2005/0137695 A1 | 6/2005 | Salahieh |
| 2005/0137701 A1 | 6/2005 | Salahieh |
| 2005/0143807 A1 | 6/2005 | Pavcnik et al. |
| 2005/0143809 A1 | 6/2005 | Salahieh |
| 2005/0148997 A1 | 7/2005 | Valley et al. |
| 2005/0149181 A1 | 7/2005 | Eberhardt |
| 2005/0165477 A1 | 7/2005 | Anduiza et al. |
| 2005/0187616 A1 | 8/2005 | Realyvasquez |
| 2005/0197695 A1 | 9/2005 | Stacchino et al. |
| 2005/0203549 A1 | 9/2005 | Realyvasquez |
| 2005/0203605 A1 | 9/2005 | Dolan |
| 2005/0203618 A1 | 9/2005 | Sharkawy |
| 2005/0222674 A1 | 10/2005 | Paine |
| 2005/0228495 A1 | 10/2005 | Macoviak |
| 2005/0240263 A1 | 10/2005 | Fogarty et al. |
| 2005/0261759 A1 | 11/2005 | Lambrecht et al. |
| 2005/0283962 A1 | 12/2005 | Boudjemline |
| 2006/0004439 A1 | 1/2006 | Spenser et al. |
| 2006/0004469 A1 | 1/2006 | Sokel |
| 2006/0009841 A1 | 1/2006 | McGuckin et al. |
| 2006/0052867 A1 | 3/2006 | Revuelta et al. |
| 2006/0058775 A1 | 3/2006 | Stevens et al. |
| 2006/0089711 A1 | 4/2006 | Dolan |
| 2006/0100685 A1 | 5/2006 | Seguin et al. |
| 2006/0116757 A1 | 6/2006 | Lashinski et al. |
| 2006/0135964 A1 | 6/2006 | Vesely |
| 2006/0142848 A1 | 6/2006 | Gabbay |
| 2006/0149350 A1 | 7/2006 | Patel et al. |
| 2006/0167474 A1 | 7/2006 | Bloom et al. |
| 2006/0178740 A1 | 8/2006 | Stacchino et al. |
| 2006/0195134 A1 | 8/2006 | Crittenden |
| 2006/0206192 A1 | 9/2006 | Tower et al. |
| 2006/0206202 A1 | 9/2006 | Bonhoefer et al. |
| 2006/0212111 A1 | 9/2006 | Case et al. |
| 2006/0247763 A1 | 11/2006 | Slater |
| 2006/0259134 A1 | 11/2006 | Schwammenthal et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |

(56) References Cited

U.S. PATENT DOCUMENTS

| | | |
|---|---|---|
| 2006/0271166 A1 | 11/2006 | Thill et al. |
| 2006/0271175 A1 | 11/2006 | Woolfson et al. |
| 2006/0276874 A1 | 12/2006 | Wilson et al. |
| 2006/0276882 A1 | 12/2006 | Case et al. |
| 2006/0282161 A1 | 12/2006 | Huynh et al. |
| 2007/0005129 A1 | 1/2007 | Damm et al. |
| 2007/0005131 A1 | 1/2007 | Taylor |
| 2007/0010878 A1 | 1/2007 | Rafiee et al. |
| 2007/0016286 A1 | 1/2007 | Herrmann et al. |
| 2007/0027518 A1 | 2/2007 | Case et al. |
| 2007/0027533 A1 | 2/2007 | Douk |
| 2007/0038295 A1 | 2/2007 | Case et al. |
| 2007/0043431 A1 | 2/2007 | Melsheimer |
| 2007/0043435 A1 | 2/2007 | Seguin et al. |
| 2007/0051377 A1 | 3/2007 | Douk et al. |
| 2007/0073392 A1 | 3/2007 | Heyninck-Jantz |
| 2007/0078509 A1 | 4/2007 | Lotfy et al. |
| 2007/0078510 A1 | 4/2007 | Ryan |
| 2007/0088431 A1 | 4/2007 | Bourang et al. |
| 2007/0093869 A1 | 4/2007 | Bloom et al. |
| 2007/0100439 A1 | 5/2007 | Cangialosi |
| 2007/0100440 A1 | 5/2007 | Figulla |
| 2007/0100449 A1 | 5/2007 | O'Neil et al. |
| 2007/0112415 A1 | 5/2007 | Bartlett |
| 2007/0162102 A1 | 7/2007 | Ryan et al. |
| 2007/0162113 A1 | 7/2007 | Sharkawy et al. |
| 2007/0185513 A1 | 8/2007 | Woolfson et al. |
| 2007/0203391 A1 | 8/2007 | Bloom et al. |
| 2007/0225681 A1 | 9/2007 | House |
| 2007/0232898 A1 | 10/2007 | Huynh et al. |
| 2007/0233228 A1 | 10/2007 | Eberhardt et al. |
| 2007/0233237 A1 | 10/2007 | Krivoruchko |
| 2007/0233238 A1 | 10/2007 | Huynh et al. |
| 2007/0238979 A1 | 10/2007 | Huynh et al. |
| 2007/0239254 A1 | 10/2007 | Marchand et al. |
| 2007/0239265 A1 | 10/2007 | Birdsall |
| 2007/0239266 A1 | 10/2007 | Birdsall |
| 2007/0239269 A1 | 10/2007 | Dolan et al. |
| 2007/0239273 A1 | 10/2007 | Allen |
| 2007/0244544 A1 | 10/2007 | Birdsall et al. |
| 2007/0244545 A1 | 10/2007 | Birdsall et al. |
| 2007/0244546 A1 | 10/2007 | Francis |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255394 A1 | 11/2007 | Ryan |
| 2007/0255396 A1 | 11/2007 | Douk et al. |
| 2007/0288000 A1 | 12/2007 | Bonan |
| 2008/0004696 A1 | 1/2008 | Vesely |
| 2008/0009940 A1 | 1/2008 | Cribier |
| 2008/0015671 A1 | 1/2008 | Bonhoeffer |
| 2008/0021552 A1 | 1/2008 | Gabbay |
| 2008/0048656 A1 | 2/2008 | Tan |
| 2008/0065011 A1 | 3/2008 | Marchand et al. |
| 2008/0065206 A1 | 3/2008 | Liddicoat |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0077234 A1 | 3/2008 | Styrc |
| 2008/0082165 A1 | 4/2008 | Wilson et al. |
| 2008/0082166 A1 | 4/2008 | Styrc et al. |
| 2008/0125861 A1 | 5/2008 | Webler et al. |
| 2008/0133003 A1 | 6/2008 | Seguin et al. |
| 2008/0140189 A1 | 6/2008 | Nguyen et al. |
| 2008/0147105 A1 | 6/2008 | Wilson et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0154355 A1 | 6/2008 | Benichow et al. |
| 2008/0154356 A1 | 6/2008 | Obermiller et al. |
| 2008/0161910 A1 | 7/2008 | Revuelta et al. |
| 2008/0161911 A1 | 7/2008 | Revuelta et al. |
| 2008/0183273 A1 | 7/2008 | Mesana et al. |
| 2008/0188928 A1 | 8/2008 | Salahieh et al. |
| 2008/0215143 A1 | 9/2008 | Seguin et al. |
| 2008/0215144 A1 | 9/2008 | Ryan et al. |
| 2008/0228254 A1 | 9/2008 | Ryan |
| 2008/0228263 A1 | 9/2008 | Ryan |
| 2008/0234797 A1 | 9/2008 | Styrc |
| 2008/0243246 A1 | 10/2008 | Ryan et al. |
| 2008/0255651 A1 | 10/2008 | Dwork |
| 2008/0255660 A1 | 10/2008 | Guyenot et al. |
| 2008/0255661 A1 | 10/2008 | Straubinger et al. |
| 2008/0262593 A1 | 10/2008 | Ryan et al. |
| 2008/0269878 A1 | 10/2008 | Iobbi |
| 2009/0005863 A1 | 1/2009 | Goetz et al. |
| 2009/0012600 A1 | 1/2009 | Styrc et al. |
| 2009/0048656 A1 | 2/2009 | Wen |
| 2009/0054976 A1 | 2/2009 | Tuval et al. |
| 2009/0069886 A1 | 3/2009 | Suri et al. |
| 2009/0069887 A1 | 3/2009 | Righini et al. |
| 2009/0069889 A1 | 3/2009 | Suri et al. |
| 2009/0085900 A1 | 4/2009 | Weiner |
| 2009/0099653 A1 | 4/2009 | Suri et al. |
| 2009/0138079 A1 | 5/2009 | Tuval et al. |
| 2009/0164004 A1 | 6/2009 | Cohn |
| 2009/0171447 A1 | 7/2009 | VonSegesser et al. |
| 2009/0192585 A1 | 7/2009 | Bloom et al. |
| 2009/0192586 A1 | 7/2009 | Tabor et al. |
| 2009/0192591 A1 | 7/2009 | Ryan et al. |
| 2009/0198316 A1 | 8/2009 | Laske et al. |
| 2009/0216310 A1 | 8/2009 | Straubinger et al. |
| 2009/0216312 A1 | 8/2009 | Straubinger et al. |
| 2009/0216313 A1 | 8/2009 | Straubinger et al. |
| 2009/0234443 A1 | 9/2009 | Ottma et al. |
| 2009/0240264 A1 | 9/2009 | Tuval et al. |
| 2009/0240320 A1 | 9/2009 | Tuval |
| 2009/0287296 A1 | 11/2009 | Manasse |
| 2010/0036479 A1 | 2/2010 | Hill et al. |
| 2010/0094411 A1 | 4/2010 | Tuval et al. |
| 2010/0100167 A1 | 4/2010 | Bortlein et al. |
| 2010/0131054 A1 | 5/2010 | Tuval et al. |
| 2010/0137979 A1 | 6/2010 | Tuval et al. |
| 2010/0161045 A1 | 6/2010 | Righini |
| 2010/0234940 A1 | 9/2010 | Dolan |

FOREIGN PATENT DOCUMENTS

| | | |
|---|---|---|
| DE | 3640745 | 6/1987 |
| DE | 195 32 846 | 3/1997 |
| DE | 100 49 814 | 4/2002 |
| EP | 0103546 | 3/1984 |
| EP | 850 607 | 7/1998 |
| EP | 1057460 A1 | 6/2000 |
| EP | 1255510 | 11/2002 |
| EP | 157809 | 9/2005 |
| EP | 1469797 | 11/2005 |
| FR | 2815844 | 5/2000 |
| GB | 2433700 | 12/2007 |
| SU | 1271508 | 11/1986 |
| WO | 92/17118 | 10/1992 |
| WO | 94/03227 | 2/1994 |
| WO | 95/29640 | 11/1995 |
| WO | 97/17100 | 5/1997 |
| WO | 97/24080 | 7/1997 |
| WO | 99/12483 | 3/1999 |
| WO | 99/40964 | 8/1999 |
| WO | 99/47075 | 9/1999 |
| WO | 00/47136 | 8/2000 |
| WO | 00/47139 | 8/2000 |
| WO | 01/35870 | 5/2001 |
| WO | 01/49213 | 7/2001 |
| WO | 02/36048 | 5/2002 |
| WO | 02/41789 | 5/2002 |
| WO | 02/47575 | 6/2002 |
| WO | 02/49540 | 6/2002 |
| WO | 02/060352 | 8/2002 |
| WO | 03/003943 | 1/2003 |
| WO | 03/003949 | 1/2003 |

(56) References Cited

FOREIGN PATENT DOCUMENTS

| WO | 03/011195 | 2/2003 |
|---|---|---|
| WO | 03/030776 | 4/2003 |
| WO | 2004/019825 | 3/2004 |
| WO | 2004/089250 | 10/2004 |
| WO | 2005/004753 | 1/2005 |
| WO | 2005/046528 | 5/2005 |
| WO | 2006/014233 | 2/2006 |
| WO | 2006/026371 | 3/2006 |
| WO | 2008/005405 | 1/2008 |
| WO | 2008/047354 | 4/2008 |
| WO | 2008/138584 | 11/2008 |
| WO | 2009/002548 | 12/2008 |
| WO | 2009/029199 | 3/2009 |
| WO | 2009/042196 | 4/2009 |
| WO | 2009/045338 | 4/2009 |
| WO | 2009/061389 | 5/2009 |
| WO | 2009/091509 | 7/2009 |
| WO | 2009/111241 | 9/2009 |

OTHER PUBLICATIONS

Babaliaros, et al., "State of the Art Percutaneous Intervention for the Treatment of Valvular Heart Disease: A Review of the Current Technologies and Ongoing Research in the Field of Percutaneous Heart Valve Replacement and Repair," Cardiology 2007: 107:87-96.
Bailey. "Percutaneous Expandable Prosthetic Valves," In: Topol EJ, ed. Textbook of Interventional Cardiology. vol. II. Second edition. WB Saunders, Philadelphia, 1994:1268-1276.
Block, et al., "Percutaneous Approaches to Valvular Heart Disease," Current Cardiology Reports, vol. 7 (2005) pp. 108-113.
Bonhoeffer, et al, "Percutaneous Insertion of the Pulmonary Valve," Journal of the American College of Cardiology (United States), May 15, 2002, pp. 1664-1669.
Bonhoeffer, et al, "Percutaneous Replacement of Pulmonary Valve in a Right-Ventricle to Pulmonary-Artery Prosthetic Conduit with Valve Dysfunction," Lancet (England), Oct. 21, 2000, pp. 1403-1405.
Bonhoeffer. et al, "Transcatheter Implantation of a Bovine Valve in Pulmonary Position: A Lamb Study," Circulation (United States), Aug. 15, 2000, pp. 813-816.
Boudjemline, et al, "Percutaneous Aortic Valve Replacement: Will We Get There?" Heart (British Cardiac Society) (England), Dec. 2001, pp. 705-706.
Boudjemline, et al, "Percutaneous Implantation of a Biological Valve in the Aorta to Treat Aortic Valve Insufficiency—A Sheep Study," Medical Science Monitor—International Medical Journal of Experimental and Clinical Research (Poland), Apr. 2002, pp. BR113-BR116.

Boudjemline, et al, "Percutaneous Implantation of a Biological Valve in Aortic Position: Preliminary Results in a Sheep Study," European Heart Journal, Sep. 22, 2001, p. 630.
Boudjemline, et al, "Percutaneous Pulmonary Valve Replacement in a Large Right Ventricular Outflow Tract: An Experimental Study," Journal of the American College of Cardiology (United States), Mar. 17, 2004, pp. 1082-1087.
Boudjemline, et al, "Percutaneous Valve Insertion: A New Approach," Journal of Thoracic and Cardiovascular Surgery (United States), Mar. 2003, pp. 741-742.
Boudjemline, et al, "Steps Toward Percutaneous Aortic Valve Replacement," Circulation (United States), Feb. 12, 2002, pp. 775-778.
Coats, et al, "The Potential Impact of Percutaneous Pulmonary Valve Stent Implantation on Right Ventricular Outflow Tract Re-Intervention," European Journal of Cardio-Thoracic Surgery (England), Apr. 2005, pp. 536-543.
Cribier, A. et al, "Percutaneous Transcatheter Implantation of an Aortic Valve Prosthesis for Calcific Aortic Stenosis: First Human Case Description," Circulation (2002) 3006-3008.
Davidson et al., "Percutaneous therapies for valvular heart disease," Cardiovascular Pathology 15 (2006) 123-129.
Hanzel, et al., "Complications of percutaneous aortic valve replacement: experience with the Criber-Edwards™ percutaneous heart valve," EuroIntervention Supplements (2006), I (Supplement A) A3-A8.
Lutter, et al, "Percutaneous Aortic Valve Replacement: An Experimental Study. I. Studies on Implantation," The Journal of Thoracic and Cardiovascular Surgery, Apr. 2002, pp. 768-776.
Lutter, et al, "Percutaneous Valve Replacement: Current State and Future Prospects," Annals of Thoracic Surgery (Netherlands), Dec. 2004, pp. 2199-2206.
Medtech Insight, "New Frontiers in Heart Valve Disease," vol. 7, No. 8 (2005).
Palacios. "Percutaneous Valve Replacement and Repair, Fiction or Reality?" Journal of American College of Cardiology, vol. 44, No. 8 (2004) pp. 1662-1663.
Pelton et al., "Medical Uses of Nitinol," Materials Science Forum vols. 327-328, pp. 63-70 (2000).
Ruiz, "Transcathether Aortic Valve Implantation and Mitral Valve Repair: State of the Art," Pediatric Cardiology, vol. 26, No. 3 (2005).
Saliba, et al, "Treatment of Obstructions of Prosthetic Conduits by Percutaneous Implantation of Stents," Archives des Maldies du Coeur et des Vaisseaux (France), 1999, pp. 591-596.
Webb, et al., "Percutaneous Aortic Valve Implantation Retrograde from the Femoral Artery," Circulation (2006), 113;842-850.
Stassano et al., "Mid-term results of the valve-on-valve technique for bioprosthetic failure," Eur. J. Cardiothorac. Surg. 2000; 18:453-457.
Pavcnik et al., "Aortic and venous valve for percutaneous insertion," Min. Invas. Ther. & Allied Technol. 2000, vol. 9, pp. 287-292.

* cited by examiner

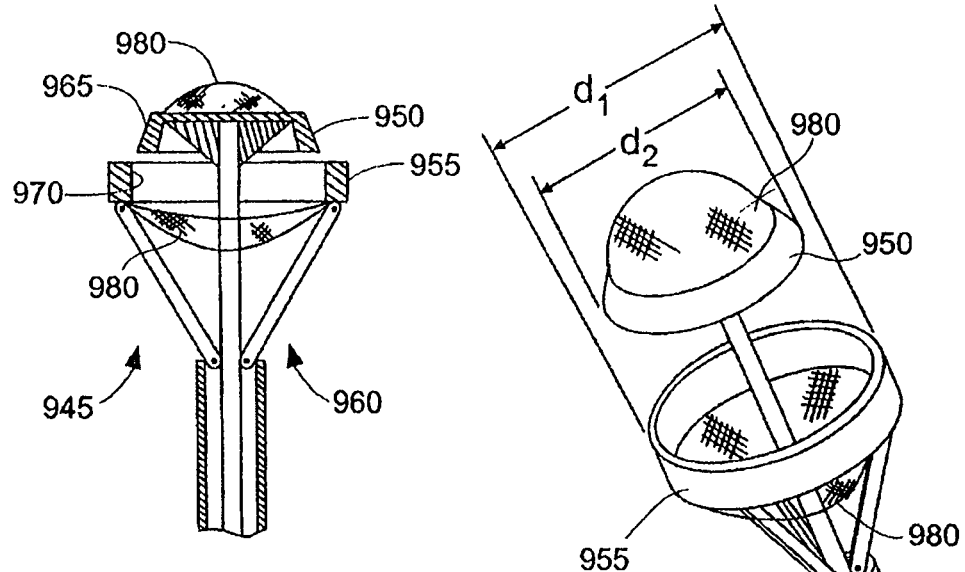
FIG. 14
FIG. 15
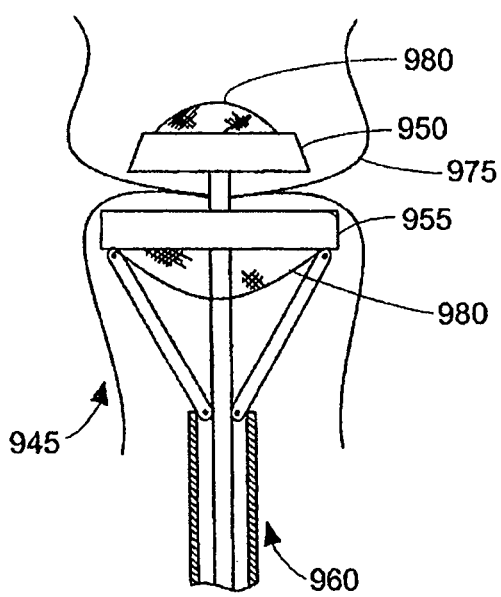
FIG. 13
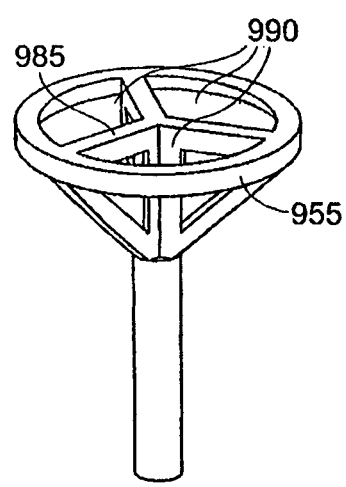
FIG. 16

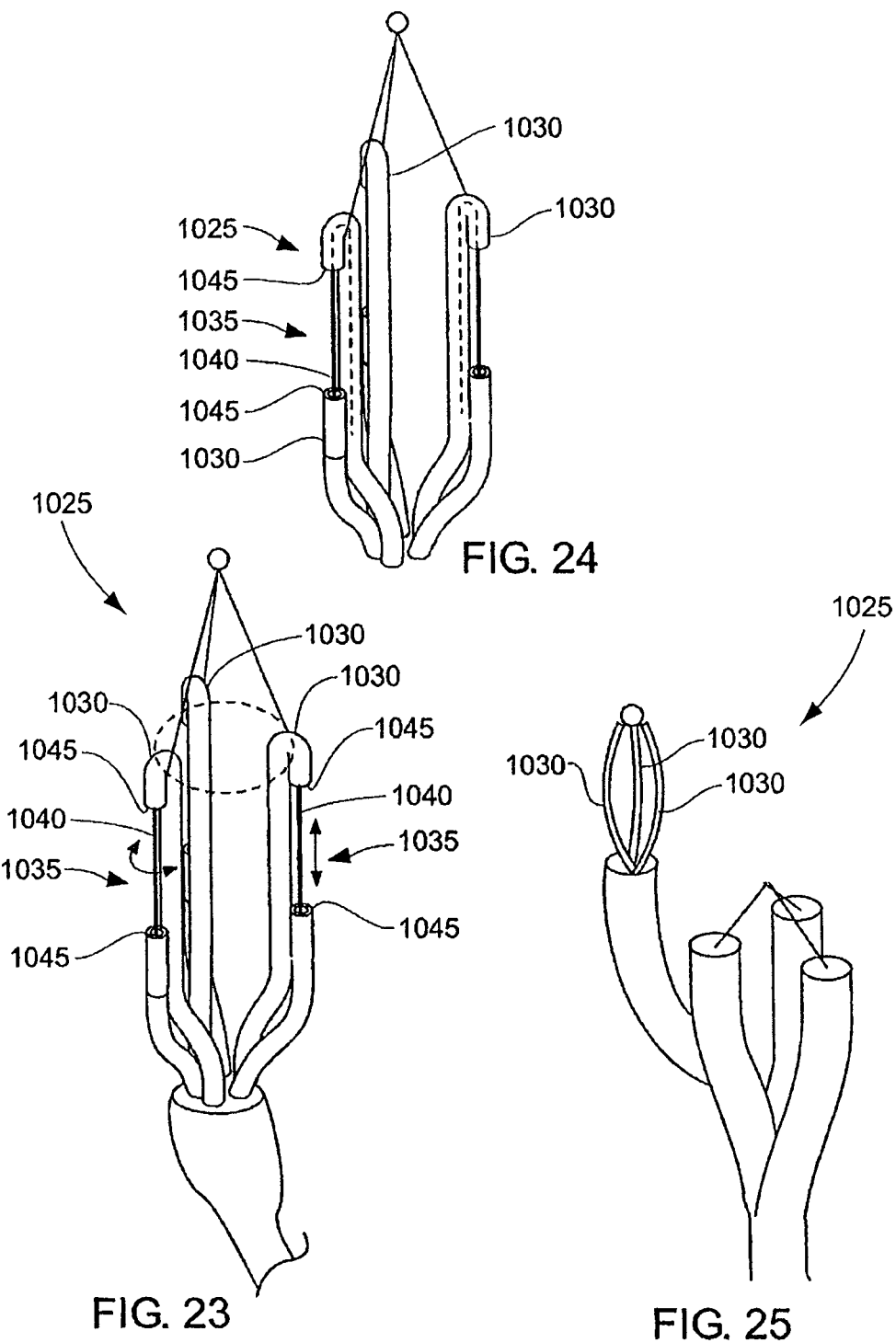

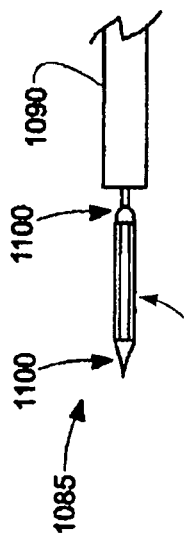
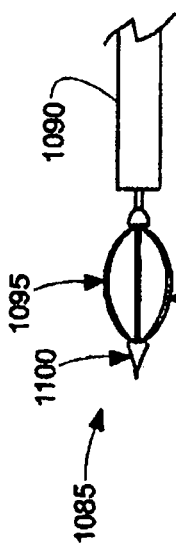
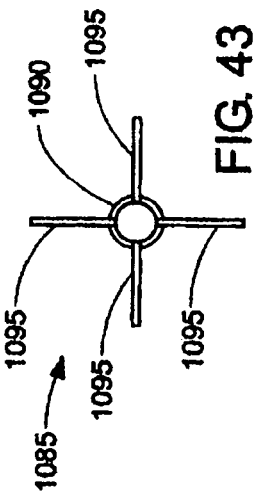
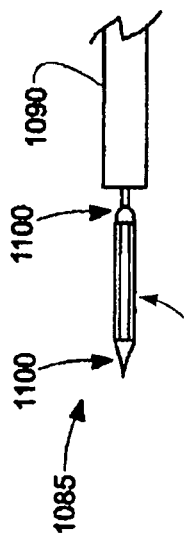
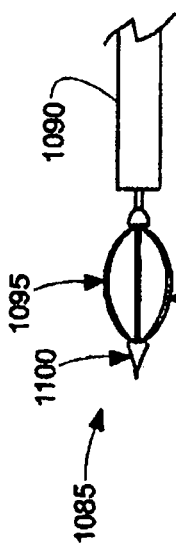
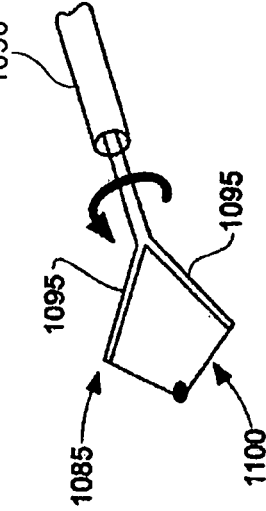

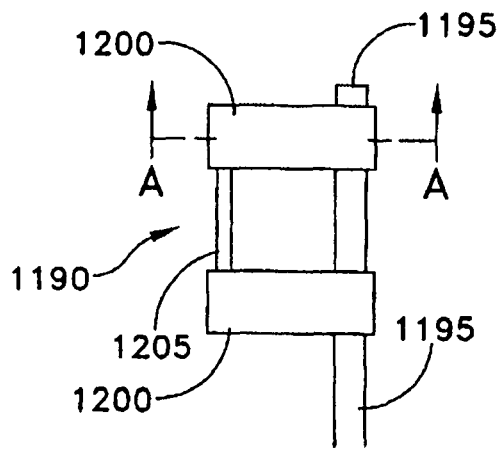
FIG. 62
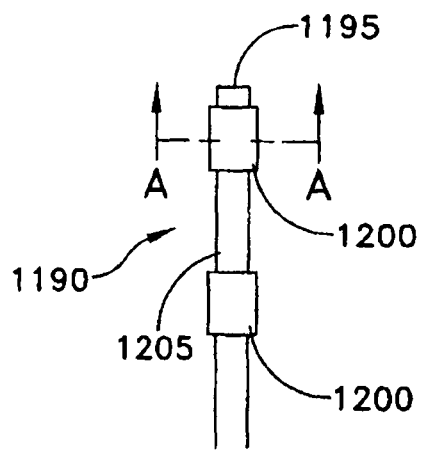
FIG. 63
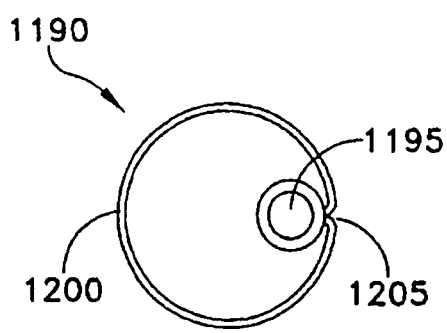
FIG. 62 A-A
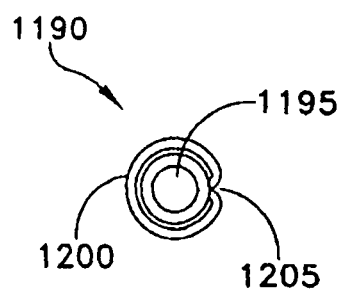
FIG. 63 A-A
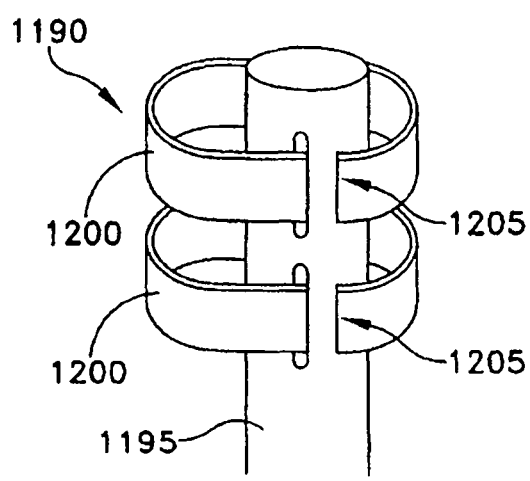
FIG. 61

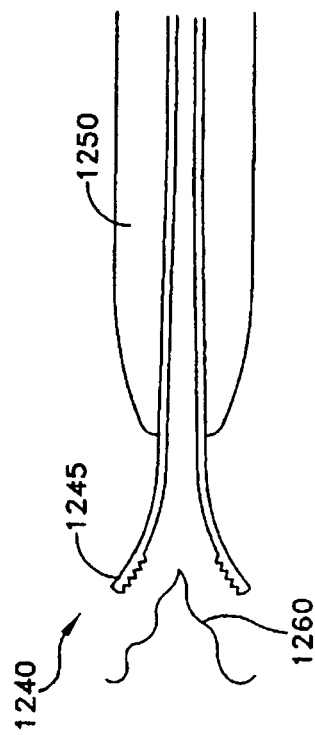
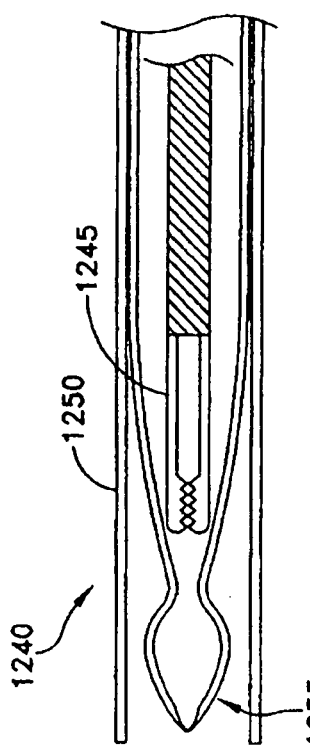
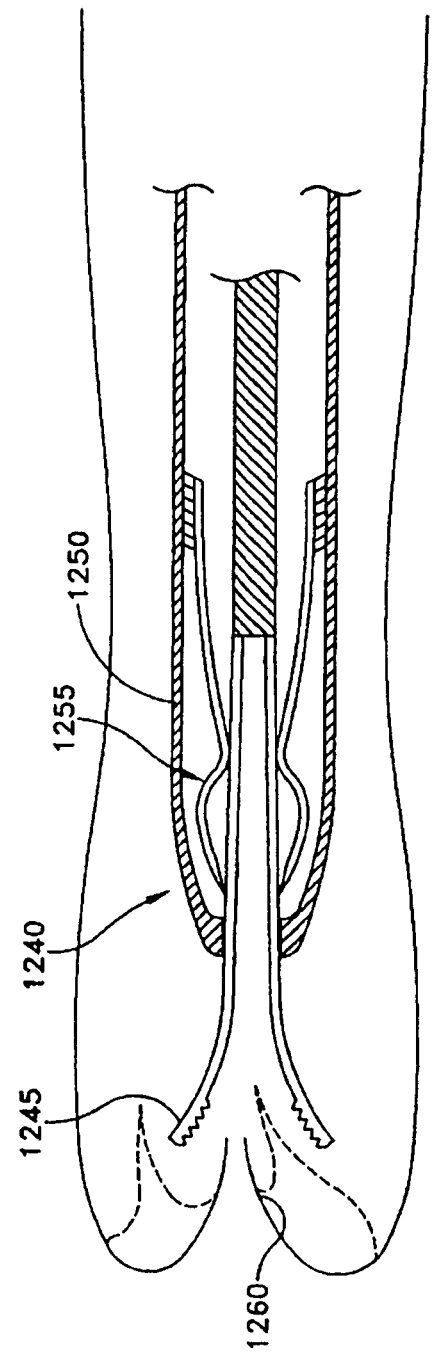

METHOD AND APPARATUS FOR RESECTING AND REPLACING AN AORTIC VALVE

REFERENCE TO PENDING PRIOR PATENT APPLICATIONS

The present application is a divisional of U.S. application Ser. No. 10/414,741, filed on Apr. 16, 2003 for Method and Apparatus for Resecting and Replacing an Aortic Valve, now granted as U.S. Pat. No. 7,201,161; which is a continuation-in-part of U.S. application Ser. No. 09/896,259, filed on Jun. 29, 2001 for Method and Apparatus for Performing a Procedure on a Cardiac Valve, now granted as U.S. Pat. No. 6,769,434; the present application also claims priority to U.S. Provisional Patent Application Ser. No. 60/373,042, filed on Apr. 16, 2002, for Method and Apparatus for Resecting and Replacing an Aortic Valve; and U.S. Provisional Patent Application Ser. No. 60/425,891, filed on Nov. 13, 2002, for Method and Apparatus for Resecting and Replacing an Aortic Valve; all of the specifications of which are incorporated by reference herein, in their entirety.

FIELD OF THE INVENTION

This invention relates to apparatus and methods for performing cardiac surgery in general, and more particularly to apparatus and methods for performing cardiac surgery while the heart is beating.

BACKGROUND OF THE INVENTION

Of all valvular heart lesions, aortic stenosis carries the worst prognosis. Within one year of diagnosis, approximately half of all patients with critical aortic stenosis have died, and by three years, this figure rises to approximately 80%. Currently, the most prominent and effective treatment for patients with aortic stenosis is aortic valve replacement via open heart surgery. Unfortunately, this procedure is a substantial and invasive undertaking for the patient.

While there have been significant advances in heart valve technology over the past 30 years, there has been little progress in the development of safer and less invasive valve delivery systems. Aortic valve replacement currently requires a sternotomy or thoracotomy, use of cardiopulmonary bypass to arrest the heart and lungs, and a large incision on the aorta. The native valve is resected through this incision and then a prosthetic valve is sutured to the inner surface of the aorta with a multitude of sutures passing only partly into the wall of the aorta. Given the current invasiveness of this procedure and the requirement to utilize cardiopulmonary bypass, aortic valve replacement surgery is associated with a high risk of morbidity and mortality. This is especially true in elderly patients, and in those patients who require concomitant coronary artery bypass grafting. Even when a good surgical result is achieved, virtually all patients require approximately 6 weeks to several months to fully recover from the procedure. In order to decrease these associated risks of aortic valve surgery, many have pursued novel approaches and technologies.

Less invasive approaches to aortic valve surgery have generally followed two paths.

In the 1980's, there was a flurry of interest in percutaneous balloon valvotomy. In this procedure, a cardiologist introduced a catheter through the femoral artery to dilate the patient's aortic valve, thereby relieving the stenosis. Using the technology available at that time, success was limited: the valve area was increased only minimally, and nearly all patients had restenosis within one year.

More recently, surgeons have approached the aortic valve via smaller chest wall incisions. However, these approaches still require cardiopulmonary bypass and cardiac arrest, which themselves entail significant morbidity and a prolonged post-operative recovery.

The ideal minimally invasive approach to the treatment of aortic valve disease requires aortic valve replacement without cardiopulmonary bypass and without cardiac arrest. Such an approach would greatly reduce patient morbidity and mortality and hasten recovery. Unfortunately, although there has been great progress in the treatment of coronary artery disease without cardiopulmonary bypass (e.g., angioplasty, with or without stenting, and "off-pump" coronary artery bypass grafting), similar advances have not yet been realized in heart valve surgery. With an aging population and improved access to advanced diagnostic testing, the incidence and accurate diagnosis of aortic stenosis will continue to increase. The development of a system for "off-pump" aortic valve replacement would be of significant benefit to this increasing patient population.

There are three important challenges to replacing a diseased aortic valve without cardiopulmonary bypass.

The first challenge is to remove the diseased valve without causing stroke or other ischemic events that might result from the liberation of particulate material while removing the diseased valve.

The second challenge is to prevent cardiac failure during removal of the diseased valve. In this respect it must be appreciated that the aortic valve continues to serve a critical function even when it is diseased. However, as the diseased valve is removed, it becomes acutely and severely incompetent, causing the patient to develop heart failure which results in death unless the function of the valve is taken over by another means.

The third challenge is placing a prosthetic valve into the vascular system and affixing it to the wall of the aorta. More particularly, during cardiac rhythm, the aortic and arterial pressures are substantially greater than atmospheric pressure. Therefore, any sizable incision made to the aorta in order to insert a standard valve prosthesis into the arterial system creates the potential for uncontrollable bleeding from the incision site. Furthermore, even if bleeding is successfully controlled, pressures within the aorta may result in weakening of the aorta caused by aortic wall dissection. In addition, large incisions on the aorta also increase the potential for liberating plaque from the aortic wall that can lead to embolic complications.

For these reasons, prior art valve prostheses potentially suitable for off-pump implantation have relied upon relatively flimsy expandable structures to support and secure the valve within the aorta. More particularly, these prosthetic valves are constructed so that they can be compressed to a relatively small dimension suitable for insertion into the arterial system, advanced to the site of the aortic valve, and then expanded against the aortic wall. Unfortunately, however, none of these relatively flimsy valve prostheses have proven adequate to endure the repetitive stresses undergone by the aortic valve over the ten to twenty years typically required.

In addition to the foregoing, the precise placement of such expandable prosthetic valves in the correct sub-coronary position can be extremely challenging, particularly in view of the high pressure, pulsatile blood flow passing through the aorta. Furthermore, expandable prosthetic valves would typically be positioned from a remote artery, which would reduce the ability to precisely control the placement and positioning of the device and therefore would increases the risk of obstructing the coronary arteries. The expandable prosthetic valves are held on the ends of elongate, flexible catheters that are threaded into the aorta, around the aortic arch and then expanded. The pulsatile flow during cardiac rhythm induces a to-and-fro motion of the valve prosthesis relative to the aorta that makes the timing of valve expansion critical for proper placement of the expandable prosthetic valve and hence the survival of the patient.

Finally, many of the challenges discussed in the foregoing section pertaining to aortic valve replacement are also relevant to other procedures in the aortic root such as aortic valve resection, aortic valve decalcification, stent grafting for aortic dissections, etc.

SUMMARY OF THE INVENTION

It is, therefore, one object of the present invention to enable the passage of a device from the left atrium, through the left ventricle, and into the arterial system.

Further, another object of the present invention is to enable the implantation of a device in the arterial system without cardiopulmonary bypass.

Further, another object of the present invention is to enable the implantation of a prosthetic valve in the arterial system without cardiopulmonary bypass.

Another object of the present invention is to allow the insertion of such a valve while minimizing the risks to the patient posed by large arterial incisions.

And another object of the present invention is to simplify the precise placement of such a valve.

Further, another object of the present invention is to enable the implantation of a device other than a valve, such as but not limited to a valve resection tool, a decalcifying tool, an aortic valve repair tool, or a stented aortic graft, in the arterial system without cardiopulmonary bypass.

Another object of the present invention is to allow the insertion of a device other than a valve, such as but not limited to a valve resection tool, a decalcifying tool, an aortic valve repair tool, or a stented aortic graft, while minimizing the risks to the patient posed by large arterial incisions.

And another object of the present invention is to simplify the precise placement of a device other than a valve, such as but not limited to a valve resection tool, a decalcifying tool, an aortic valve repair tool, or a stented aortic graft.

The present invention relates to a method and apparatus for positioning a device in the arterial system. More specifically, the present invention relates to a method and apparatus for positioning an aortic valve prosthesis in the aorta or aortic outflow tract, with or without cardiopulmonary bypass.

One aspect of the present invention is a method for deploying an aortic valve prosthesis. This valve prosthesis may include any of the known aortic valves including, but not limited to, stented and unstented bioprosthetic valves, stented mechanical valves, and expandable or self-expanding valves, whether biological or artificial.

In one aspect of the invention, there is provided a method of inserting a prosthesis or device from a lower pressure region into a higher pressure region of the cardiovascular system comprising the steps of: making an opening in a wall of a lower pressure region of the cardiovascular system; advancing the prosthesis or device through the opening and into the lower pressure region; and advancing the prosthesis or device through a natural barrier between the lower pressure region and the higher pressure region.

In another aspect of the invention, there is provided a method of inserting a prosthesis or device into a vessel within the arterial system comprising the steps of: making an opening in a wall of a low pressure region of the heart; advancing the prosthesis or device through the opening and into the low pressure region; advancing the prosthesis or device through a natural barrier between the low pressure region and the left ventricle; and advancing the prosthesis or device from the left ventricle into the arterial system and the vessel.

And in another aspect of the invention, there is provided a method of inserting a prosthesis or device into a vessel within the arterial system comprising the steps of: making an opening in a wall of the left atrium; advancing the prosthesis or device through the opening and into the left atrium; advancing the prosthesis or device through the mitral valve and into the left ventricle; and advancing the prosthesis or device from the left ventricle into the arterial system and the vessel.

And in another aspect of the present invention, there is provided a method for positioning a device in the arterial system comprising the steps of: making a first opening leading to the left atrium; passing a valve prosthesis through the first opening and into a cardiac chamber of the left side of the heart using a first manipulation instrument; making a second opening in the arterial system and advancing one end of a second manipulation instrument through the second opening and into the aforementioned cardiac chamber; securing the second manipulation instrument to the valve prosthesis; and then using the second manipulation instrument to retract at least some portion of the valve prosthesis out of the aforementioned cardiac chamber.

An alternative method for positioning a device in the arterial system comprises the steps of: making an opening leading to the left atrium; passing a valve prosthesis through the opening and into a cardiac chamber of the left side of the heart using an articulating manipulation instrument; using the articulating manipulation instrument to guide the valve prosthesis into the arterial cardiac chamber; releasing the valve prosthesis into a desired position: and then retracting at least a portion of the articulating manipulation instrument out of the aforementioned cardiac chamber and left atrium.

The pressure of blood flowing through the left atrium is very low, peaking at a few inches of water during the cardiac cycle. This pressure is a small fraction of that found within the arterial system and thus permits insertion of a conventional valve prosthesis through a relatively large opening formed in the wall of the left atrium without the risk of uncontrollable bleeding. In this respect it will be appreciated that various methods are known to those skilled in the art for controlling bleeding from an incision into the left atrium. The left atrium also rarely suffers from atherosclerotic plaque formation or calcification, thus minimizing the risk of embolic debris during such incision.

Another aspect of the present invention is the use of a prosthesis holding apparatus for releasably holding the valve prosthesis during manipulation to its implant site. The prosthesis holding apparatus may be secured to the prosthetic valve at any suitable location(s) through the use of any of a variety of approaches including, but not limited to, suture loops, barbs, hooks, grasping jaws, opposing magnetic poles, friction fits and the like. The prosthesis holding apparatus is configured to provide first and second manipulation mounts for engagement by the aforementioned first and second manipulation instruments, respectively, whereby the prosthetic valve can be delivered to its implant site. This construction is highly advantageous in that it permits the valve prosthesis to be passed easily and reliably from the first manipulation instrument to the second manipulation instrument within the vascular system.

In an alternative preferred embodiment, the prosthetic holding apparatus is attached on the ventricular side of the prosthesis. The aforementioned first manipulation instrument would articulate at or near the prosthetic valve to facilitate manipulation of the prosthesis holding apparatus (and hence the prosthesis itself) through the smallest possible incision site, then through the left atrium, the mitral valve and within the heart to align and position the prosthesis within the aortic annulus or left ventricular outflow track. In this alternative embodiment, there is no need for the aforementioned second manipulation instrument or the second manipulation mount.

In addition, if the prosthesis holding apparatus is attached on the aortic side of the prosthesis, the manipulation instrument may articulate and may be introduced into the arterial system, brought across the mitral valve into the left atrium, out the left atrium to pick up the prosthesis holding apparatus (and hence the prosthesis) and then retracted back to position the prosthesis directly into the aortic annulus without the need for another manipulation instrument.

In another form of the present invention, there is provided an apparatus for resecting a diseased heart valve, the apparatus comprising:

a first frame member and a second frame member configured in opposition to one another;

a cutting edge configured on the first frame member;

an adjustable connector positionably joining the first frame member to the second frame member, the adjustable connector configured to selectively position the first frame member and the second frame member between a first position and a second position, wherein the first frame member and the second frame member are positioned apart from one another in the first position so as to allow at least a portion of the diseased heart valve therebetween, and the first frame member and the second frame member are positioned together in the second position so as to cut the at least a portion of the diseased heart valve therebetween with the cutting blade so as to resect the diseased heart valve;

an actuator configured in operable connection to the adjustable connector, the actuator configurable to selectively position the adjustable connector between the first position and the second position; and a first screen portion and a second screen portion disposed on the first frame portion and the second frame portion, respectively, the first screen portion and the second screen portion configured to allow blood flow through first frame member and second frame member and to contain the at least a portion of the diseased heart valve between the first frame member and the second frame member.

In another form of the present invention, there is provided a method of resecting a diseased heart valve, the method comprising:

providing apparatus for resecting the diseased heart valve, the apparatus comprising:

a first frame member and a second frame member configured in opposition to one another;

a cutting edge configured on the first frame member;

an adjustable connector positionably joining the first frame member to the second frame member, the adjustable connector configured to selectively position the first frame member and the second frame member between a first position and a second position, wherein the first frame member and the second frame member are positioned apart from one another in the first position so as to allow at least a portion of the diseased heart valve therebetween, and the first frame member and the second frame member are positioned together in the second position so as to cut the at least a portion of the diseased heart valve therebetween with the cutting blade so as to resect the diseased heart valve;

an actuator configured in operable connection to the adjustable connector, the actuator configurable to selectively position the adjustable connector between the first position and the second position; and a first screen portion and a second screen portion disposed on the first frame portion and the second frame portion, respectively, the first screen portion and the second screen portion configured to allow blood flow through first frame member and second frame member and to contain the at least a portion of the diseased heart valve between the first frame member and the second frame member;

positioning the first frame member and the second frame member on opposed sides of the diseased heart valve, with the first frame member and the second frame member in the first position;

closing the first frame member and the second frame member from the first position to the second position by manipulating the actuator in operable connection to the adjustable connector so as to move the cutting edge through the at least a portion of the diseased heart valve; and removing from a patient the first frame member and the second frame member closed together in the second position, with the at least a portion of the diseased heart valve therebetween.

In another form of the present invention, there is provided a method of resecting a diseased heart valve, the method comprising:

positioning a first frame member and a second frame member on opposed sides of the diseased heart valve, with the first frame member and the second frame member positioned apart from one another;

closing the first frame member and the second frame member toward one another so as to pass a cutting edge disposed on the first frame member through at least a portion of the diseased heart valve; and removing from the patient the first frame member and the second frame member closed together, with the at least a portion of the diseased heart valve therebetween.

In another form of the present invention, there is provided an apparatus for resecting a diseased heart valve, the apparatus comprising:

a power shaver having a proximal end and a distal end, the power shaver defining a longitudinal axis from the proximal end to the distal end, and a cutting element disposed adjacent to the distal end of the power shaver; and a power shaver guide having a first end and a second end in opposition to one another, the power shaver guide defining a first opening extending into the first end, the first opening defining a first axis from the first end of the power shaver guide to the second end of the power shaver guide, the first opening configured to receive a portion of the power shaver therein, the power shaver guide having a given width from the first opening to an outer surface in a direction perpendicular to the first axis, the given width of the power shaver guide configured to prevent the wall of a cardiovascular structure from being cut by the power shaver disposed within the first opening and to permit the power shaver to be placed within the diseased valve.

In another form of the present invention, there is provided a method for resecting a diseased heart valve comprising:

providing apparatus for resecting the diseased heart valve, the apparatus comprising:

a power shaver having a proximal end and a distal end, the power shaver defining a longitudinal axis from the proximal end to the distal end, and a cutting element disposed adjacent to the distal end of the power shaver; and a power shaver guide having a first end and a second end in opposition to one another, the power shaver guide defining a first opening extending into the first end, the first opening defining a first axis from the first end of the power shaver guide to the second end of the power shaver guide, the first opening configured to receive a portion of the power shaver therein, the power shaver guide having a given width from the first opening to an outer surface in a direction perpendicular to the first axis, the given width of the power shaver guide configured to prevent the wall of a cardiovascular structure from being cut by the power shaver disposed within the first opening and to permit the power shaver to be placed within the diseased valve;

positioning the power shaver within the power shaving guide;

positioning the power shaver and power shaving guide through a cardiovascular structure to the diseased heart valve; and cutting the diseased valve with the cutting element of the power shaver so as to resect the diseased heart valve.

In another form of the present invention, there is provided an apparatus for resecting a diseased heart valve, the apparatus comprising:

a set of at least three expandable arms having a proximal end and a distal end in opposition to one another, the set of expandable arms defining a longitudinal axis from the proximal end to the distal end;

a first restraining element and a second restraining element configured at the proximal end of the set of expandable arms and the distal end of the set of at least three expandable arms, respectively, the first restraining element and the second restraining element configured to selectively position the set of at least three expandable arms between a first position and a second position, the set of at least three expandable arms having a given width in a perpendicular direction to the longitudinal axis at the first position and having a larger width in the perpendicular direction to the longitudinal axis at the second position; and a cutting device disposed on at least one of the at least three expandable arms, the cutting device configured to cut through the diseased heart valve.

In another form of the present invention, there is provided a method for resecting a diseased heart valve, the apparatus comprising:

providing apparatus for resecting the diseased heart valve, the apparatus comprising:

a set of at least three expandable arms having a proximal end and a distal end in opposition to one another, the set of expandable arms defining a longitudinal axis from the proximal end to the distal end;

a first restraining element and a second restraining element configured at the proximal end of the set of expandable arms and the distal end of the set of at least three expandable arms, respectively, the first restraining element and the second restraining element configured to selectively position the set of at least three expandable arms between a first position and a second position, the set of at least three expandable arms having a given width in the perpendicular direction to the longitudinal axis at the first position and having a larger width in the perpendicular direction to the longitudinal axis at the second position; and a cutting device disposed on at least one of the at least three expandable arms, the cutting device configured to cut through the diseased heart valve;

positioning the set of at least three expandable arms adjacent to the diseased heart valve;

expanding the set of at least three expandable arms from the first position to the second position; and cutting the diseased heart valve with the cutting device disposed on the at least one of the at least three expandable arms.

In another form of the present invention, there is provided an apparatus for resecting a diseased heart valve, the apparatus comprising:

a first frame member and a second frame member configured in opposition to one another;

a cutting edge configured on the first frame member;

an adjustable connector positionably joining the first frame member to the second frame member, the adjustable connector configured to selectively position the first frame member and the second frame member between a first position and a second position, wherein the first frame member and the second frame member are positioned apart from one another in the first position so as to allow at least a portion of the diseased heart valve therebetween, and the first frame member and the second frame member are positioned together in the second position so as to cut the at least a portion of the diseased heart valve therebetween with the cutting blade so as to resect the diseased heart valve;

an actuator configured in operable connection to the adjustable connector, the actuator configurable to selectively position the adjustable connector between the first position and the second position; and at least two spikes extending from the first frame member toward the second frame member, the at least two spikes being configured to pierce and secure leaflets of the diseased heart valve as the first frame member and the second frame member are positioned toward one another.

In another form of the present invention, there is provided an apparatus for resecting a diseased heart valve, the apparatus comprising:

a catheter having a proximal end and a distal end, the catheter defining a longitudinal axis from the proximal end to the distal end; and a set of blades positionably configurable at the distal end of the catheter, a hinge mechanism holding the distal end of the set of blades together, and a control rod extending from the proximal end of the blades into the catheter, the control rod being configured to selectively position the set of blades from a first position within the catheter to a second position outside of the distal end of the catheter, to selectively expand the set of blades from a narrow width for disposition within the catheter to a wide width for cutting portions of the diseased heart valve with the set of blades, and to rotate the set of blades with respect to the longitudinal axis of the catheter.

In another form of the present invention, there is provided a method of resecting a diseased heart valve, the method comprising:

providing apparatus for resecting the diseased heart valve, the apparatus comprising:

a catheter having a proximal end and a distal end, the catheter defining a longitudinal axis from the proximal end to the distal end; and a set of blades positionably configurable at the distal end of the catheter, a hinge mechanism holding the distal end of the set of blades together, and a control rod extending from the proximal end of the blades into the catheter, the control rod being configured to selectively position the set of blades from a first position within the catheter to a second position outside of the distal end of the catheter, to selectively expand the set of blades from a narrow width for disposition within the catheter to a wide width for cutting portions of the diseased heart valve with the set of blades, and to rotate the set of blades with respect to the longitudinal axis of the catheter;

placing distal end of the catheter adjacent to the diseased heart valve;

positioning the set of blades from the first position within the catheter to the second position outside of the distal end of the catheter;

expanding the set of blades from the narrow width for disposition within the catheter to the wide width for cutting portions of the diseased heart valve with the set of blades; and rotating the set of blades with respect to the longitudinal axis of the catheter so as to cut through the diseased heart valve.

In another form of the present invention, there is provided an apparatus for resecting a diseased heart valve, the apparatus comprising:

a catheter having a proximal end and a distal end, and the catheter defining a longitudinal axis from the proximal end to the distal end;

a control rod having a proximal end and a distal end, the control rod being selectively positionable through the catheter and being selectively rotatable with respect to the longitudinal axis of the catheter;

an outer shell portion having a first edge and a second edge in opposition to one another, the outer shell portion having an inwardly facing side and an outwardly facing side in opposition to one another, the first edge of the outer shell portion being attached to the control rod along a surface thereof parallel to the longitudinal axis of the catheter, and the outer shell portion adapted to be wound around the control rod; and a spring having a first end and a second end, the first end of the spring being attached to the inwardly facing side of the outer shell portion adjacent to the second edge thereof, and the spring being disposed against the inwardly facing side of the outer shell portion;

wherein rotation of the control rod in a first direction in combination with a force applied by the spring contracts the outer shell portion toward the control rod so as to reduce a maximum outer diameter of the outer shell in a given direction perpendicular to the longitudinal axis of the catheter, and rotation of the control rod in a second direction in combination with the force applied by the spring rolls the outer shell portion away from the control rod so as to expand the maximum outer diameter of the outer shell portion in the given direction perpendicular to the longitudinal axis of the catheter.

In another form of the present invention, there is provided a method for resecting a diseased heart valve, the method comprising:

providing apparatus for resecting a diseased heart valve, the apparatus comprising:

a catheter having a proximal end and a distal end, and the catheter defining a longitudinal axis from the proximal end to the distal end;

a control rod having a proximal end and a distal end, the control rod being selectively positionable through the catheter and being selectively rotatable with respect to the longitudinal axis of the catheter;

an outer shell portion having a first edge and a second edge in opposition to one another, the outer shell portion having an inwardly facing side and an outwardly facing side in opposition to one another, the first edge of the outer shell portion being attached to the control rod along a surface thereof parallel to the longitudinal axis of the catheter, and the outer shell portion adapted to be wound around the control rod; and a spring having a first end and a second end, the first end of the spring being attached to the inwardly facing side of the outer shell portion adjacent to the second edge thereof, and the spring being disposed against the inwardly facing side of the outer shell portion;

positioning the distal end of the catheter adjacent to the diseased heart valve;

rotating the control rod in the second direction so as to expand the outer shell portion; and withdrawing the apparatus from the human body.

In another form of the present invention, there is provided an apparatus for resecting a diseased heart valve, the apparatus comprising:

a tubular body having a proximal end and a distal end, the tubular body defining a longitudinal axis from the proximal end to the distal end; and an auger blade disposed within the tubular body and configured to selectively rotate with respect to the longitudinal axis of the tubular body;

the tubular body defining an opening configured therein so as to allow portions of the diseased heart valve therein, and the opening defining a junction region at a location where the auger blade contacts the tubular body and cuts the portions carried by the auger blade thereto.

In another form of the present invention, there is provided a method for resecting a diseased heart valve, the method comprising:

positioning an opening of a tubular body adjacent to the diseased heart valve; and cutting the diseased heart valve with an auger blade rotating within the tubular body.

In another form of the present invention, there is provided an apparatus for resecting a diseased heart valve, the apparatus comprising:

an inner rod having a proximal end and a distal end, the inner rod defining a longitudinal axis from the proximal end to the distal end, and the inner rod defining a first opening and a second opening in a lateral side thereof between the proximal end and the distal end;

a first outer shell and a second outer shell each having a selectively configurable length through the first opening and the second opening of the inner rod, respectively, the first outer shell and the second outer shell configured to be radially expandable depending on the length of the first outer shell and the second outer shell configured through the first opening and the second opening, respectively; and a blade extending between the first outer shell and the second outer shell, the blade being radially expandable away from the inner rod together with the first outer shell.

In another form of the present invention, there is provided an apparatus for resecting a diseased heart valve, the apparatus comprising:

an inner cylinder having an outer tube rotatably disposed thereto, the inner cylinder and outer tube having a distal end and a proximal end, and the inner cylinder defining a longitudinal axis from the distal end to the proximal end;

at least one barb extending away from the distal end of the inner cylinder; and three blades pivotally attached to the distal end of the outer tube, the three blades being selectively configurable in a first position and a second position, the first position configured with the blades closed toward one another so as to cover the at least one barb and provide a narrow cross-section therethrough in a perpendicular direction to the longitudinal axis, and a second position configured with the blades opened away from one another so as to expose the at least one barb and provide a cutting diameter having a greater cross-section therethrough than the narrow cross-section in the perpendicular direction to the longitudinal axis;

wherein the three blades are positioned closed toward one another through a body to a location adjacent to a diseased heart valve, the three blades are opened away from one another so as to expose the at least one barb extending away from the distal end of the inner cylinder, the inner cylinder is positioned toward the diseased heart valve so as to spear the at least one barb therethrough, and the outer tube is rotated around the inner cylinder so as to rotate the three blades to cut the diseased valve.

In another form of the present invention, there is provided a method for resecting a diseased heart valve, the method comprising:

providing apparatus for resecting a diseased heart valve, the apparatus comprising:

an inner cylinder having an outer tube rotatably disposed thereto, the inner cylinder and outer tube having a distal end and a proximal end, and the inner cylinder defining a longitudinal axis from the distal end to the proximal end;

at least one barb extending away from the distal end of the inner cylinder; and three blades pivotally attached to the distal end of the outer tube, the three blades being selectively configurable in a first position and a second position, the first position configured with the blades closed toward one another so as to cover the at least one barb and provide a narrow cross-section thereto in a perpendicular direction to the longitudinal axis, and a second position configured with the blades opened away from one another so as to expose the at least one barb and provide a cutting diameter having a greater cross-section therethrough than the narrow cross-section in the perpendicular direction to the longitudinal axis;

wherein the three blades closed toward one another through a body to a location are positioned adjacent to a diseased heart valve, the three blades are opened away from one another so as to expose the at least one barb extending away from the distal end of the inner cylinder, the inner cylinder is positioned toward the diseased heart valve so as to spear the at least one barb therethrough, and the outer tube is rotated around the inner cylinder so as to rotate the three blades to cut the diseased valve;

positioning the three blades toward the diseased heart valve;

opening the three blades away from one another so as to expose the at least one barb; spearing the at least one barb through the diseased heart valve; and rotating the three blades so as to cut the diseased valve.

In another form of the present invention, there is provided an apparatus for resecting a diseased heart valve, the apparatus comprising:

a chamber having a proximal end and a distal end, and a sidewall extending between the proximal end and the distal end;

a retractable barb selectively positionable between a first position and a second position, the retractable bar being configured within the distal end of chamber in the first position, and the retractable bar being configured to extend beyond the distal end of the chamber in the second position; and a set of blades surrounding the distal end of the chamber;

wherein the retractable barb extends from the chamber, pierces a portion of the diseased heart valve, and retracts into the chamber; and wherein the set of blades cuts through the portion of the diseased heart valve pierced by the retractable barb as the retractable barb retracts into the chamber.

In another form of the present invention, there is provided a method for resecting a diseased heart valve, the method comprising:

providing apparatus for resecting the diseased heart valve, the apparatus comprising:

a chamber having a proximal end and a distal end, and a sidewall extending between the proximal end and the distal end;

a retractable barb selectively positionable between a first position and a second position, the retractable bar being configured within the distal end of chamber in the first position, and the retractable bar being configured to extend beyond the distal end of the chamber in the second position; and a set of blades surrounding the distal end of the chamber;

wherein the retractable barb extends from the chamber, pierces a portion of the diseased heart valve, and retracts into the chamber; and wherein the set of blades cuts through the portion of the diseased heart valve pierced by the retractable barb as the retractable barb retracts into the chamber;

positioning the distal end of the chamber adjacent to the diseased heart valve;

extending the retractable barb from the chamber;

piercing the portion of the diseased heart valve with the retractable barb;

retracting the retractable barb into the chamber; and cutting through the portion of the diseased heart valve pierced by the retractable barb with the set of blades.

In another form of the present invention, there is provided an apparatus for resecting a diseased heart valve, the apparatus comprising:

a body portion having a proximal end and a distal end, the body portion defining a longitudinal axis from the proximal end to the distal end, and the body portion defining an opening at the distal end thereof;

a grasping tool being selectively positionable within the body portion along the longitudinal axis from a first position to a second position, the grasping tool being configured within the body portion in the first position, the grasping tool extending through the opening at the distal end of the body portion in the second position, and the grasping tool being configured to selectively close together a first portion and a second portion so as to selectively grip the diseased heart valve therebetween; and a cutting element disposed within the body portion at a given distance from the opening, the cutting element configured to close together to cut the diseased heart valve therebetween at the given distance from the opening after the grasping tool is withdrawn to a given location between the cutting element and the proximal end of the body portion;

wherein a portion of the diseased heart valve portion cut away from an intact portion of the diseased heart valve is contained within the body portion.

In another form of the present invention, there is provided a method of resecting a diseased heart valve, the method comprising:

providing apparatus for resecting the diseased heart valve, the apparatus comprising:

a body portion having a proximal end and a distal end, the body portion defining a longitudinal axis from the proximal end to the distal end thereof, and the body portion defining an opening at the distal end;

a grasping tool being selectively positionable within the body portion along the longitudinal axis from a first position to a second position, the grasping tool being configured within the body portion in the first position, the grasping tool extending through the opening at the distal end of the body portion, and the grasping tool being configured to selectively close together a first portion and a second portion so as to selectively grip the diseased heart valve therebetween; and a cutting element disposed within the body portion at a given distance from the opening, the cutting element configured to close together to cut the diseased heart valve therebetween at the given distance from the opening after the grasping tool is withdrawn to a given location between the cutting element and the proximal end of the body portion;

wherein a portion of the diseased heart valve portion cut away from an intact portion of the diseased heart valve is contained within the body portion;

positioning the distal end of the body portion adjacent to the diseased heart valve;

extending the grasping tool through the opening in the body portion to the diseased heart valve portion;

closing the first portion and the second portion of the grasping tool toward one another so as to secure a portion of the diseased heart valve therebetween;

retracting the grasping tool into the body element past the cutting element to the given location between the cutting element and the proximal end of the body portion so as to allow the cutting element to close and cut the portion of the diseased heart valve at the given distance from the opening.

In another form of the present invention, there is provided an apparatus for resecting a diseased heart valve, the apparatus comprising:

a body portion having a first end and a second end in opposition to one another, a lateral wall extending from the first end to the second end, the lateral wall defining an inner surface and an outer surface in opposition to one another, the inner surface and the outer surface defining arcuate surfaces, respectively, and the body portion defining a longitudinal axis from the first end to the second end;

a first handle and a second handle attached to the body portion to extend from the first end thereof and the second end thereof, respectively;

a cutting blade selectively rotatable about the longitudinal axis and disposed adjacent to the inner surface of the body portion;

a set of retaining arms positionably mounted between the second handle and the second end of the body portion, the set of retaining arms being selectively positionable from a contracted state to an expanded state, the contracted state forming a first diameter having a first width in a direction perpendicular to the longitudinal axis of the body portion, the expanded state forming a second diameter having a second width in a direction perpendicular to the longitudinal axis of the body portion, the second width being larger than a first width of the first diameter in the direction perpendicular to the longitudinal axis of the body portion;

a pass-off tool having a proximal end and a distal end, a first attachment device at the distal end thereof, the first attachment device configured to selectively engage the first handle attached to the body portion so as to allow placement of the second handle of the body portion adjacent to the diseased heart valve; and a controller tool having a proximal end and a distal end, a second attachment device at the distal end thereof, the second attachment device configured to selectively engage the second handle attached to the body portion so as to allow positioning of the second end of the body portion adjacent to the diseased heart valve, a cutting blade actuator configured to cause the cutting blade to selectively rotate relative to the longitudinal axis of the body portion, and a retaining arm actuator configured to selectively position the set of retaining arms from the contracted state to the expanded state.

In another form of the present invention, there is provided a method for resecting a diseased heart valve, the method comprising:

providing apparatus for resecting a diseased heart valve, the apparatus comprising:

a body portion having a first end and a second end in opposition to one another, a lateral wall extending from the first end to the second end, the lateral wall defining an inner surface and an outer surface in opposition to one another, the inner surface and the outer surface defining arcuate surfaces, respectively, and the body portion defining a longitudinal axis from the first end to the second end thereof;

a first handle and a second handle attached to the body portion to extend from the first end thereof and the second end, respectively;

a cutting blade selectively rotatable about the longitudinal axis and disposed adjacent to the inner surface of the body portion;

a set of retaining arms positionably mounted between the second handle and the second end of the body portion, the set of retaining arms being selectively positionable from a contracted state to an expanded state, the contracted state forming a first diameter having a first width in a direction perpendicular to the longitudinal axis of the body portion, the expanded state forming a second diameter having a second width in a direction perpendicular to the longitudinal axis of the body portion, the second width being larger than a first width of the first diameter in the direction perpendicular to the longitudinal axis of the body portion;

a pass-off tool having a proximal end and a distal end, a first attachment device at the distal end thereof, the first attachment device configured to selectively engage the first handle attached to the body portion so as to allow placement of the second handle of the body portion adjacent to the diseased heart valve; and a controller tool having a proximal end and a distal end, a second attachment device at the distal end thereof, the second attachment device configured to selectively engage the second handle attached to the body portion so as to allow positioning of the second end of the body portion adjacent to the diseased heart valve, a cutting blade actuator configured to cause the cutting blade to selectively rotate relative to the longitudinal axis of the body portion, and a retaining arm actuator configured to selectively position the set of retaining arms from the contracted state to the expanded state;

engaging the first handle attached to the body portion with the pass-off tool;

positioning the second handle of the body portion adjacent to the diseased heart valve;

engaging the second handle attached to the body portion with the controller tool;

disengaging the pass-off tool and the first handle from one another;

positioning the second end of the body portion adjacent to the diseased heart valve;

expanding the set of retaining arms with the retaining arm actuator so as to hold the cut portion of the diseased heart valve within the body portion;

rotating the cutting blade relative to the longitudinal axis of the body portion with the cutting blade actuator;

positioning the body portion toward the diseased heart valve with the controller tool so as to cut the diseased heart valve.

In another form of the present invention, there is provided an apparatus for resecting a diseased heart valve, the apparatus comprising:

a cylindrical body portion having a first end and a second end;

a first handle and a second handle attached to the body portion to extend from the first end thereof and the second end thereof, respectively;

a cylindrical cutting blade selectively rotatable about the longitudinal axis and disposed within the body portion;

a set of retaining arms positionably mounted therebetween the second handle and the second end of the body portion, the set of retaining arms being selectively positionable from a contracted state to an expanded state, the contracted state forming a first diameter having a first width in a direction perpendicular to the longitudinal axis of the body portion, the expanded state forming a second diameter having a second width in a direction perpendicular to the longitudinal axis of the body portion, the second width being larger than a first width of the first diameter in the direction perpendicular to the longitudinal axis of the body portion.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like elements and further wherein:

FIGS. 13-17 are schematic views of preferred embodiments of the present invention for a punch configured for an aortic approach to a diseased valve;

FIGS. 23-32 are schematic views of an expandable resector views of an expandable resector with three arms, in which one of the arms carries a cutting device;

FIGS. 38-49 are schematic views of a preferred embodiment of the present invention including an expandable blade resector delivered through a catheter;

FIGS. 61-63 are schematic views of a preferred embodiment of the present invention including an offset cutter;

FIGS. 77-79 are schematic views of a preferred embodiment of the invention including a gripper cutter having a pair of graspers and a cutting element;

DETAILED DESCRIPTION OF THE PREFERRED EMBODIMENTS

The present invention can be used to implant a variety of prostheses into the arterial system or left side of the heart. The prosthesis used in the preferred embodiment is an aortic valve prosthesis. Alternatively, the prosthesis may comprise, but is not limited to, a cylindrical arterial stent, an arterial prosthesis or graft, a ventricular assist device, a device for the treatment of heart failure such as an intraventricular counterpulsation balloon, chordae tendinae prostheses, arterial filters suitable for acute or chronic filtration of emboli from the blood stream, arterial occlusion devices and the like.

For clarity of illustration, the present invention will hereinafter be discussed in the context of implanting an aortic valve prosthesis.

It should also be appreciated that the present invention may be practiced either "on-pump" or "off-pump". In other words, the present invention may be performed either with or without the support of cardiopulmonary bypass. The present invention also may be performed either with or without cardiac arrest.

Figure 1:
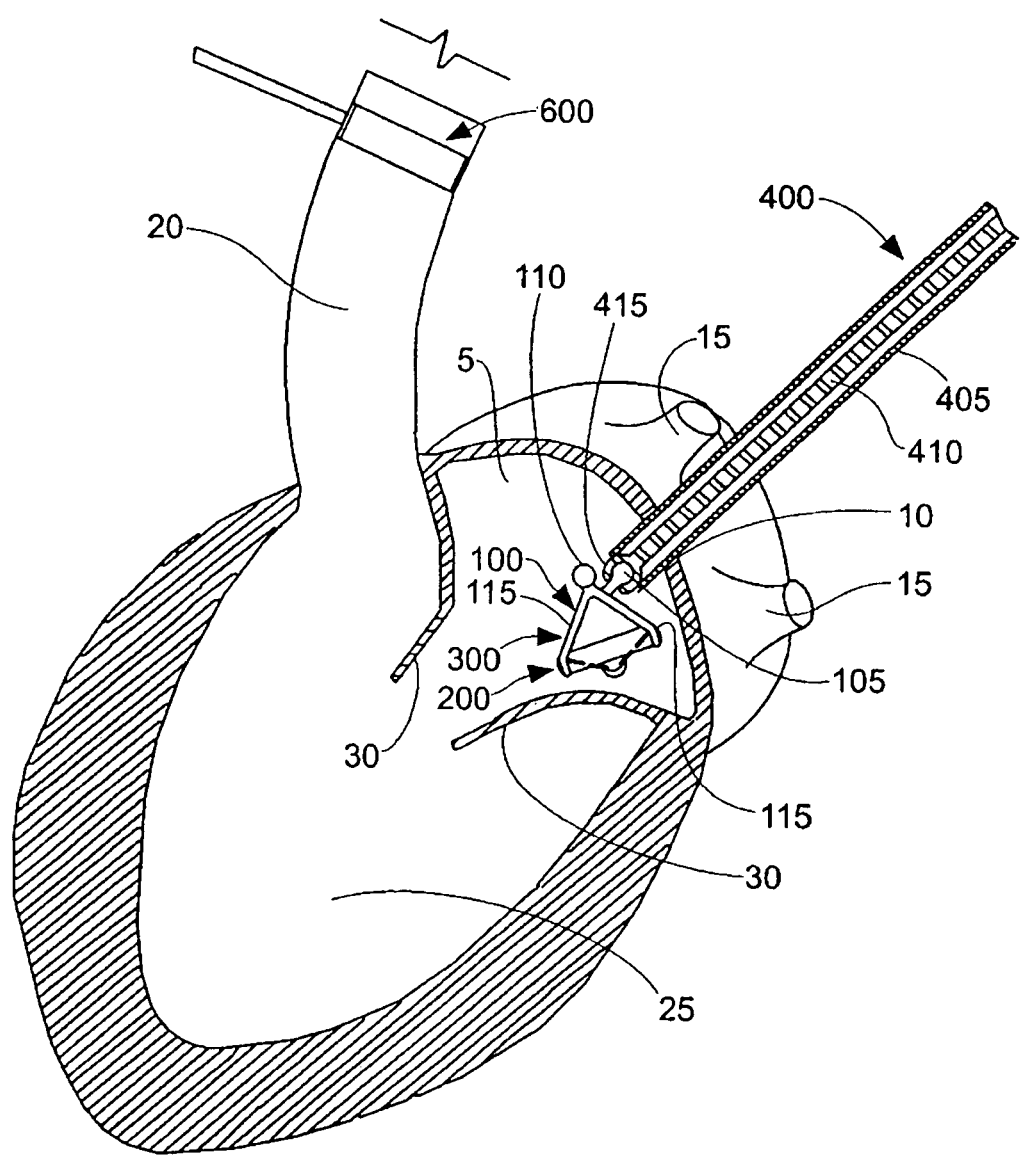
FIG. 1 is a schematic side view showing the introduction of a valve prosthesis and prosthesis holding apparatus into the left atrium of the heart, through an atriotomy, using a first manipulation instrument.

Looking now at FIG. 1, there is shown an exemplary embodiment of the present invention. A prosthesis holding apparatus 100 is secured to a prosthetic valve 200 so as to form a temporary prosthetic assembly 300. A first manipulation instrument 400 is secured to a first manipulation mount 105 formed on prosthesis holding apparatus 100, whereby temporary prosthetic assembly 300 may be moved about by first manipulation instrument 400. Temporary prosthetic assembly 300 has been positioned in left atrium 5 by passing first manipulation instrument 400 through atriotomy 10. Alternatively, the temporary prosthetic assembly 300 could be passed into the left atrium 5, using first manipulation instrument 400, through any of the pulmonary veins 15 (not shown). And in another form of the invention, temporary prosthesis assembly 300 could be passed into the left atrium by first passing the assembly into the right atrium via an atriotomy, and then into the left atrium through an incision made in the interatrial septum.

Prosthetic valve 200 is preferably a conventional mechanical aortic valve of the sort well known in the art, although other forms of valve prostheses may also be used.

In one preferred form of the invention, first manipulation instrument 400 functions by virtue of the relative motion of an outer cannula 405 relative to an inner grasper 410. More particularly, inner grasper 410 has an elastically deformable distal gripper 415 which is open when the gripper is outside of outer cannula 405. However, when deformable gripper 415 is pulled at least partially into or against outer cannula 405, gripper 415 is elastically deformed into a closed position, whereby it may grip an object, e.g., first manipulation mount 105 formed on prosthesis holding apparatus 100. First manipulation instrument 400 is shown in FIG. 1 in its closed position, wherein deformable gripper 415 is closed about first manipulation mount 105, such that prosthesis holding apparatus 100, and hence the entire temporary prosthetic assembly 300, is held secured to the distal end of first manipulation instrument 400.

The specific embodiment of first manipulation instrument 400 shown in FIG. 1 is presented as an illustrative example only, and is not intended to limit the scope of the present invention. Many other arrangements may be used for releasably gripping first manipulation mount 105 formed on prosthesis holding apparatus 100. Furthermore, first manipulation mount 105 may itself have many potential shapes and properties to enable releasable attachment to first manipulation instrument 400. Other possible configurations for releasably securing first manipulation mount 105 to first manipulation instrument 400 include, but are not limited to, opposing magnet poles in the mount and instrument, adhesives, a press fit between mount and instrument, threaded couplings, suture loops, a balloon or balloons expanded within a mating cavity, collapsible barbs, etc. For the purposes of the present invention, the important point is that some arrangement be provided for releasably securing the prosthesis holding apparatus (and hence the prosthetic valve) to a manipulation instrument.

Still looking now at FIG. 1, first manipulation instrument 400 is shown as having a long axis that extends outside of the heart, with first manipulation instrument 400 being straight along that axis. However, it should also be appreciated that first manipulation instrument 400 may, alternatively, be formed with a curve at one or more location along this length. Furthermore, first manipulation instrument 400 may be constructed so as to allow articulation at the distal end, the proximal end, or both, or at any point therebetween. In addition, first manipulation instrument 400 may be formed either entirely rigid or substantially flexible, along all or part of its length.

First manipulation instrument 400 is also shown as having a relatively small dimension perpendicular to its long axis. This configuration allows atriotomy 10 to be reduced in size after the passage of temporary prosthetic assembly 300 into left atrium 5. This perpendicular dimension may be constant or varied along the long axis of first manipulation instrument 400.

The specific embodiment of the prosthesis holding apparatus 100 shown in FIG. 1 is presented as an illustrative example only, and is not intended to limit the scope of the present invention. Many other arrangements may be used for releasably gripping prosthetic valve 200 and for providing first manipulation mount 105, as well as providing a second manipulation mount 110 that will be discussed below. In FIG. 1, first manipulation mount 105 and second manipulation mount 110 are shown as spherical additions to struts 115 extending away from prosthetic valve 200. These spheres are intended to fit, respectively, within the deformable gripper 415 of first installation instrument 400 and the deformable gripper 515 of a second installation instrument 500 (discussed below). First manipulation mount 105 and/or second manipulation mount 110 could, alternatively, be indentations within a portion of male or female threaded extensions from, magnetized surfaces of, slots or holes in or through, prosthesis holding apparatus 100, etc. Furthermore, first manipulation mount 105 and/or second manipulation mount 110 could be portions of the struts 115 extending away from prosthetic valve 200, where those portions may be either reduced or enlarged in dimension relative to neighboring portions of the struts. Many other constructions may also be used to form first manipulation mount 105 and second manipulation mount 110. For the purposes of the present invention, the important point is that some arrangement be provided for releasably securing the prosthesis holding apparatus (and hence the prosthetic valve) to manipulation instruments.

Still looking now at FIG. 1, it will be appreciated that the native aortic valve has been removed. Removal of the native aortic valve is not a necessary element of the present invention, but may be incorporated into the preferred method. Removal of the native aortic valve may be accomplished either before or after passage of the temporary prosthetic assembly 300 into left atrium 5.

When the methods and devices of the present invention are employed during an off-pump valve replacement procedure, it may be beneficial to provide temporary valves and/or filters in the arterial system, downstream of the site of the native aortic valve. Thus, for example, in FIG. 1 there is shown a temporary valve 600 (not shown in the remaining figures) which may be used to support cardiac function during and following removal of the diseased cardiac valve. Temporary valve 600 is shown positioned in aorta 20. Alternatively, temporary valve 600 may be positioned in the aortic arch or the descending aorta. In addition, temporary valve 600 may incorporate a filter therein to mitigate the risks of embolic complications. Alternatively, a separate filter may be employed within the aorta and/or the branch arteries extending therefrom.

Figure 2:
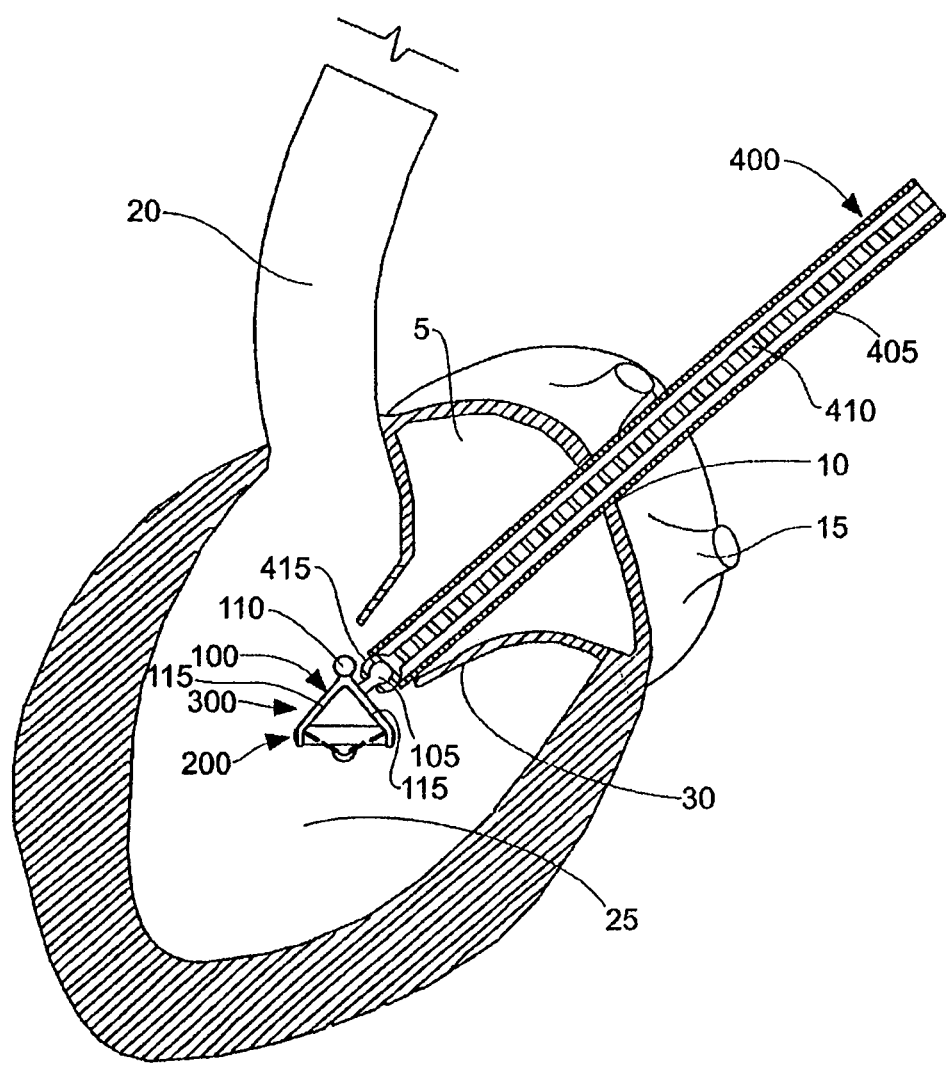
FIG. 2 is a schematic side view showing passage of the apparatus of FIG. 1 from the left atrium, through the mitral valve, and into the left ventricle.

FIG. 2 shows first manipulation instrument 400 being used to manipulate temporary prosthetic assembly 300 (and hence prosthetic valve 200) into left ventricle 25 through mitral valve 30. After temporary prosthetic assembly 300 has passed into left ventricle 25, the first manipulation instrument 400 will continue to traverse mitral valve 30; however, the reduced perpendicular cross-section of first manipulation instrument 400 will cause only minimal disruption of the function of mitral valve 30.

Figure 3:
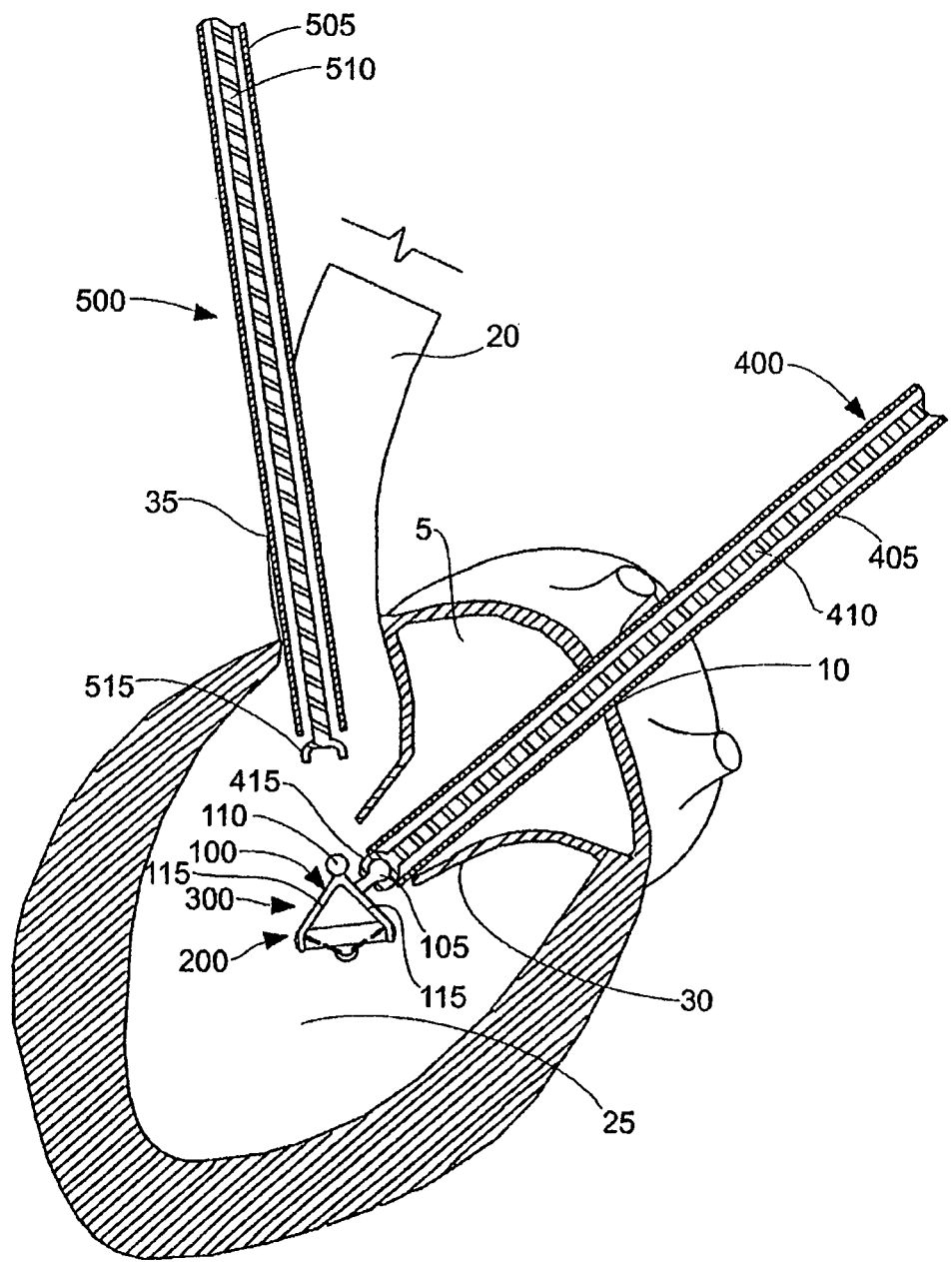
FIG. 3 is a schematic side view showing the introduction of a second manipulation instrument into the left ventricle through an arteriotomy into the arterial system.

FIG. 3 shows the insertion of a second manipulation instrument 500 through the arterial system and into left ventricle 25. Second manipulation instrument 500 is shown being inserted through an incision 35 on aorta 20. Alternatively, second manipulation instrument 500 could be inserted into a central or peripheral artery and than advanced into left ventricle 25. Aortic incision 35 is small relative to the atriotomy 10 formed in left atrium 5.

Bleeding through incision 35 may be readily controlled through a variety of means. These include, but are not limited to, employing a valved or un-valved arterial cannula, a pursestring suture placed around incision 35 and then pulled tight about second manipulation instrument 500, a side-arm graft sewn to aorta 20 that may be constricted about a region of second manipulation instrument 500, the use of a tight fit between a portion of second manipulation instrument 500 and aortic incision 35, etc.

Second manipulation instrument 500 is shown in FIG. 3 as being of the same form and function of first manipulation instrument 400. Again, outer cannula 505 fits around inner grasper 510, and the relative motion between grasper 510 and cannula 505 can be used to deform gripper 515 between open and closed positions. Alternatively, second manipulation instrument 500 may have any of the variety of other forms and functions described above with respect to first manipulation instrument 400. Furthermore, second manipulation instrument 500 is preferably of a smaller dimension perpendicular to its long axis than first manipulation instrument 400 so as to reduce the risks posed by arteriotomy 35.

Figure 4:
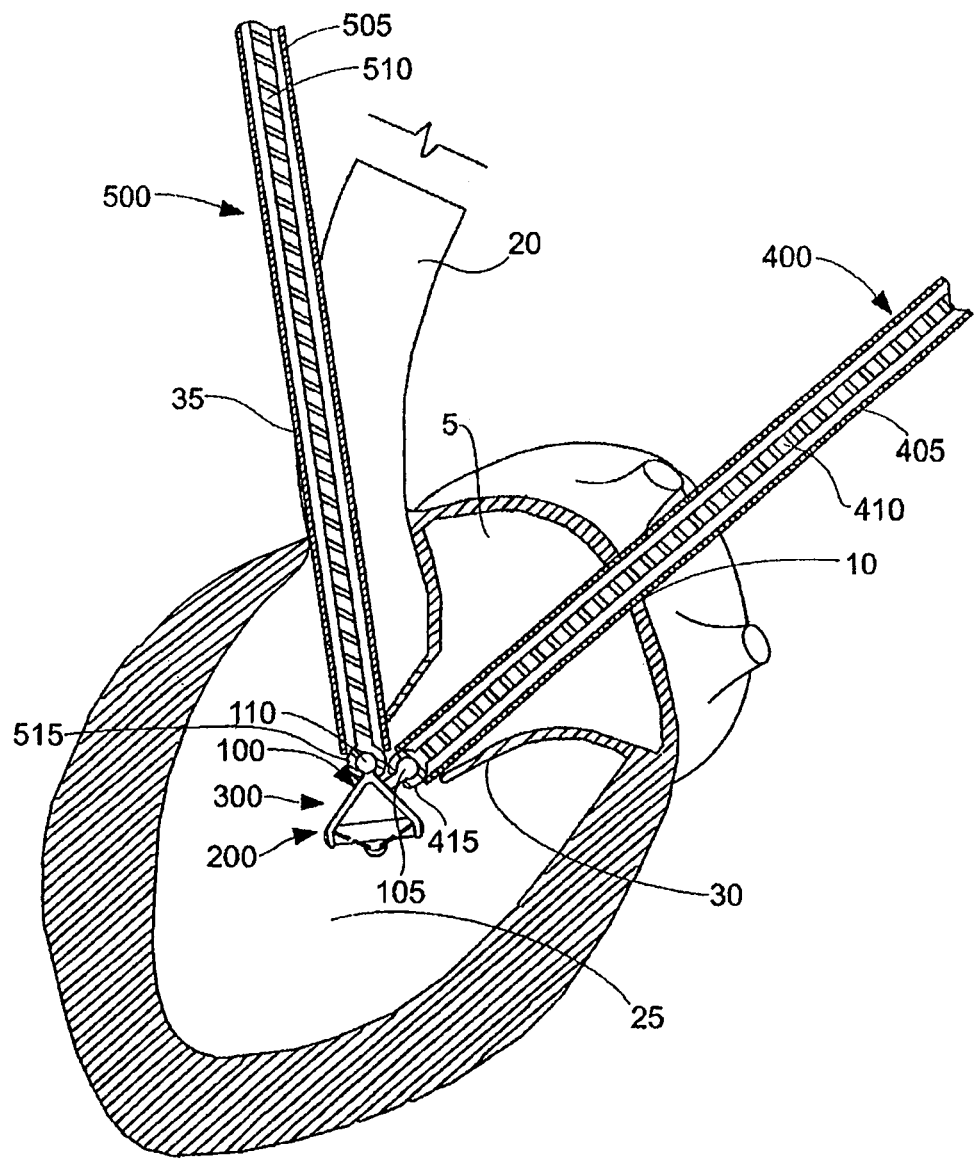
FIG. 4 is a schematic side view showing the second manipulation instrument being attached to the prosthesis holding apparatus while the first manipulation instrument remains secured to the prosthesis holding apparatus.

FIG. 4 shows second manipulation instrument 500 being secured to the second manipulation mount 110 formed on prosthesis holding apparatus 100. This is done while first manipulation instrument 400 is secured to first manipulation mount 105 formed on prosthesis holding apparatus 100, in order that temporary prosthetic assembly 300 will be under control at all times during the "hand-off" between first manipulation instrument 400 and second manipulation instrument 500.

It should be appreciated that the orientation of second manipulation mount 110 is preferably such as to enable the long axis of second manipulation instrument 500 to be substantially perpendicular to the flow area of prosthetic valve 200. This arrangement is particularly helpful when guiding prosthetic valve 200 into its final position within aorta 20 as shown hereafter in FIGS. 6 and 7.

The use of two separate manipulation instruments, and the method of passing valve prosthesis 200 from one to the other, avoids the complex manipulations of valve prosthesis 200 that would be required to position valve 200 within aorta 20 using only a single manipulation instrument introduced through the left atrium. In this respect it should be appreciated that such a "single manipulation instrument" technique has been found to be possible, however, and is best facilitated by using a manipulation instrument capable of bending or articulating at or near the site of its attachment to valve holding apparatus 100. In this respect it has been found that it can be particularly advantageous to provide a manipulation instrument capable of bending or articulating within about 4 cm or so of the point of attachment to valve holding apparatus 100. It has also been found that it can be particularly advantageous for such an articulating instrument to be able to deflect its distal tip by an angle of between about 90 to 180 degrees from the long axis of the first manipulation instrument 400 shown in FIG. 4.

The angular offset of first manipulation mount 105 and second manipulation mount 110 is preferably set to facilitate passage of temporary prosthetic assembly 300 from left atrium 5 to aorta 20 using two substantially straight manipulation instruments, e.g., first manipulation instrument 400 and second manipulation instrument 500. This angle is preferably approximately 45 degrees. However, this angle may also be varied so as to optimize passage of different valve designs or other prostheses using curved, straight or articulating manipulation instruments from various access sites into the left atrium and arterial system. This angle may be fixed or variable on a given prosthesis holding apparatus 100.

Figure 5:
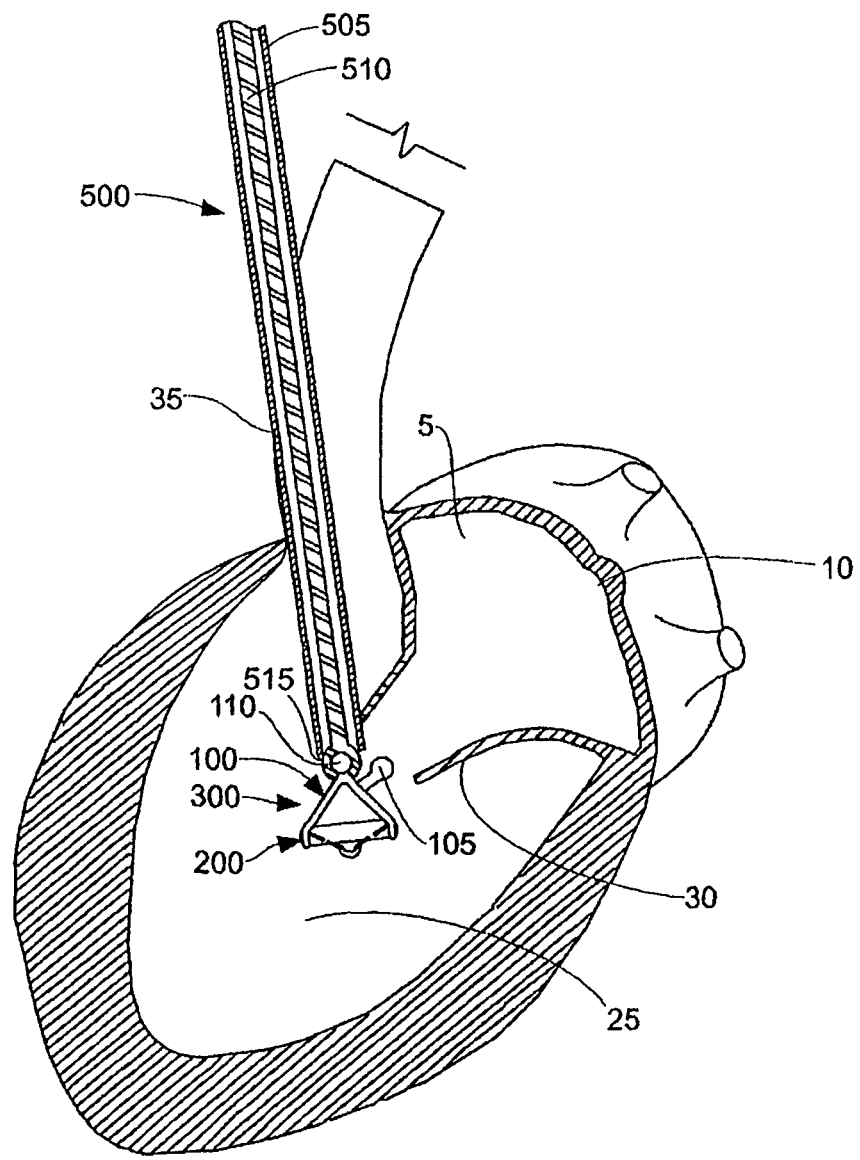
FIG. 5 is a schematic side view similar to that of FIG. 4, except showing the first manipulation instrument being removed from the surgical site while the second manipulation instrument remains secured to the prosthesis holding apparatus.

Once second manipulation instrument 500 is safely secured to second manipulation mount 110, first manipulation instrument 400 may be released from first manipulation mount 105 and removed from left ventricle 5, as shown in FIG. 5. Alternatively, first manipulation instrument 400 may remain secured to prosthesis holding apparatus 100 or prosthetic valve 200 by a flexible tether so as to facilitate re-attachment of first manipulation instrument 400 to valve holding apparatus 100 if necessary.

Figure 6:
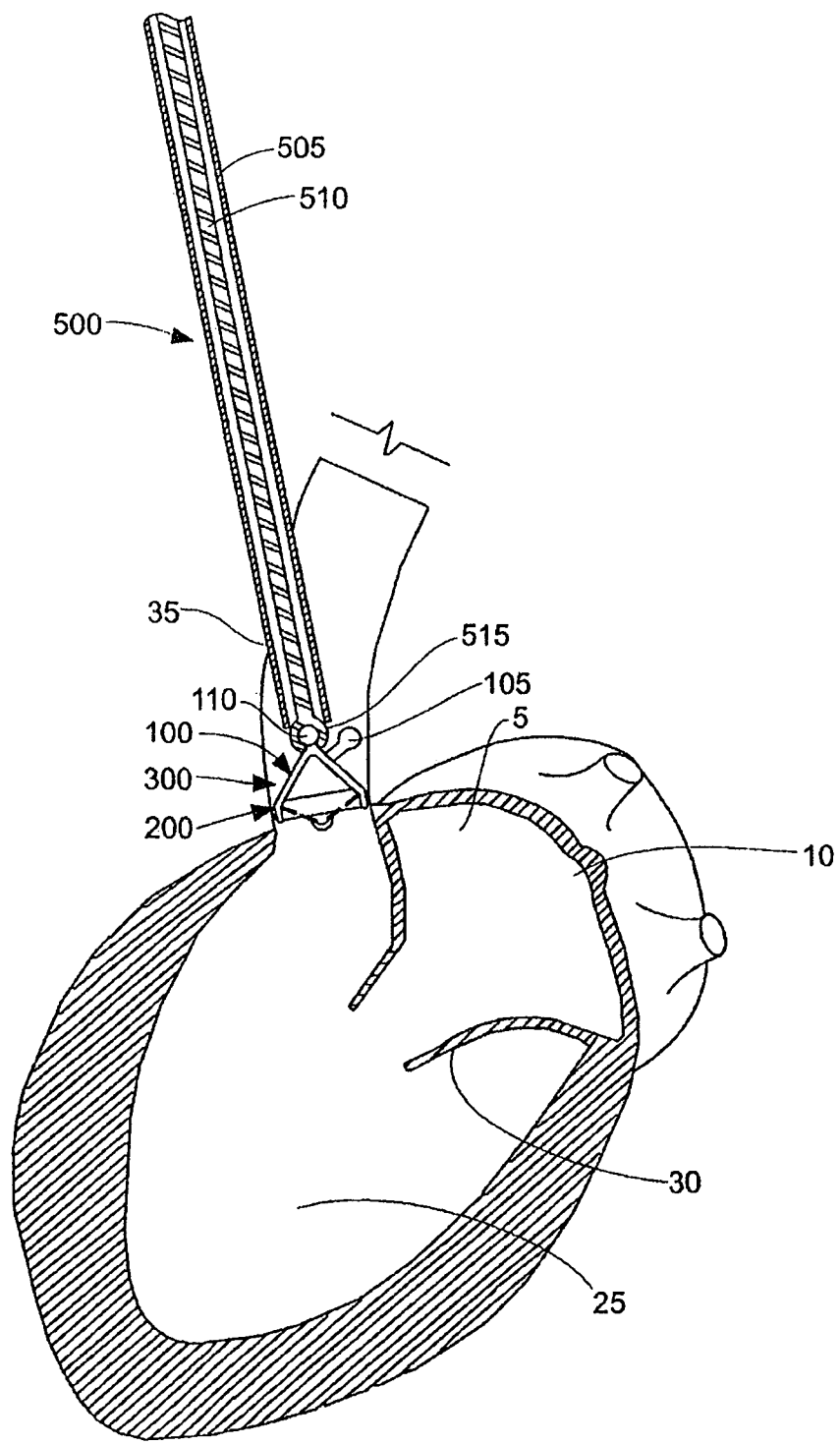
FIG. 6 is a schematic side view showing the second manipulation instrument positioning the prosthetic valve within the aorta prior to fixation.

FIG. 6 shows temporary prosthesis assembly 300 being positioned by second manipulation instrument 500 at a preferred fixation site. This fixation site is preferably upstream of or proximal to the coronary arteries, although this position is not a restrictive requirement of the present invention.

Figure 7:
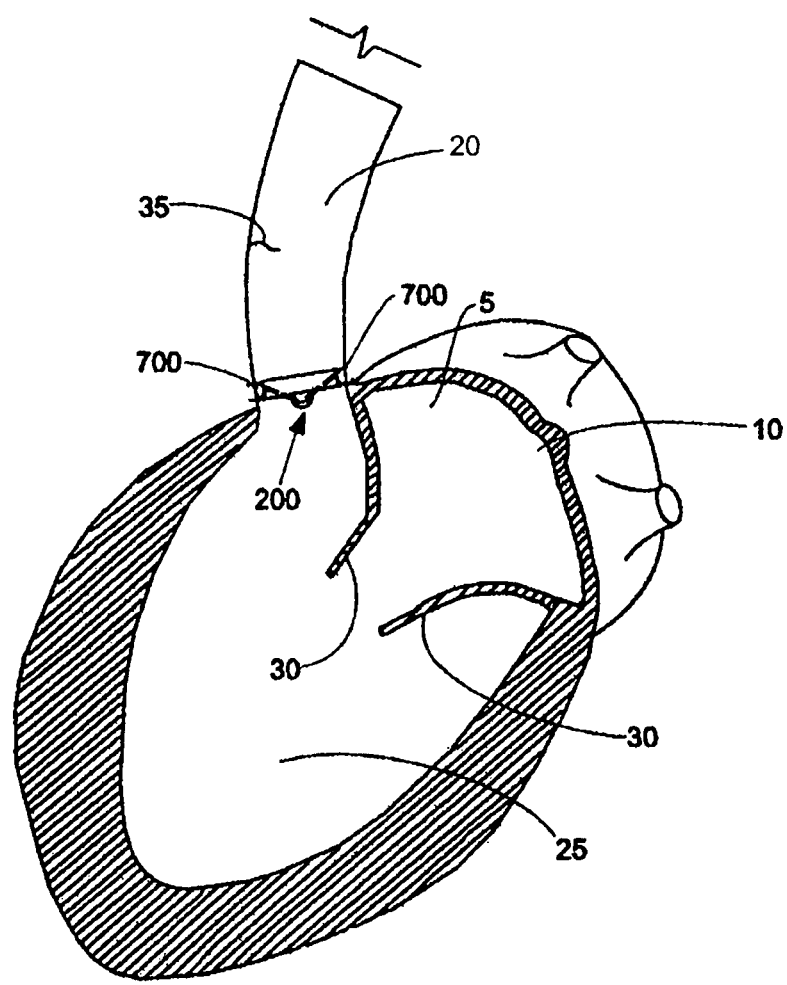
FIG. 7 is a schematic side view showing the prosthetic valve secured to the tissues of the aorta following removal of the second manipulation instrument and prosthesis holding apparatus.

FIG. 7 shows valve prosthesis 200 secured to the walls of aorta 20 and removal of second manipulation instrument 500 and prosthesis holding apparatus 100. In this respect it should be appreciated that prosthesis holding apparatus 100 is preferably wholly or partially flexible, or otherwise collapsible, so as to allow the prosthesis holding apparatus 100 to be collapsed radially and then withdrawn through arteriotomy 35 after prosthesis holding apparatus 100 has been released from prosthetic valve 200. Alternatively, prosthesis holding apparatus 100 may be removed from the vascular system, either partially or entirely, through atriotomy 10 by first manipulation instrument 400, by a tether leading therefrom, or a separate instrument. Of course, in the situation where prosthesis holding apparatus 100 is to be removed via atriotomy 10, the prosthesis holding apparatus 100 should be appropriately mounted to prosthetic valve 200, i.e., prosthesis holding apparatus 100 should be positioned on the atriotomy side of the valve.

In FIG. 7, valve prosthesis 200 is shown secured to aorta 20 using barbs or staples 700. Barbs or staples 700 may be a component of, and/or deployed from, prosthesis holding apparatus 100, and/or valve prosthesis 200, and/or a separate fixation device. Alternatively, barbs or staples 700 may be deployed by a separate instrument inserted through the outer surface of aorta 20, from a remote site in the arterial system, through atriotomy 10 or through some other incision into a cardiac chamber or great vessel.

Figure 8:
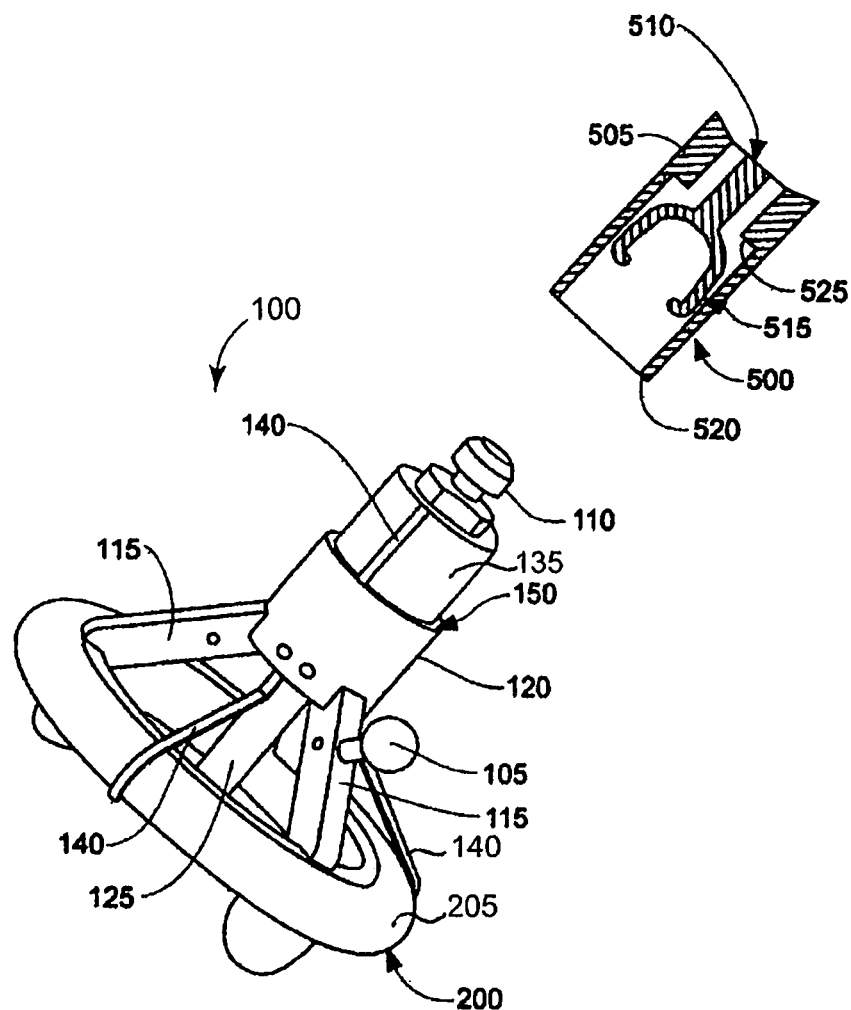
FIGS. 8, 9 and 10 are enlarged schematic views showing a preferred construction for the valve holding apparatus, and for the attachment to, and detachment from, the prosthetic valve.
Figure 9:
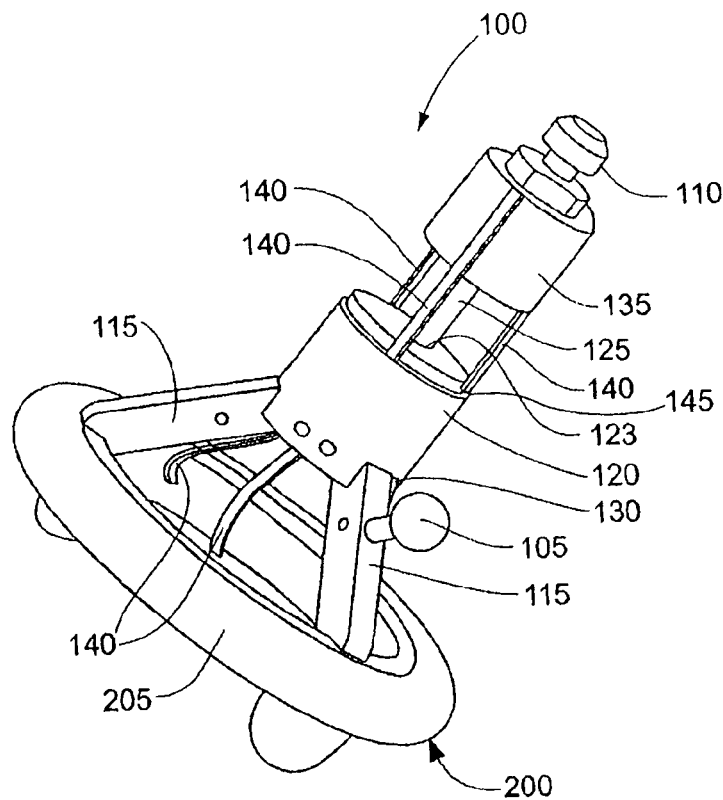
Figure 10:
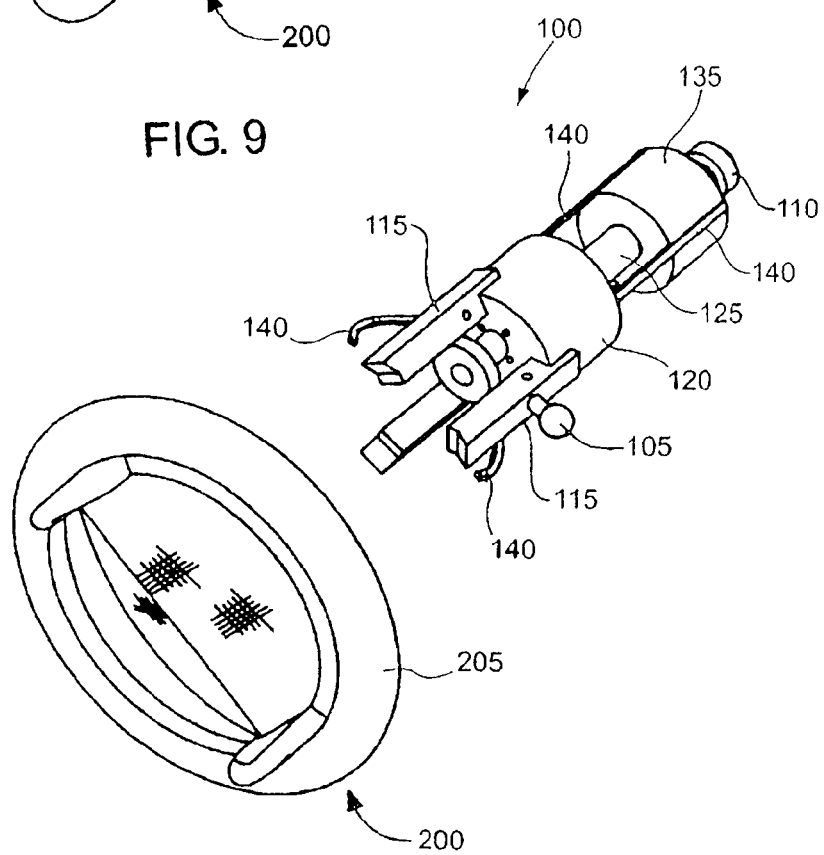

Looking next at FIGS. 8-10, there is shown one preferred configuration for prosthesis holding apparatus 100. More particularly, prosthesis holding apparatus 100 comprises a base 120 having a longitudinal opening 123 (FIG. 9) therein for slidably receiving a rod 125 therethrough. Base 120 also comprises a plurality of side slots 130. Each side slot 130 has a strut 115 pivotally connected thereto. Slots 130 are constructed so that each strut 115 can pivot freely between (i) the position shown in FIGS. 8 and 9, and (ii) the position shown in FIG. 10. A body 135 is mounted on rod 125. A plurality of wire fingers 140 are secured to body 135. Wire fingers 140 extend through holes 145 formed in base 120 and extend around the cuff 205 of prosthetic valve 200. Second manipulation mount 110 is secured to the proximal end of rod 125. First manipulation mount 105 is secured to one of the struts 115. Alternatively, as noted above, first manipulation mount 105 may be formed by a strut 115 itself, provided that first manipulation instrument 400 is appropriately adapted to engage the strut 15 directly.

In use, prosthesis holding apparatus 100 is fit about valve prosthesis 200 so that wire fingers 140 hold valve cuff 205 to struts 115. Prosthesis holding apparatus 100 is then engaged by first manipulation instrument 400, using first manipulation mount 105, and moved into and through right atrium 5, through mitral valve 30 and into left ventricle 25. Then second manipulation tool 500, comprising outer cannula 505 and inner grasper 510 having the deformable gripper 515, engages second manipulation mount 110. The distal tip 520 of outer cannula 505 is placed against edge 150 of base 120 and gripper 515 is drawn proximally-within outer cannula 505 until deformable gripper 515 engages shoulder 525, whereupon prosthesis holding apparatus 100 (and hence prosthetic valve 200) will be mounted to second manipulation tool 500. Second manipulation tool 500 is then used to maneuver temporary prosthetic assembly 300 into position, whereupon the valve's cuff 205 is secured to the side wall of the aorta, e.g., with barbs, staples, suture, etc. Then prosthesis holding apparatus 100 is detached from prosthetic valve 200 by pulling inner grasper 510 proximally relative to outer cannula 505 so that wire fingers 140 are pulled free from valve cuff 205 (FIG. 9), whereby to free prosthesis holding apparatus 100 from the prosthetic valve 200. Then second manipulation instrument 500 is withdrawn out aorta 20 and arteriotomy 35, with struts 115 folding inwardly (FIG. 10) so as to pass through the arteriotomy. Struts 115 can be adapted to fold inwardly through engagement with the walls of the arteriotomy 35 or, alternatively, additional means (such as springs, cams, etc.) can be provided to fold struts 115 inwardly.

Figure 11:
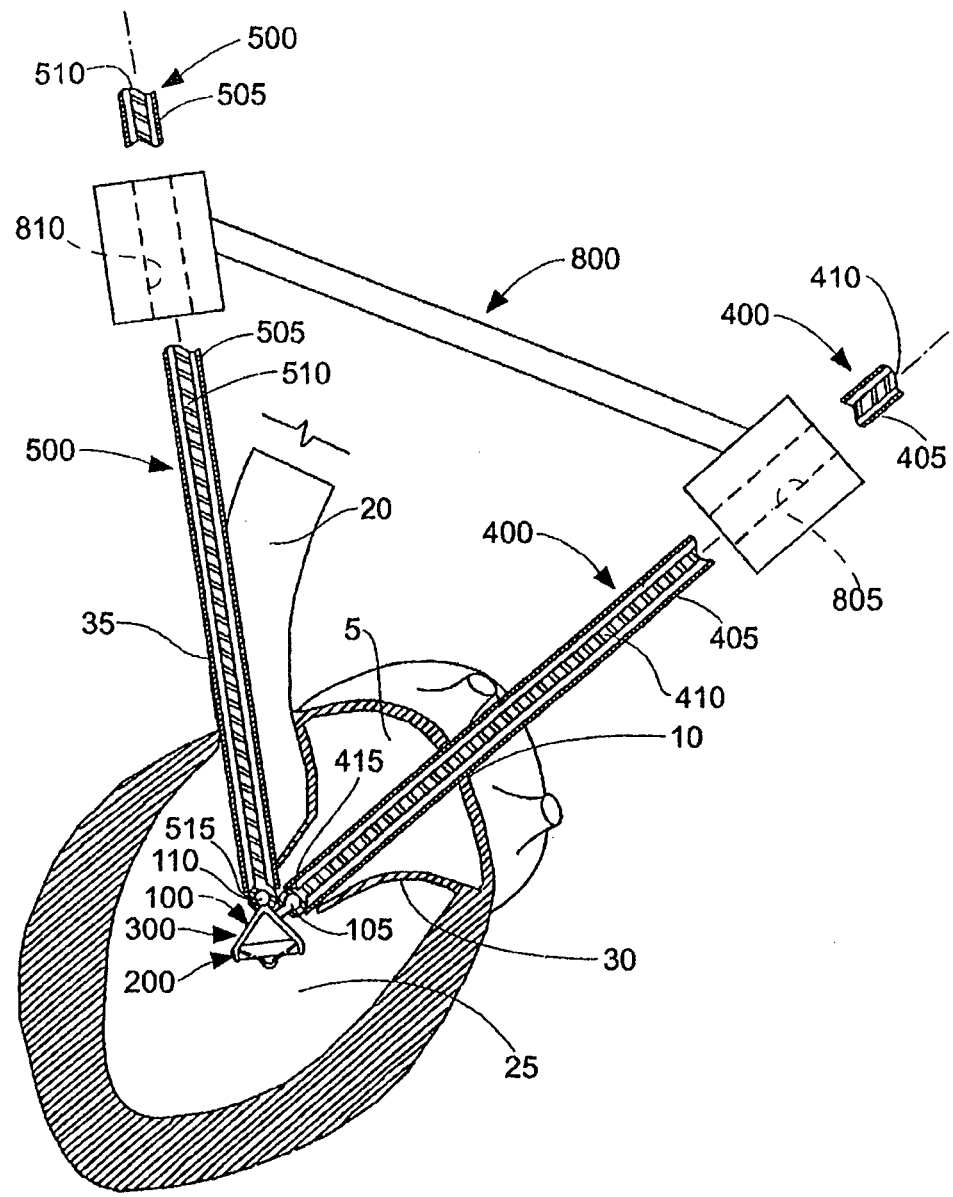
FIG. 11 is a schematic view showing a guide for guiding the second manipulation instrument relative to the first manipulation instrument such that the second manipulation instrument will be aimed directly at the second manipulation mount when the first manipulation mount is secured to the first manipulation instrument.

In practice, it has been found that it can sometimes be difficult to locate second manipulation mount 110 with second manipulation instrument 500 so as to "hand off" temporary prosthesis assembly 300 from first manipulation instrument 400 to second manipulation instrument 500. This can be particularly true where the procedure is to be conducted "off-pump", i.e., without stopping the heart. To this end, and looking now at FIG. 11, there is shown a guide 800 for guiding second manipulation instrument 500 relative to first manipulation instrument 400 such that second manipulation instrument 500 will be aimed directly at second manipulation mount 110 when first manipulation mount 105 is secured to first manipulation instrument 400. More particularly, guide 800 comprises a first passageway 805 for slidably receiving first manipulation instrument 400, and a second passageway 810 for slidably receiving second manipulation instrument 500. Passageways 805 and 810 are oriented so that second manipulation instrument 500 will be aimed directly at second manipulation mount 110 when temporary prosthesis assembly 300 is held by first manipulation instrument 400 engaging first manipulation mount 105.

In accordance with the present invention, it is also possible to enter the left atrium other than through an exterior wall of the left atrium. Thus, for example, it is possible to introduce the prosthetic valve through an opening in an exterior wall of the right atrium, pass the prosthetic valve through an incision in the interatrial septum and across to the left atrium, and then advance the prosthetic valve to its implantation site via the mitral valve and the left ventricle.

As noted above, the manipulation instrument(s) do not need to take the form of the installation instrument 400 or 500. It is also possible to deliver the prosthetic valve to its implant site using a guidewire and a pusher tool riding on the guidewire.

Thus, for example, in an alternative preferred embodiment, a wire, a catheter, a tube or any other filament can be placed from the left atrium, through the ventricle and into the arterial system, over (or through) which a prosthesis or device can be advanced (pushed or pulled). As an example, a catheter with a balloon can be placed through an incision in the left atrial wall. The balloon can be inflated and this catheter can then be "floated" along the flow of blood across the mitral valve, into the left ventricle, and out into the arterial system. At that point the catheter can be grasped by an instrument placed through a small incision in the aorta or passed into the aorta by means of a remote vessel such as the femoral artery. At this point, the prosthesis or device can be mounted onto the catheter and either be pushed (or pulled) over the catheter into position. This procedure can be similarly performed by the use of a wire or other filament structure. Also, a tube could be employed, with the prosthesis or device being advanced within the tube.

Figure 12:
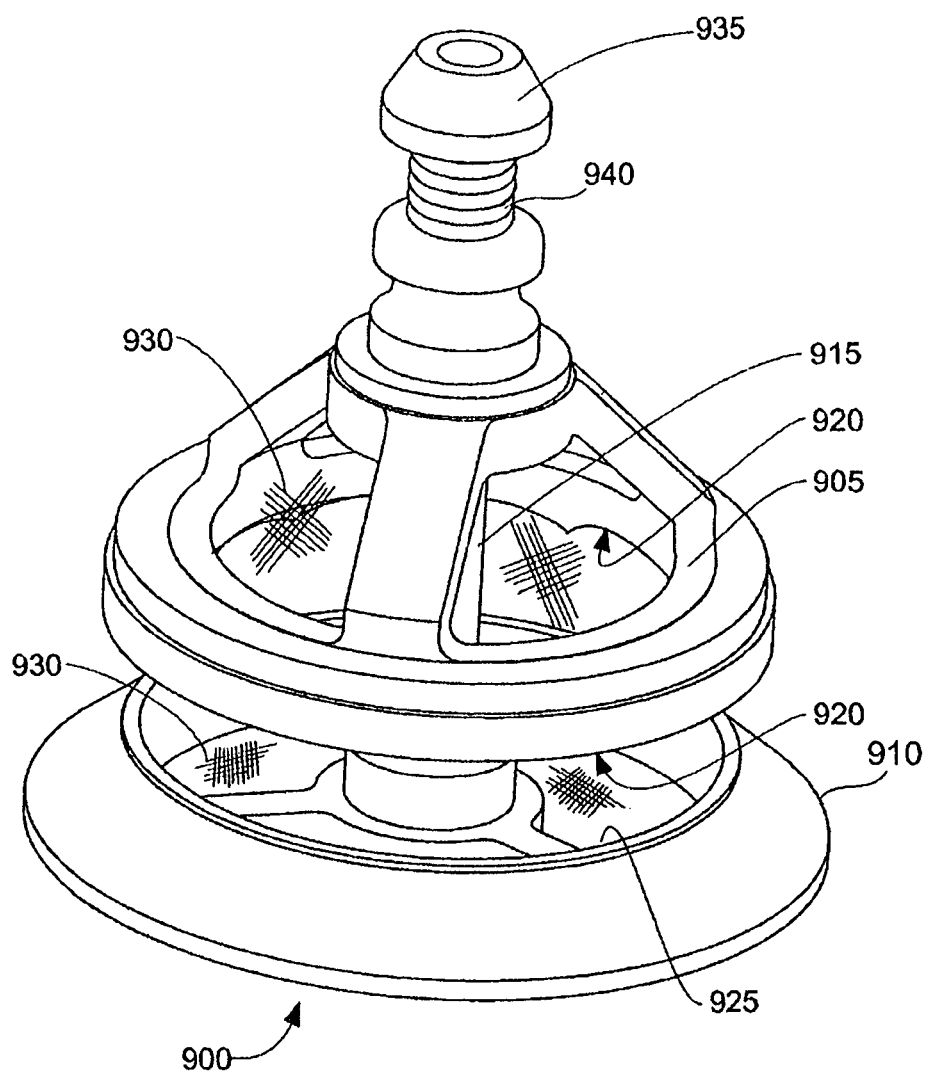
FIG. 12 is a perspective view of a preferred embodiment of the present invention for a punch configured for a left ventrical approach to a diseased valve.
Figure 91:
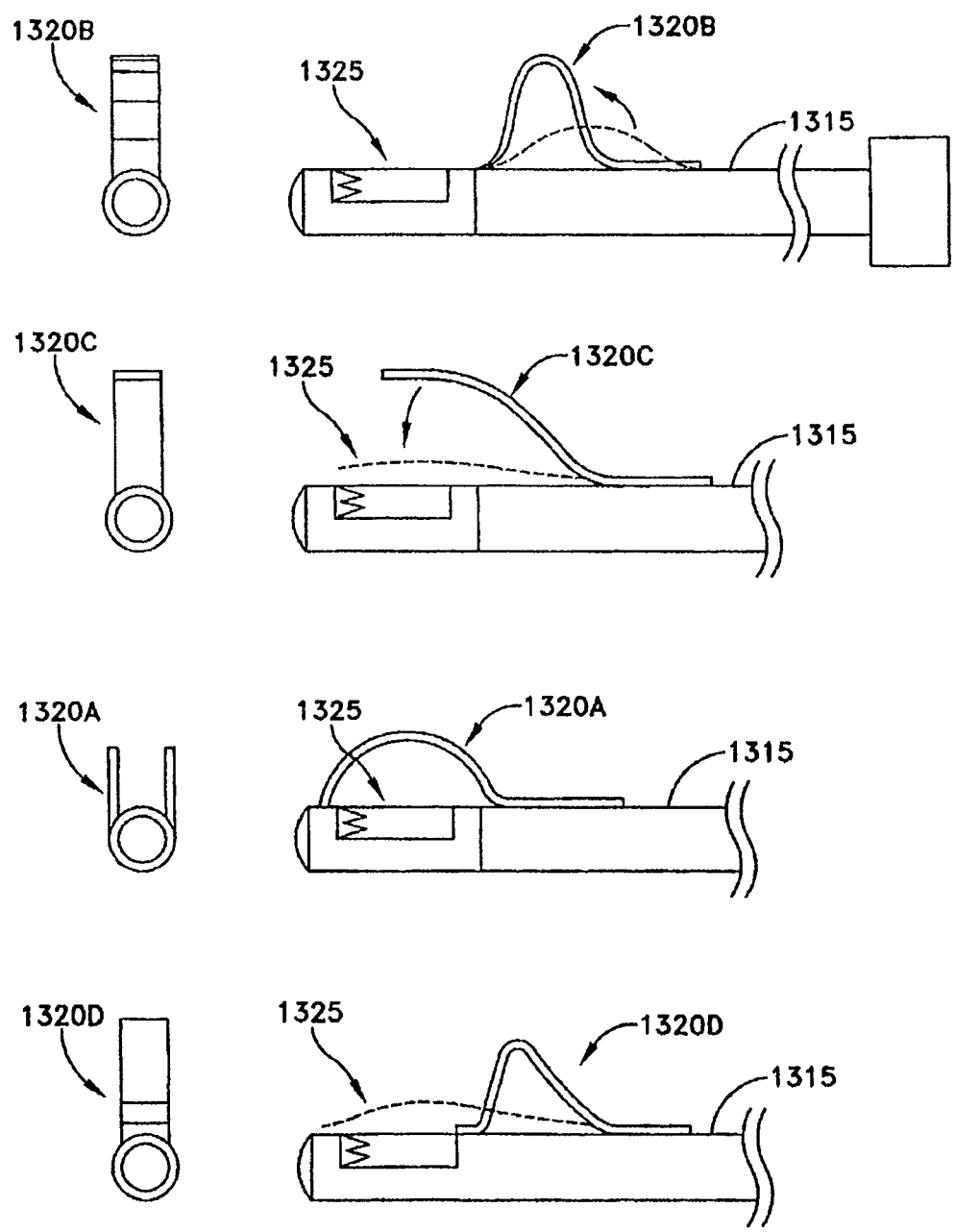
FIG. 91 is a schematic view of a resection tool having several different types of protective guides.
Figure 92:
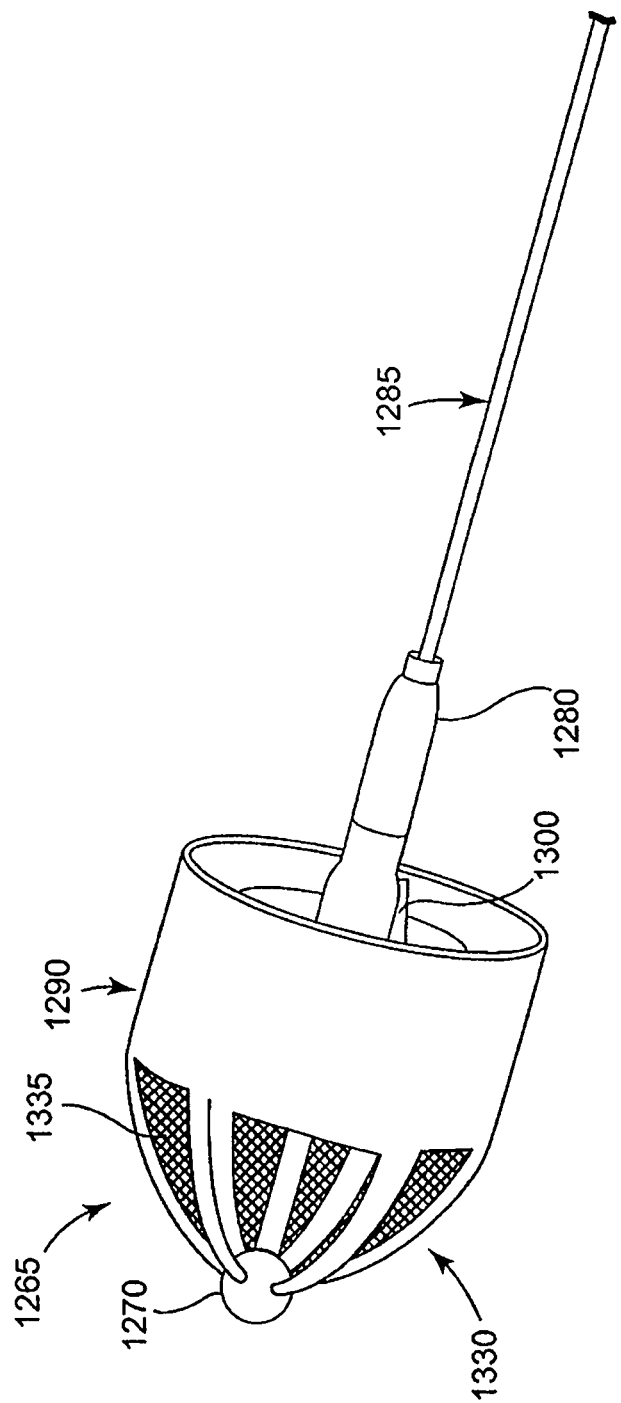
FIGS. 92-101 are schematic views of a preferred embodiment of the present invention including a valve cutter and resector for use with a left ventrical approach, the valve cutter and resector having an umbrella covered by filter material.
Figure 93:
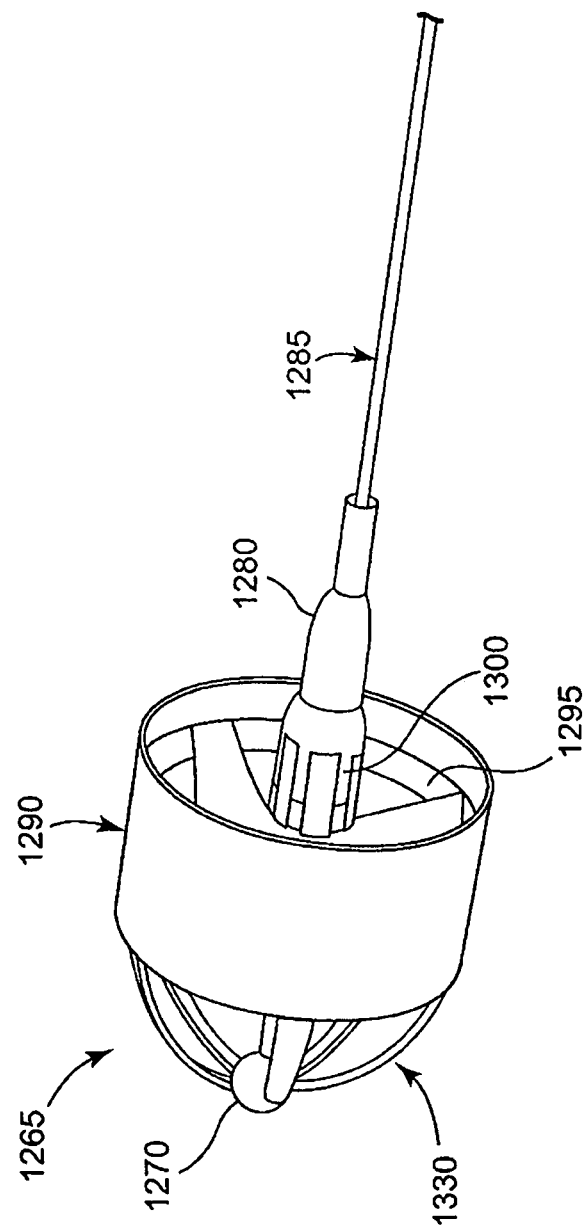
Figure 94:
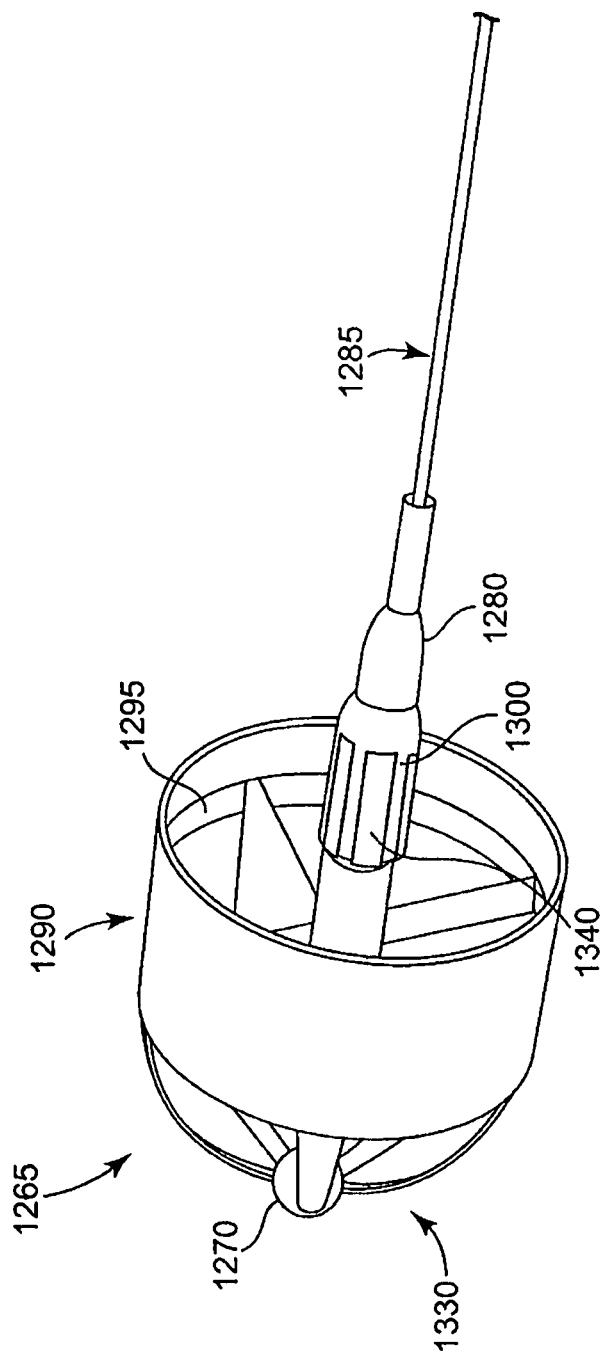
Figure 95:
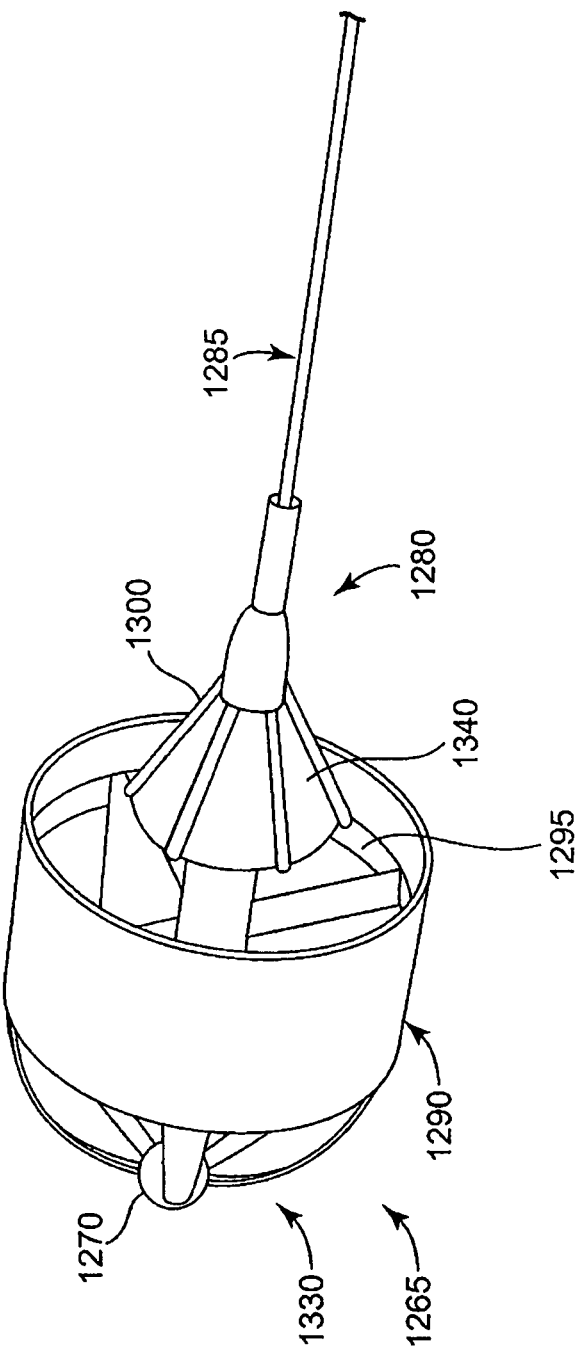
Figure 96:
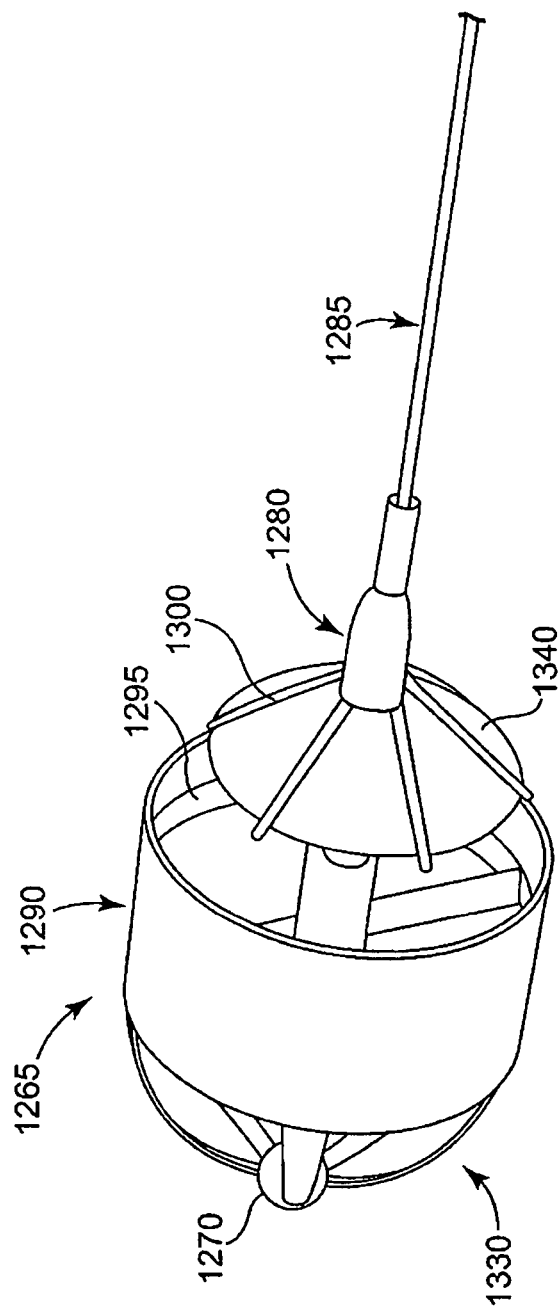
Figure 97:
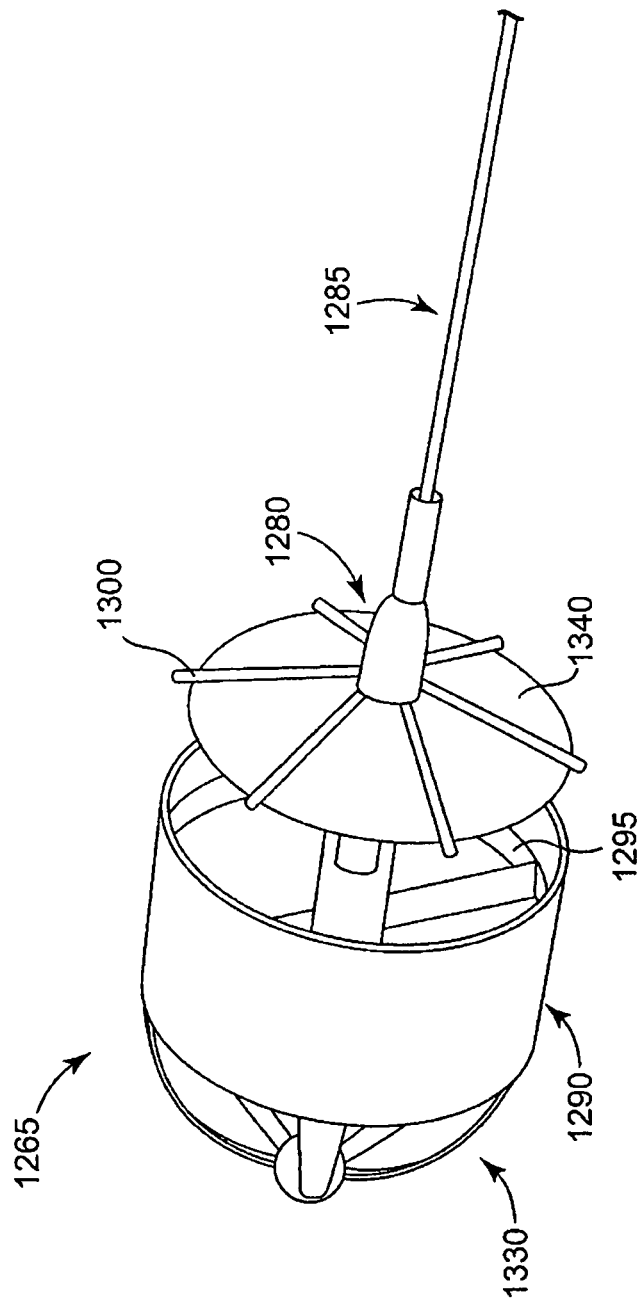
Figure 98:
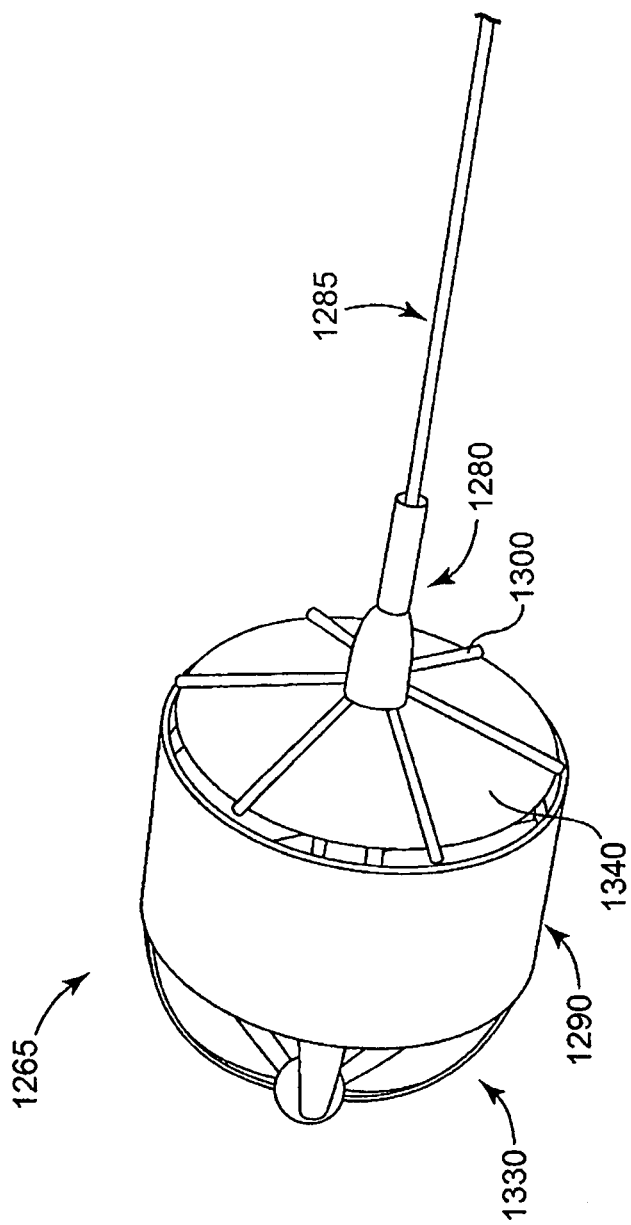
Figure 99:
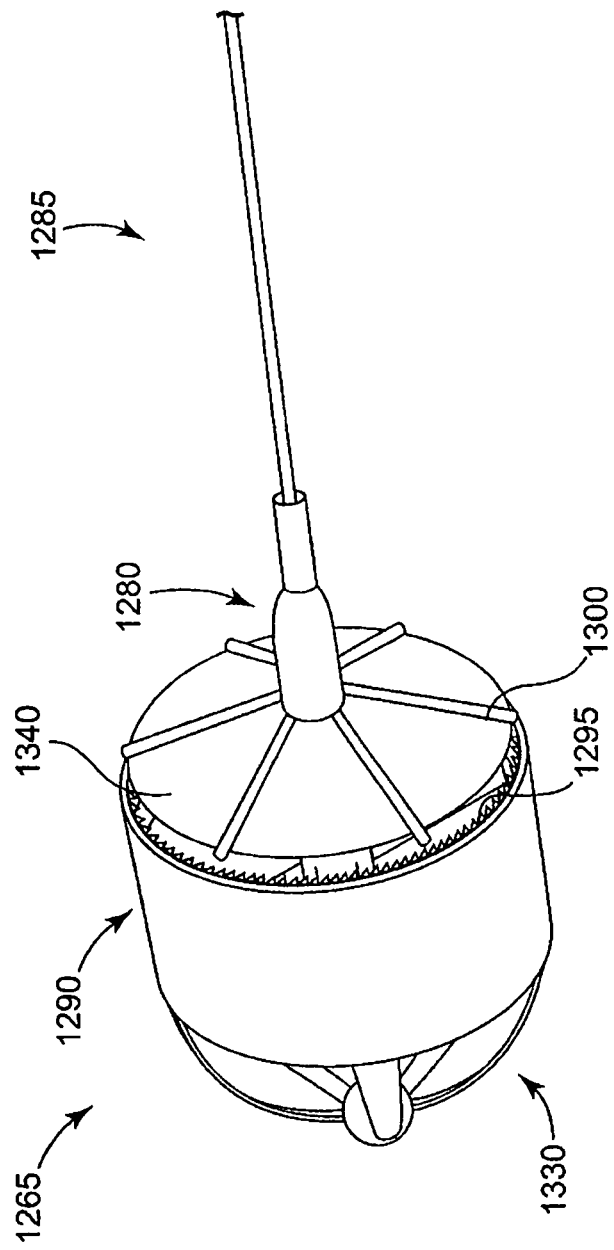
Figure 100:
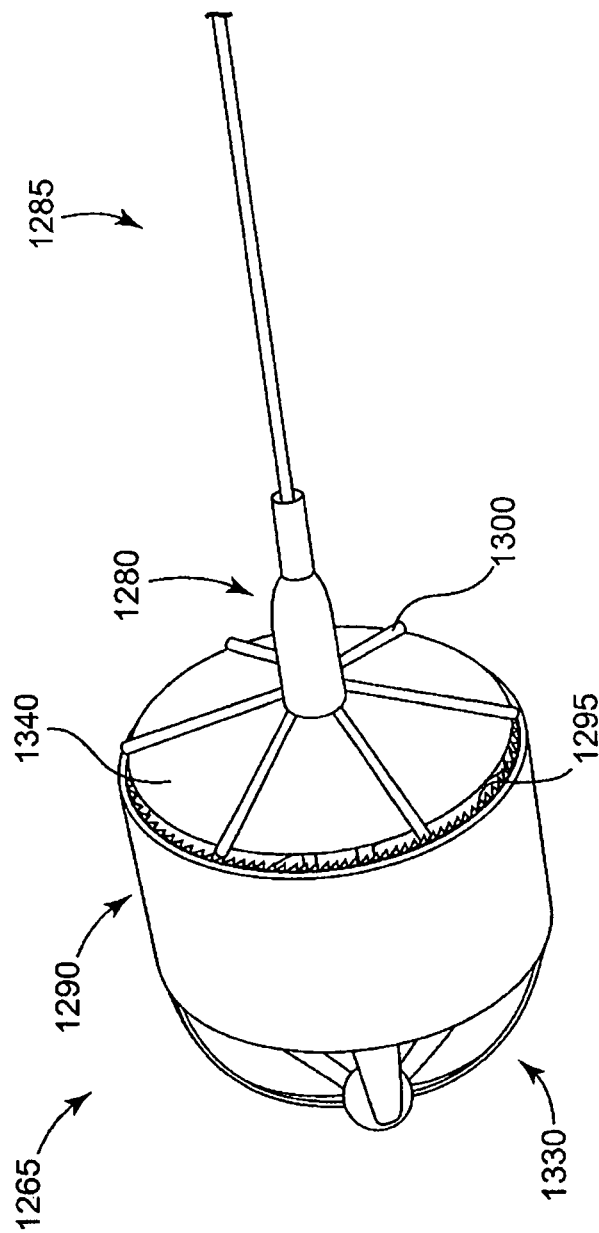
Figure 101:
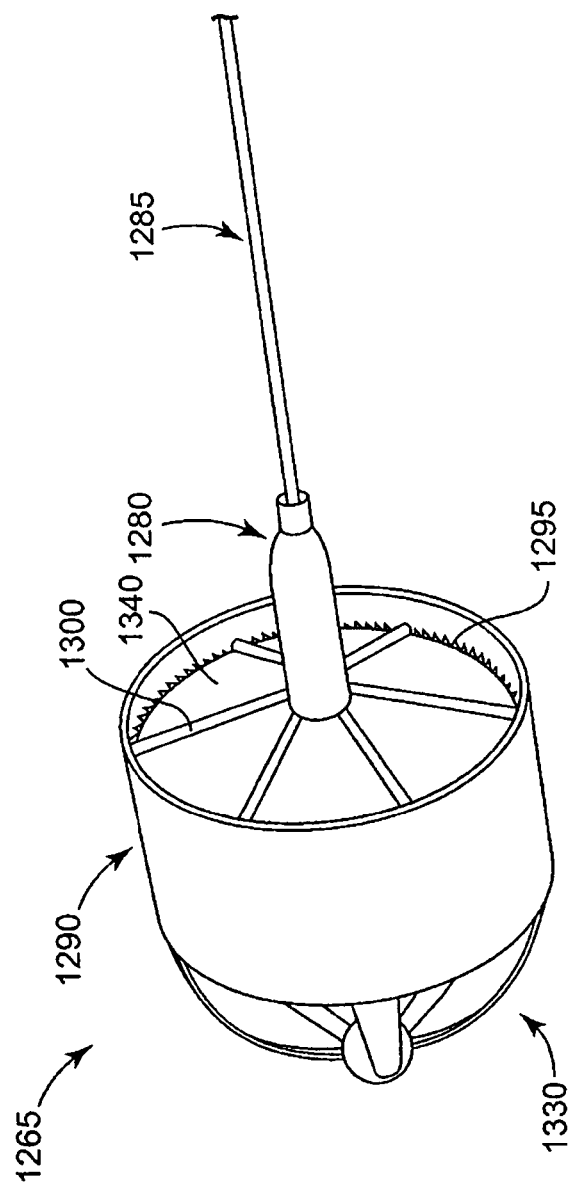

Looking now at FIGS. 12-91, several preferred embodiments of the present invention are shown for removing a diseased valve without causing stroke or other ischemic events that might result from the liberation of particulate material. Valve resection may be necessary prior to valve replacement of a diseased valve, such as a stenotic valve, which will not open, or an insufficient valve, which will not close. In addition, the diseased valve may also be calcified or have a torn leaflet. In some of the preferred embodiments of the present invention, a crushing force is delivered to the diseased valve so as to displace the diseased valve prior to implantation of a replacement valve. However, adequate displacement of the diseased valve prior to implantation of a replacement valve may not be possible due to calcification or displacement alone may not allow the desired placement of the replacement valve. Several preferred embodiments of the present invention are configured to cut away and remove the diseased valve, rather than only crush it, so as to allow implantation of the replacement valve at a desired location.

Referring now to FIG. 12, a valve punch 900 is shown having a first frame member 905 and a second frame member 910 positioned relative to one another by an adjustable connector 915. In a preferred embodiment of the present invention, first frame member 905 holds a blade 920 configured to form a closed perimeter and with its cutting surface facing toward second frame member 910. Second frame member 910 is configured with a corresponding cutting surface 925 facing toward the blade 920.

In use, punch 900 is positioned at a diseased valve (not shown) with adjustable connector 915 operated to space first frame member 905 and second frame member 910 apart from one another so as to receive at least a portion of the diseased valve (not shown) therebetween. Next, adjustable connector 915 is operated so as to close first frame member 905 and second frame member 910 toward one another. This action causes blade 920 to move past cutting surface 925 so as to sever the portion of the diseased valve (not shown) therebetween. Punch 900 may be removed with the resected valve contained between first frame member 905 and second frame member 910. Punch 900 may be configured for either an approach to the valve through the aorta, referred to as an aortic approach, or an approach to the valve through the left ventricle of the heart, referred to as a left ventrical approach.

In a preferred embodiment of the present invention, and still referring to FIG. 12, punch 900 is configured to allow blood flow through first frame member 905 and second member 910. Screen portions 930 may be provided on first frame member 905 and second frame member 910 so as to contain small pieces of the resected valve, which may otherwise be carried away.

Adjustable connector 915 of punch 900 is preferably configured with a handle 935 for opening and closing first frame portion 905 and second frame portion 910 relative to one another. A spring 940 is also provided to bias first frame portion 905 and second frame portion 910 closed relative to one another. This configuration of punch 900 may be used in connection with the left ventrical approach with handle 935 being operable with a two tube controller (not shown). Alternatively, the shaft of adjustable connector 915 may be threadably connected to either first frame member 905 or second frame member 910 so as to allow adjustable connector 915 to open or close punch 900 with a twisting motion.

Looking now at FIGS. 13-17, an aortic approach punch 945 is shown for resecting diseased valve (not shown) using an aortic approach. Aortic approach punch 945 includes a first frame member 950 and a second frame member 955, with the two frame members being selectively movable by an actuator 960 so as to engage one another. First frame member 950 and second frame member 955 contain cutting edges 965, 970, respectively. Cutting edges 965, 970 engage with one another as operated by actuator 960 so as to sever and contain a portion of an aortic valve 975 positioned therebetween.

In a preferred embodiment of the present invention, first frame member 950 and second frame member 955 each contain a mesh filter 980. Each mesh filter 980 allows blood flow through punch 945 and prevents portions of the resected valve larger than openings in mesh filter 980 from passing through punch 945.

Looking now at FIG. 16, second frame member 955 is shown with a seat 985 for holding a portion of the resected valve against a corresponding structure of first frame member 950. Seat 985 is configured with voids 990 so as to permit blood flow through punch 945 while simultaneously holding the resected portion.

Figure 17:
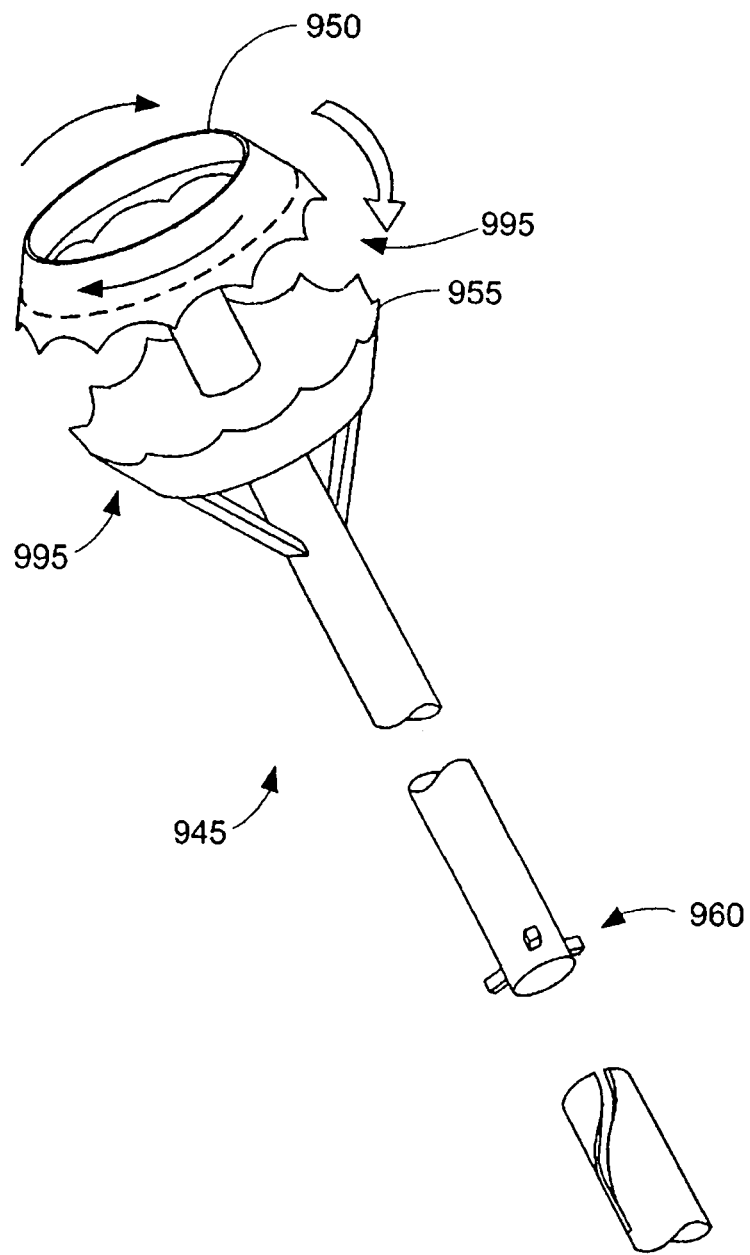

Looking now at FIG. 17, the aortic approach punch 945 is shown with first frame member 950 and second frame member 955 each having cutting teeth 995 in rotatable engagement with one another. Actuator 960 is configured to rotate and engage first frame member 950 and second frame member 955 relative to one another so as to cut portions of an aortic valve therebetween using cutting teeth 995.

Referring now to FIGS. 18-22, a power shaver guide 1000 is shown for resecting a heart valve with a power shaver 1005, such as a commercially available arthroscopic device. Power shaver guide 1000 includes an opening 1010 to receive power shaver 1005 therethrough. Power shaver guide 1000 is sized to fit within the aorta. Preferably, power shaver guide 1000 is sized large enough to prevent power shaver 1005 from unintentionally cutting through a wall of the aorta but small enough to fit inside of the diseased valve. In addition, the diseased valve may be crushed prior to introduction of power shaver guide 1000 and power shaver 1005.

Figure 18:
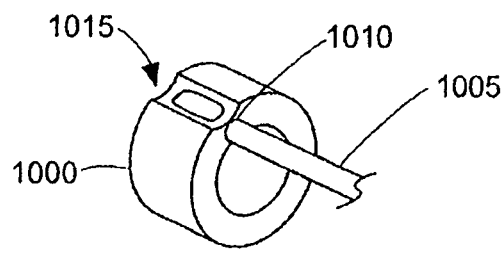
FIGS. 18-22 are schematic views of preferred embodiments of the present invention for resection of a heart valve using a power shaver in combination with a power shaver guide.
Figure 19:
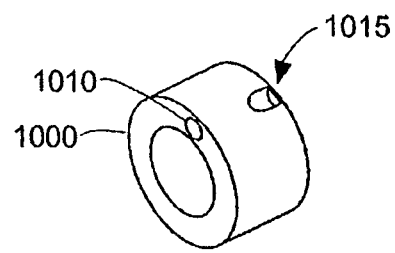

Looking now at FIGS. 18 and 19, a cutting window 1015 is provided in power shaver guide 1000 to allow cutting therethrough and to shield power shaver 1005 from cutting through the wall of the aorta.

Figure 20:
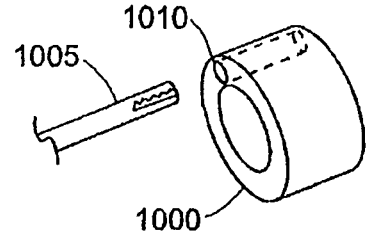
Figure 21:
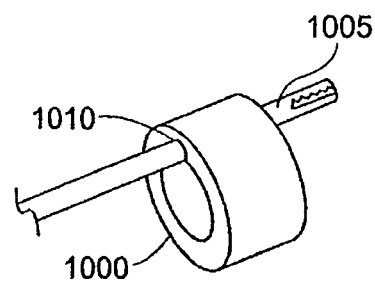

Looking now at FIGS. 20 and 21, power shaver guide 1000 is shown with opening 1010 configured to hold power shaver 1005 positioned therethrough without requiring cutting window 1015 (see FIGS. 18 and 19).

Figure 22:
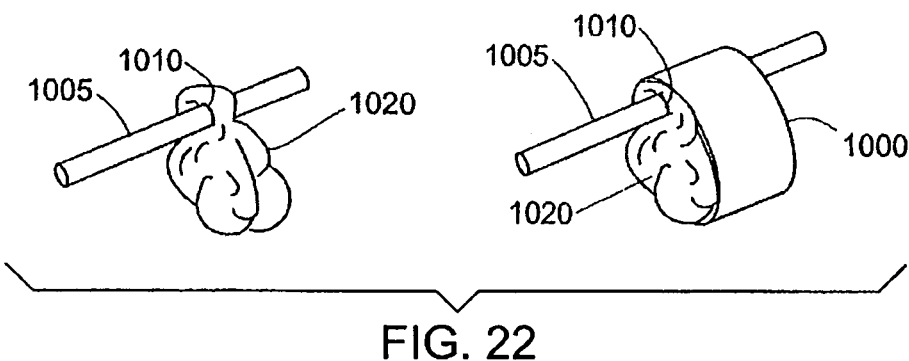
Figure 26:
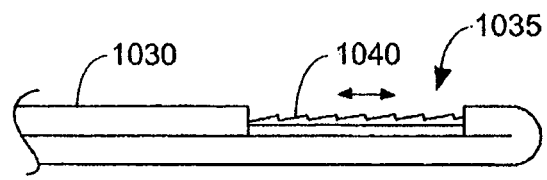
Figure 27:
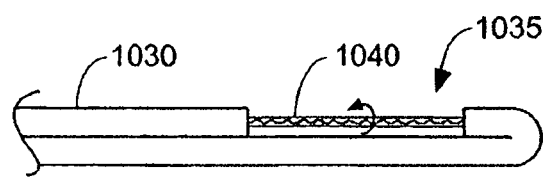
Figure 28:
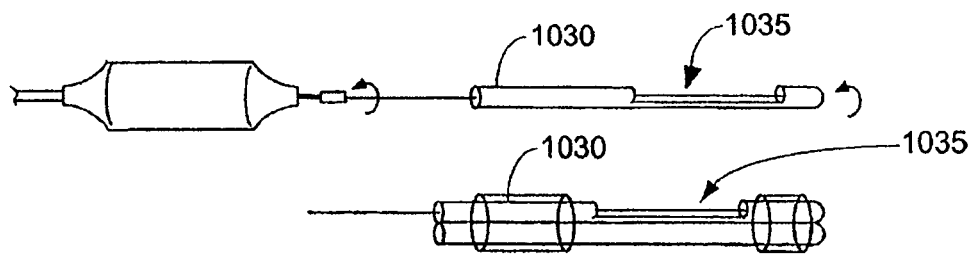
Figure 29:
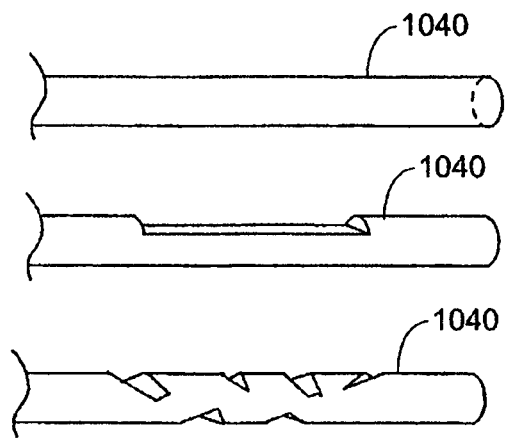
Figure 30:
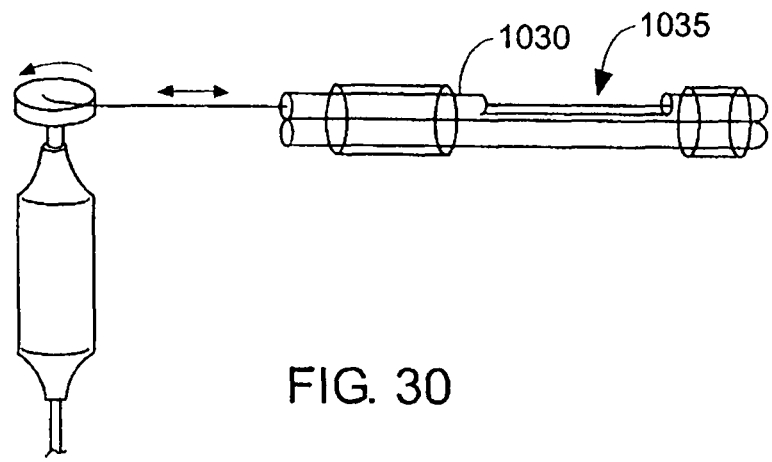
Figure 31:
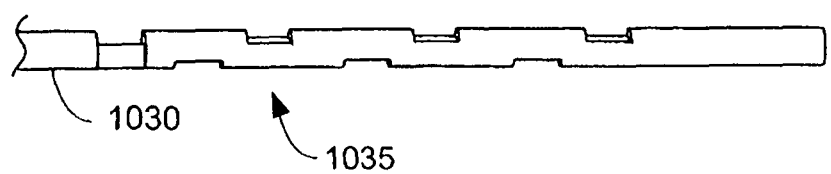
Figure 32:
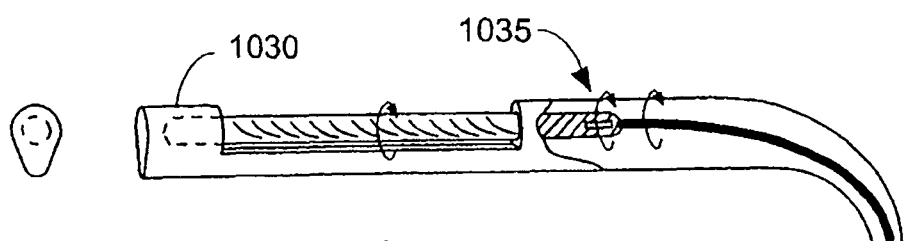
Figure 35:
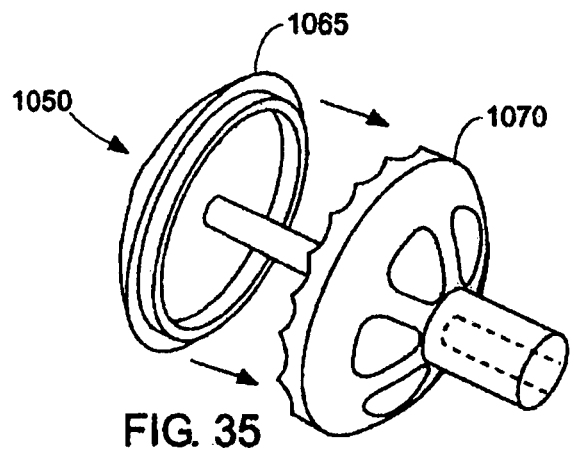
FIGS. 33-37 are schematic views of a spiked resector for holding portions of the valve prior to closing the cutting portions together.
Figures 33, 34:
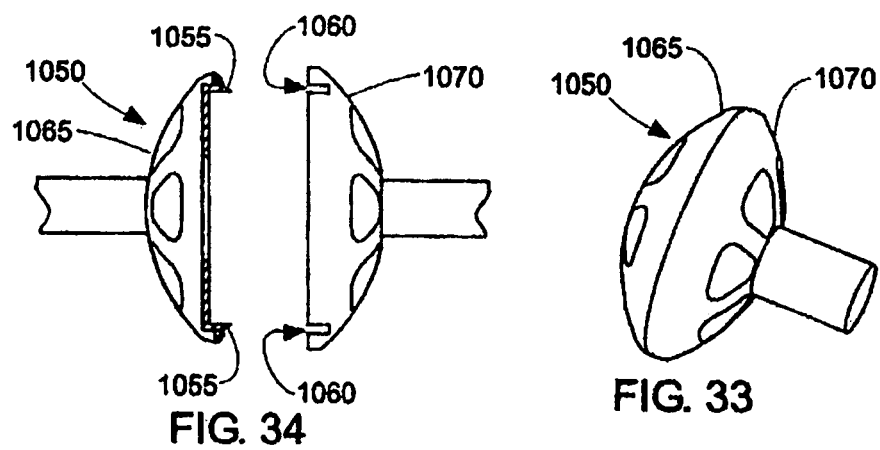
Figure 36:
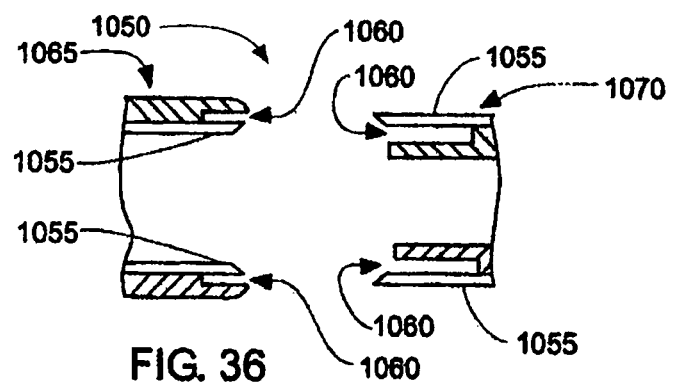
Figure 37:
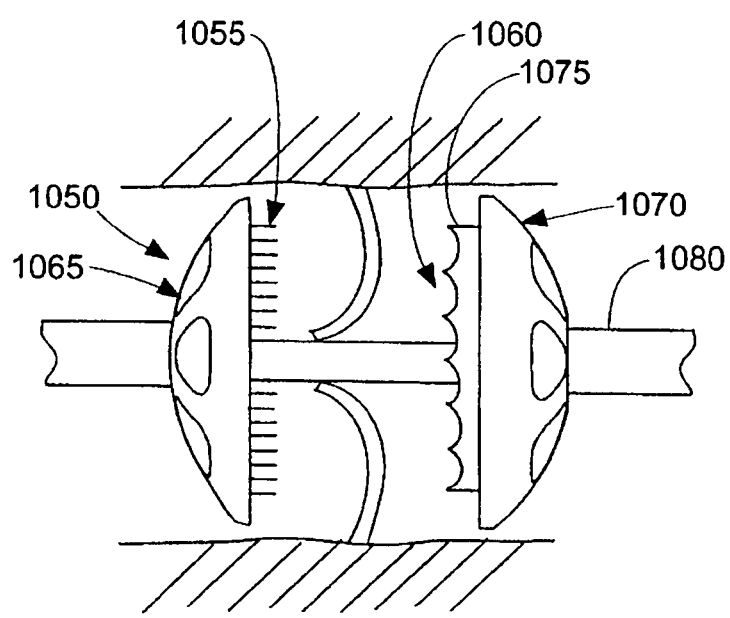
Figure 44:
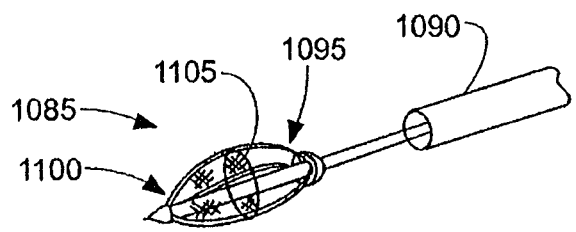
Figure 46:
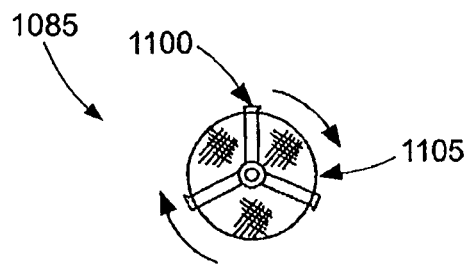
Figure 45:
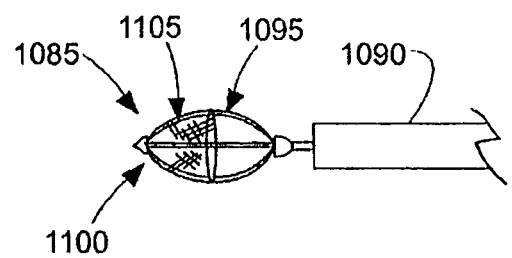
Figure 47:
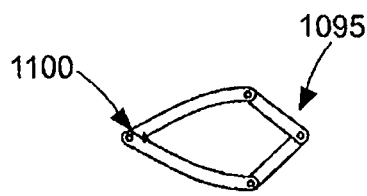
Figure 48:
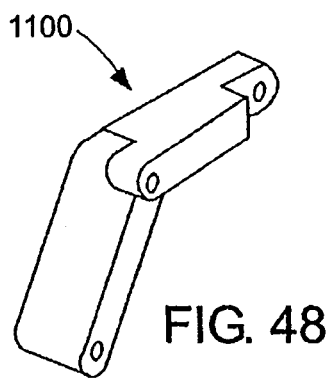
Figure 49:
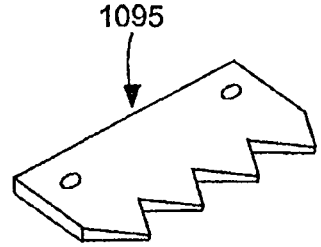
Figure 50:
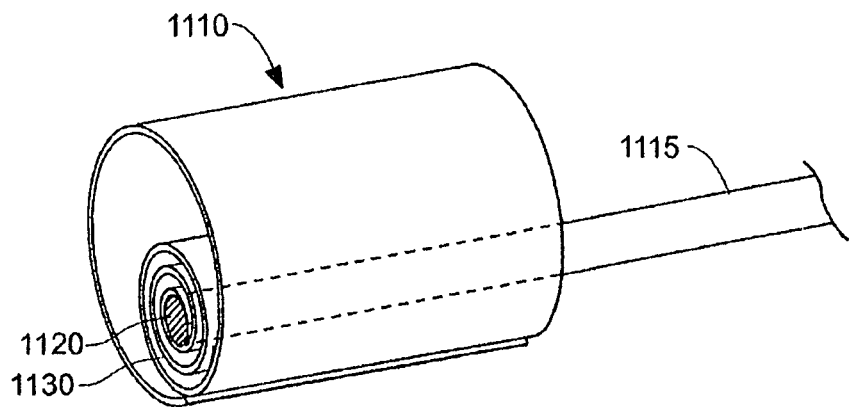
FIGS. 50-57 are schematic views of a preferred embodiment of the present invention including an expandable cylinder resector delivered through a catheter.
Figure 51:
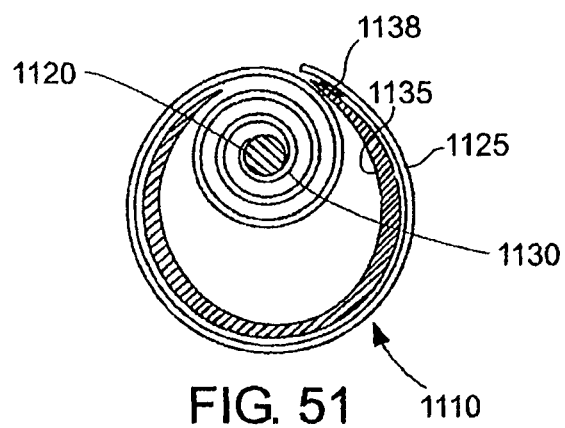

Looking now at FIG. 22, in another preferred embodiment of the invention, power shaver guide 1000 is collapsible. Collapsible power shaver guide 1000 preferably comprises an inflatable balloon 1020. Inflatable balloon 1020 is shown in a collapsed state for insertion into the aorta and in an inflated state for resection of the diseased valve.

Looking now at FIGS. 23-32, in another preferred embodiment of the present invention, there is shown an expandable resector 1025 having three expandable arms 1030, in which one expandable arm 1030 carries a cutting device 1035. Cutting device 1035 includes a wire 1040, which is either rotary driven or reciprocally driven, so as to cut portions of a diseased valve. Wire 1040 is positioned within expandable arm 1030 to create a cutting window 1045. Cutting window 1045 may be formed either by recessing wire 1040 into expandable arm 1030 or by building up the portions of expandable arm 1030 surrounding cutting window 1045.

Wire 1040 may include a rough, abrasive surface for rotary driven or reciprocally driven cutting. Alternatively, wire 1040 may include an electrocautery element for cutting. A power shaver may also be used in place of wire 1040. The rough or abrasive embodiment of wire 1040 may include recesses formed in the wire 1040 or an abrasive metal dust coating added to it.

Looking now at FIGS. 33-37, in another preferred embodiment of the present invention, there is shown a spiked resector 1050. Spiked resector 1050 includes at least two spikes 1055 to hold valve leaflets in place as frame members 1065, 1070 are advanced toward one another. Spiked resector 1050 also includes a spike receiving portion 1060 to allow frame members 1065, 1070 to closely approach one another in order that a cutting mechanism 1075 (FIG. 37) cuts through the valve leaflets. In addition, one of the frame members 1065, 1070 may be mounted to a screw-driven assembly 1080 so as to axially rotate the mounted frame member to aid in cutting.

Referring now to FIGS. 38-49, in another preferred embodiment of the present invention, there is shown an expandable blade resector 1085 for resection of a heart valve using a catheter 1090. Expandable blade resector 1085 includes a set of blades 1095 and a hinged portion 1100. Blades 1095 and hinged portion 1100 are selectively positionable through catheter 1090. In a preferred embodiment of the present invention, expandable blade resector 1085 includes a filter mesh portion 1105 (FIG. 44) at a distal end thereof covering hinge 1095. Filter mesh portion 1105 acts to capture portions of the resected valve. Blades 1095 may also be serrated to aid in cutting through a valve.

Figure 53:
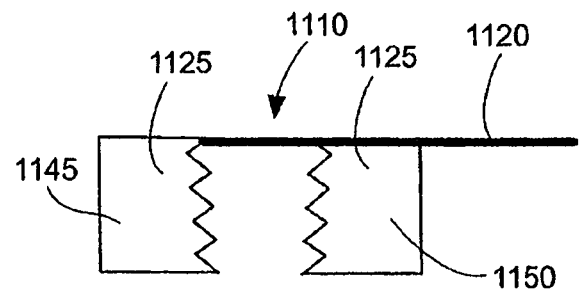
Figure 54:
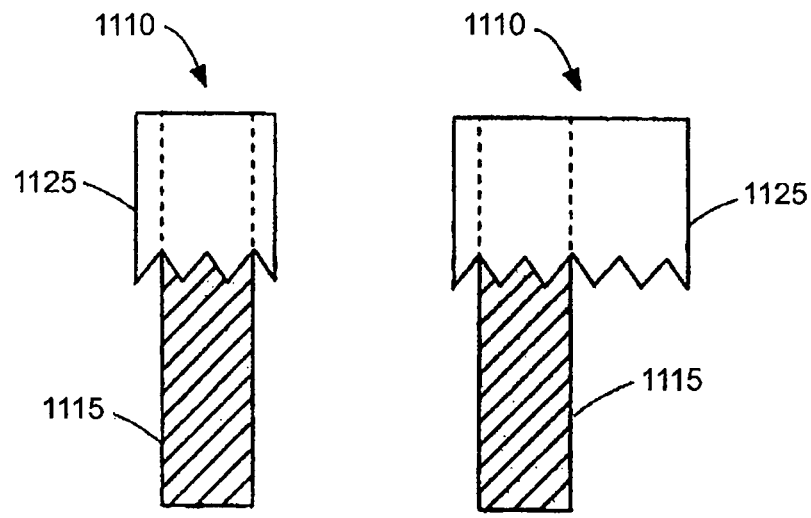
Figure 52:
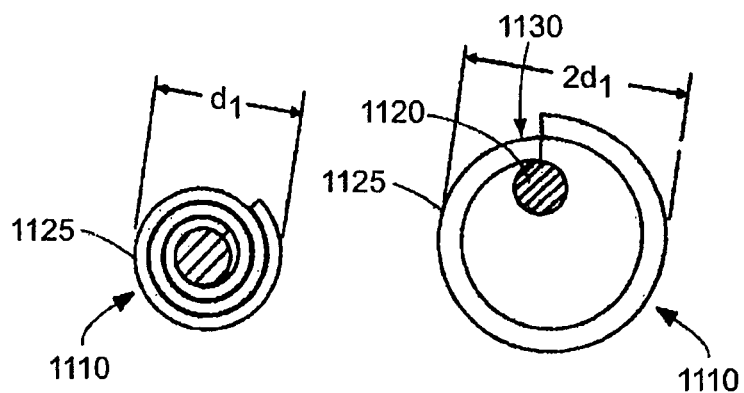
Figure 57:
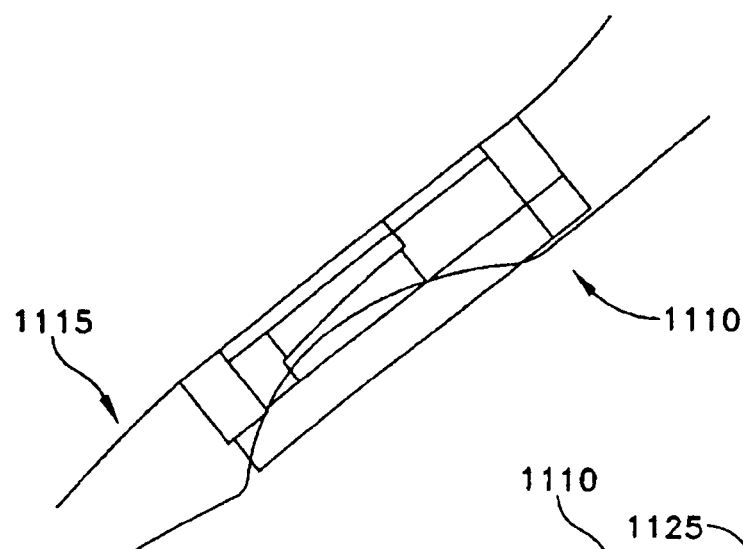
Figure 56:
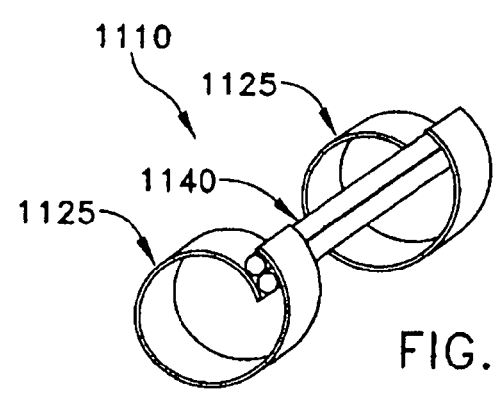
Figure 55:
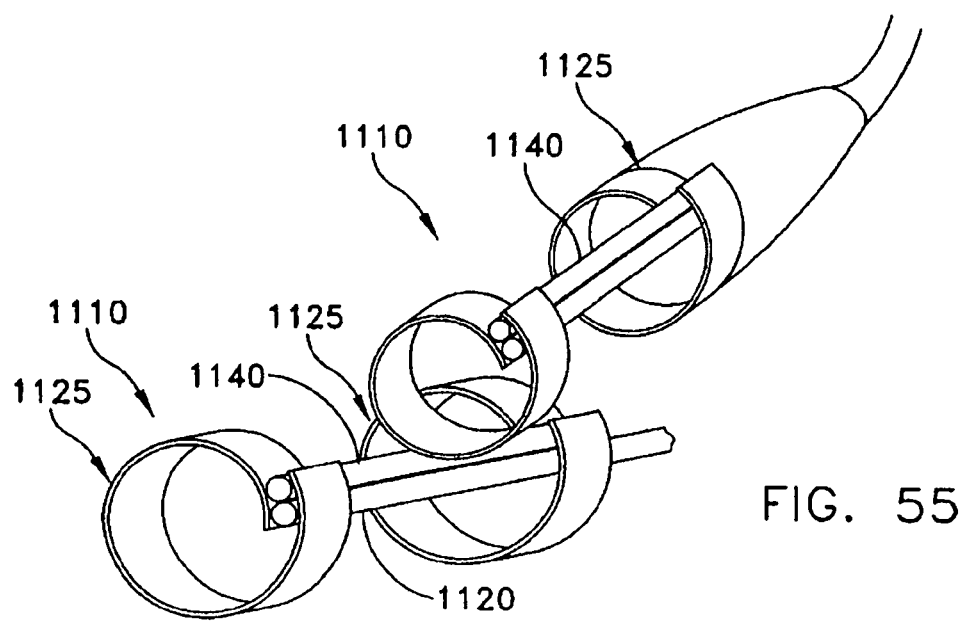

Looking now at FIGS. 50-57, in another preferred embodiment of the present invention, there is shown an expandable cylinder resector 1110 for resection of a heart valve using a catheter 1115. Expandable cylinder resector 1110 includes an inner rod 1120 attached to catheter 1115, an outer shell 1125 attached to inner rod 1120 at a first portion 1130 and in surrounding relation to inner rod 1120, and a spring 1135 being attached to outer shell 1125 at a second portion 1138 and contained by outer shell 1125. Expandable cylinder resector 1110 is operated by placing the outer shell 1125 within a portion of a heart valve and then turning inner rod 1120 to allow spring 1135 to expand the diameter of outer shell 1125 relative to inner rod 1120. In this configuration, expandable cylinder resector 1110 may be used to crush portions of a valve and/or as a centering guide in combination with another resecting tool shown mounted at 1140 (FIG. 55).

Looking now at FIGS. 53 and 54, inner rod 1120 is preferably adjustable to selectively open and close together two portions 1145, 1150 of outer shell 1125. These portions 1145, 1150 may be placed in an open position adjacent to an aortic valve and then actuated by inner rod 1120 to a closed position so as to cut through the aortic valve.

Figure 58:
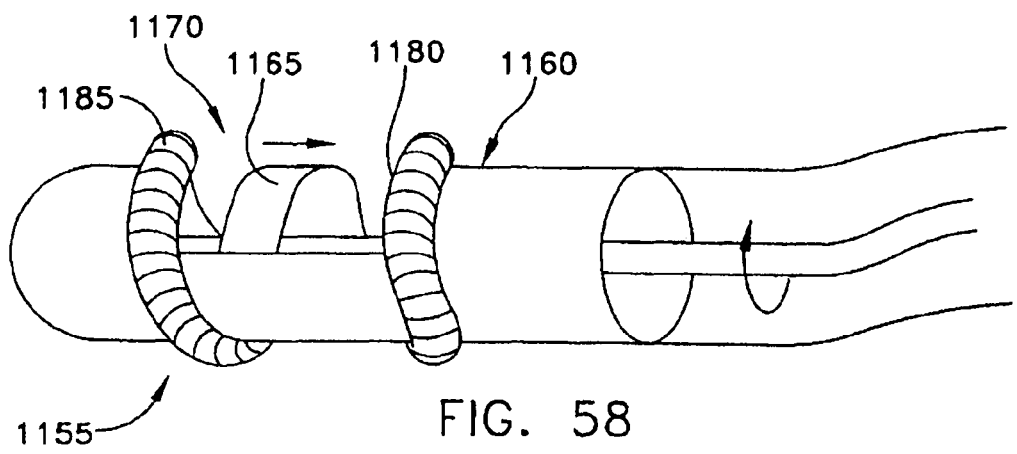
FIGS. 58-60 are schematic views of a preferred embodiment of the present invention including a power auger cutter for cutting and removing portions of a heart valve.
Figure 59:
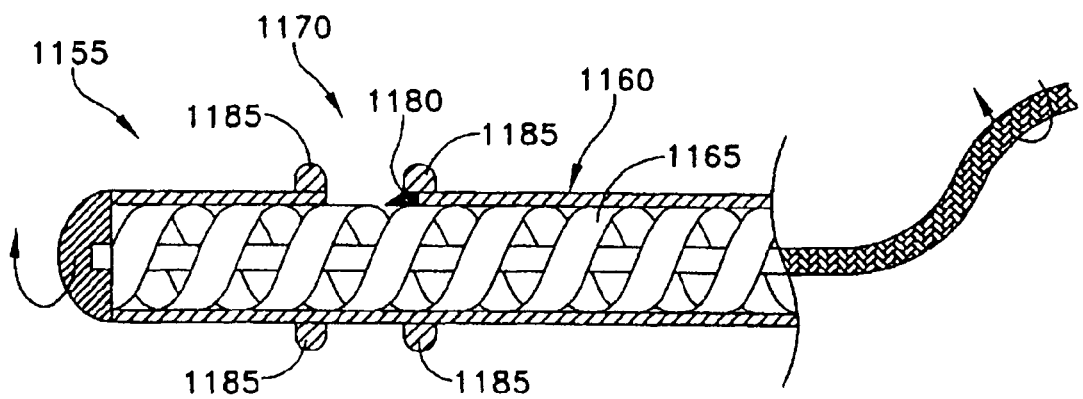
Figure 60:
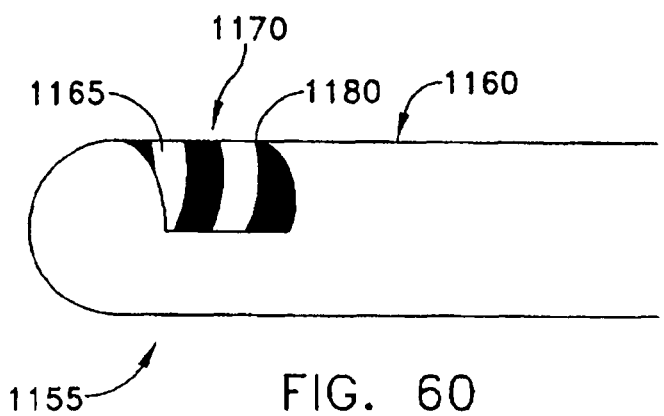
Figure 65:
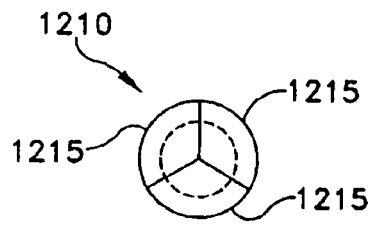
FIGS. 64-70 are schematic views of a preferred embodiment of the present invention including a trisector having three cutting blades.
Figure 64:
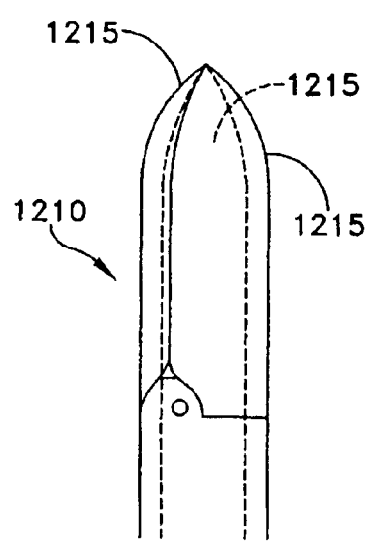
Figure 66:
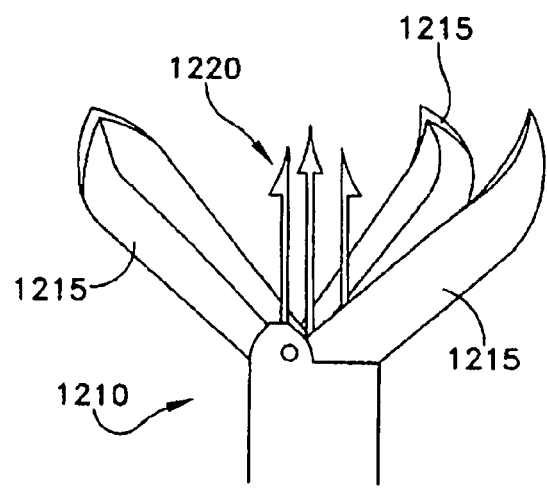
Figure 67:
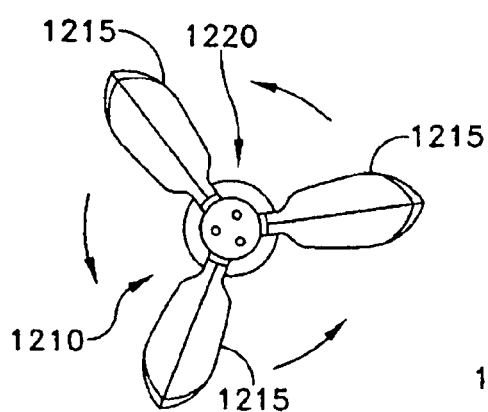
Figure 68:
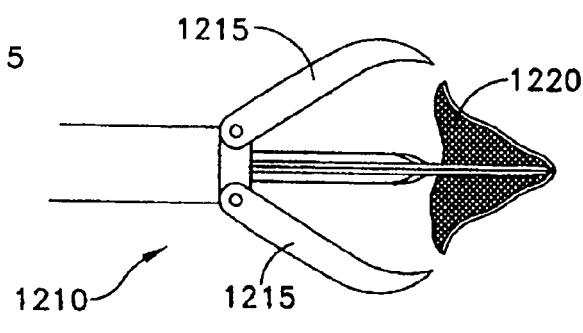
Figure 69:
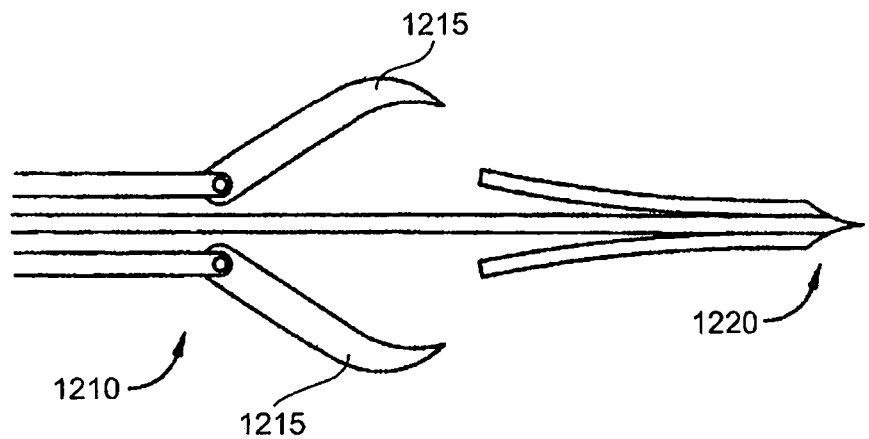
Figure 70:
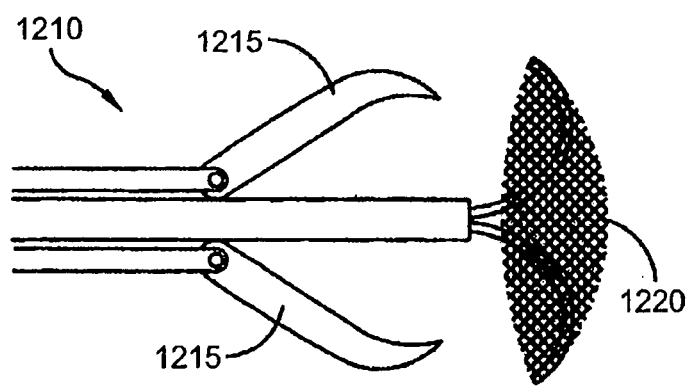
Figure 72:
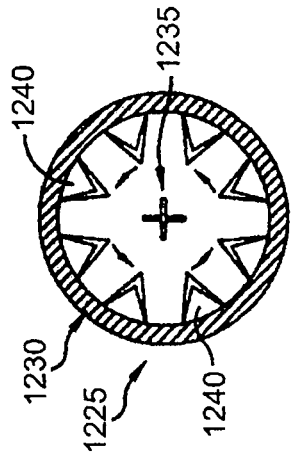
FIGS. 71-76 are schematic views of a preferred embodiment of the invention including a valve entrapment cutter.
Figure 71:
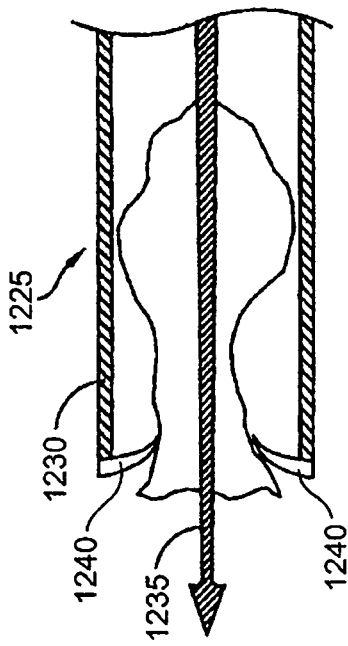
Figure 76:
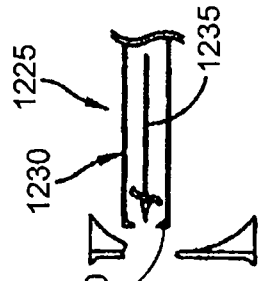
Figure 75:
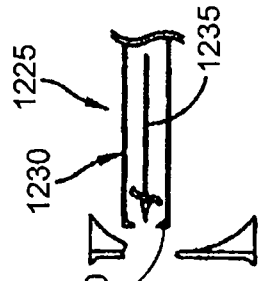
Figure 74:
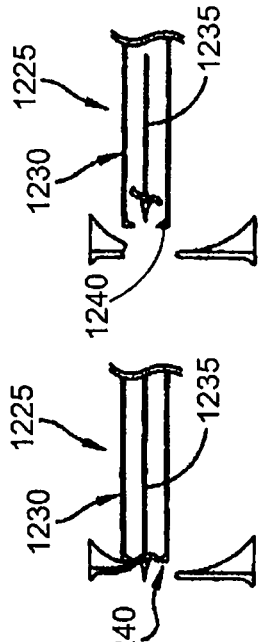
Figure 73:
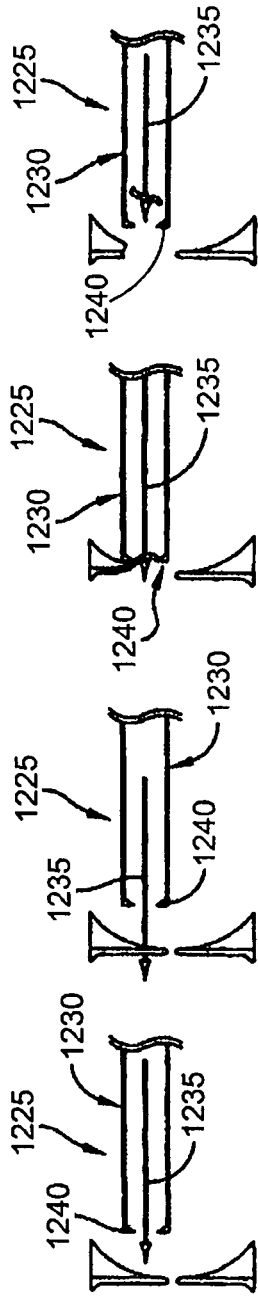
Figure 80:
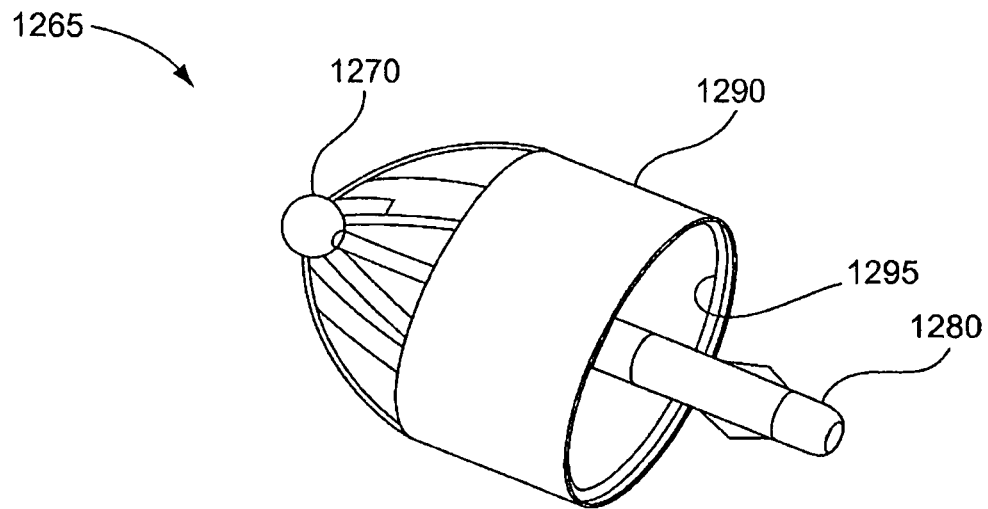
FIGS. 80-90 are schematic views of a preferred embodiment of the present invention including a valve cutter and resector for use with a left ventrical approach.
Figure 81:
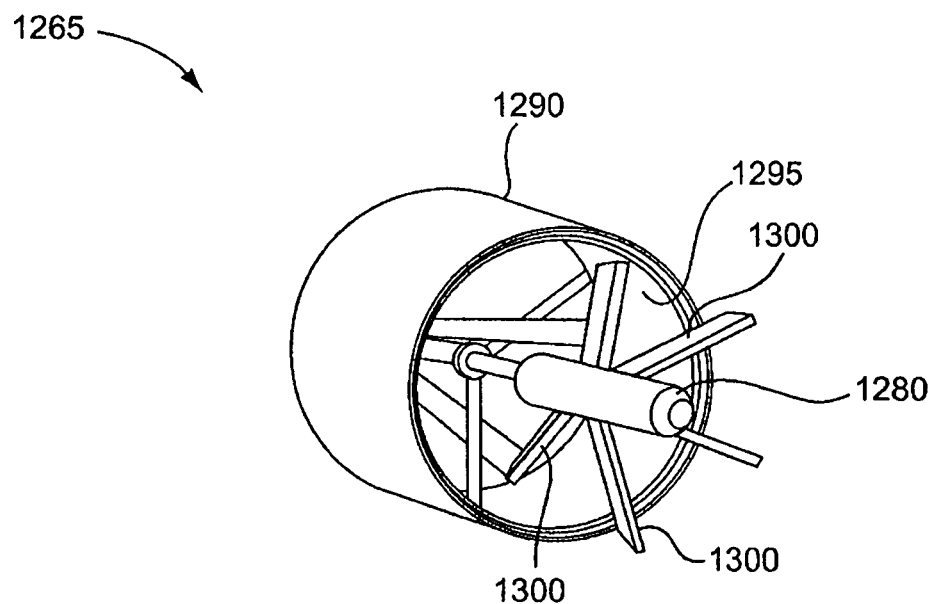
Figure 82:
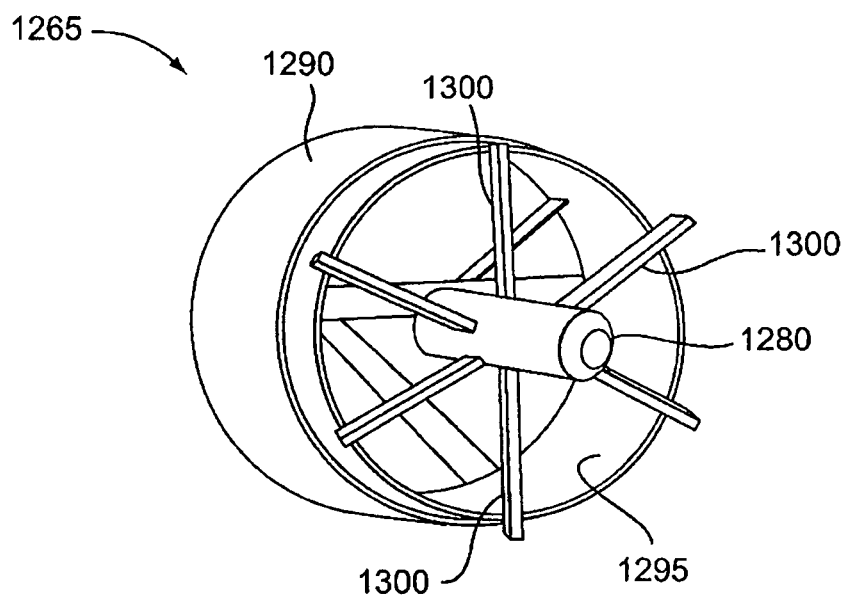
Figure 83:
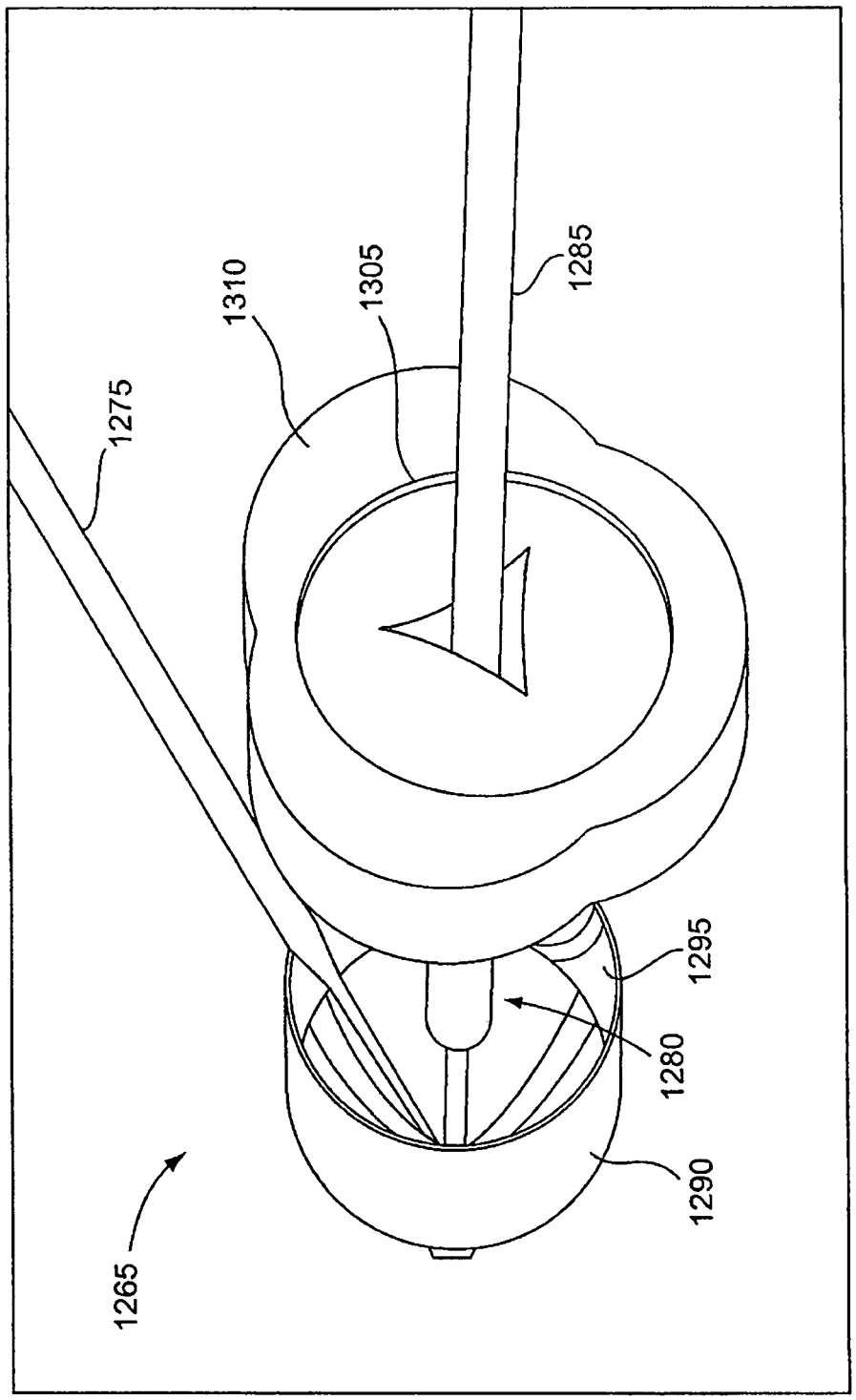
Figure 84:
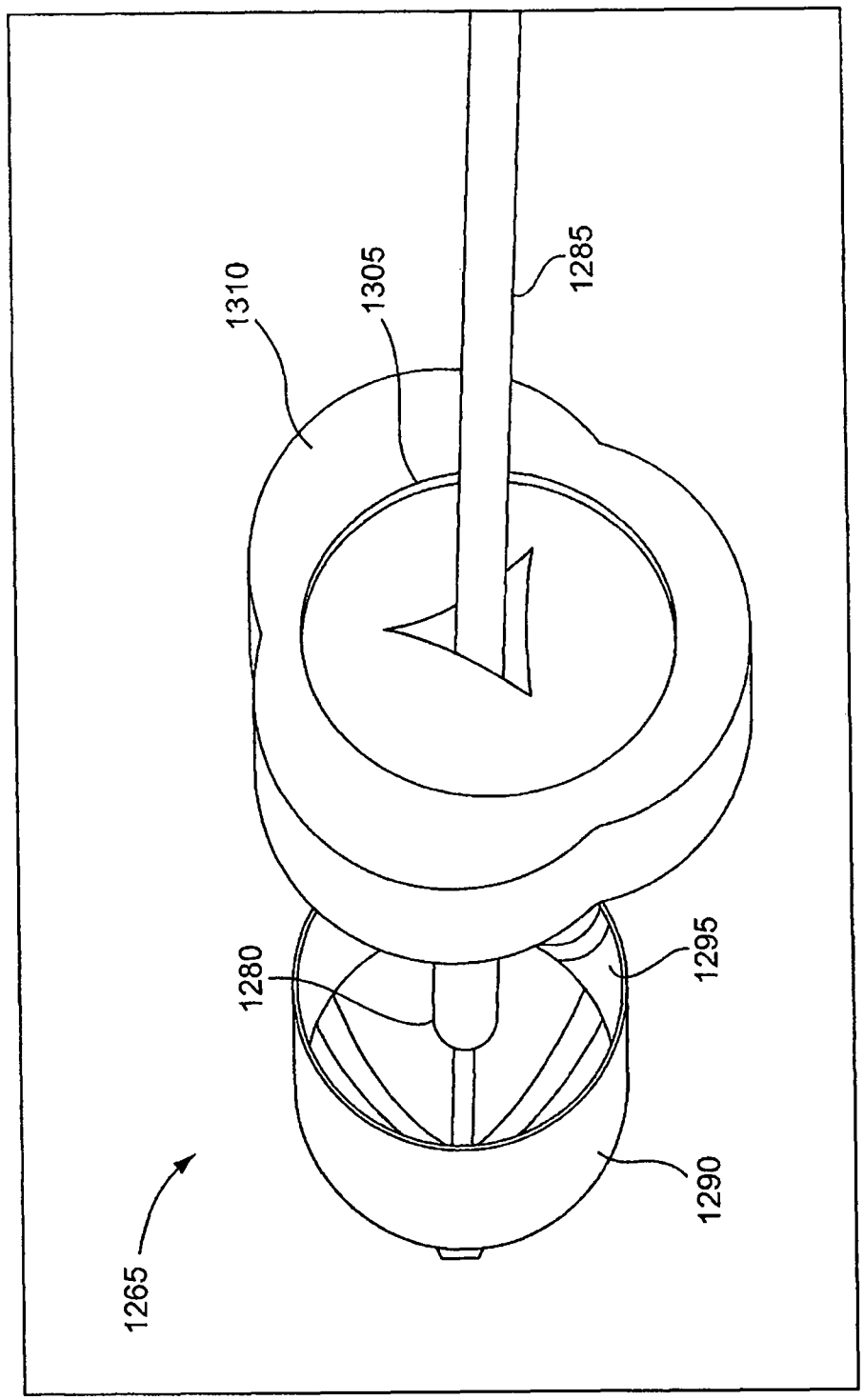
Figure 85:
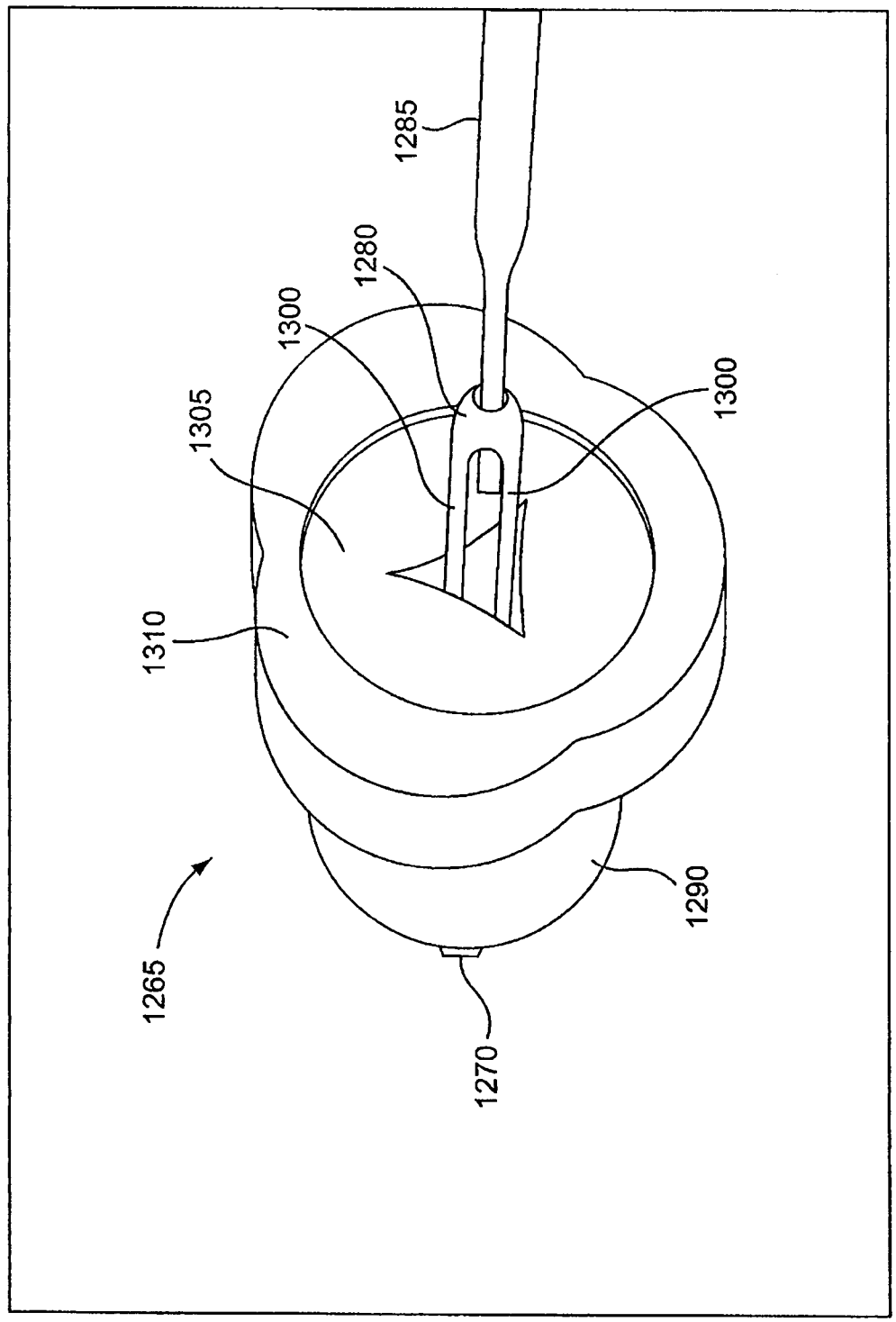
Figure 86:
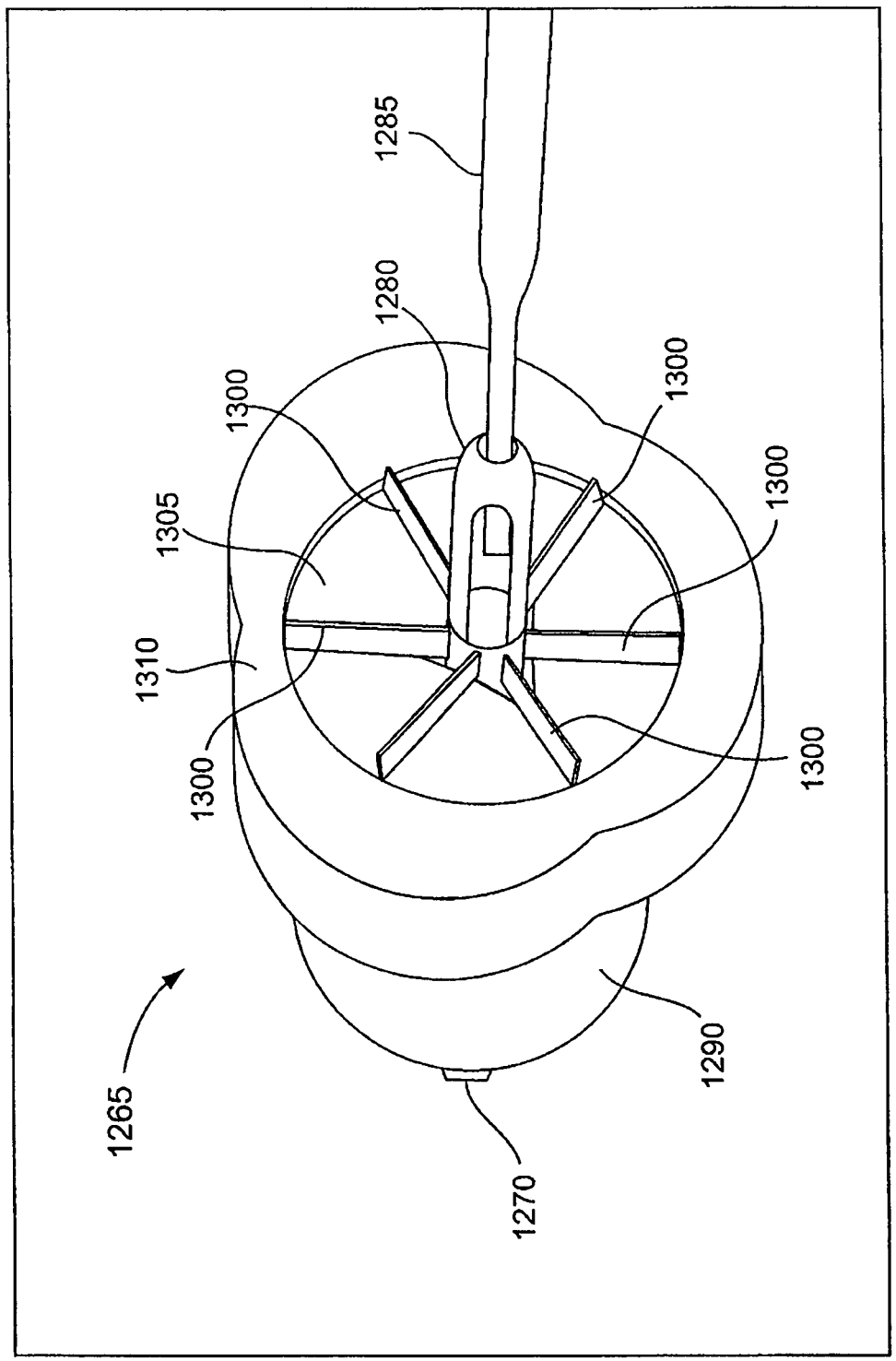
Figure 87:
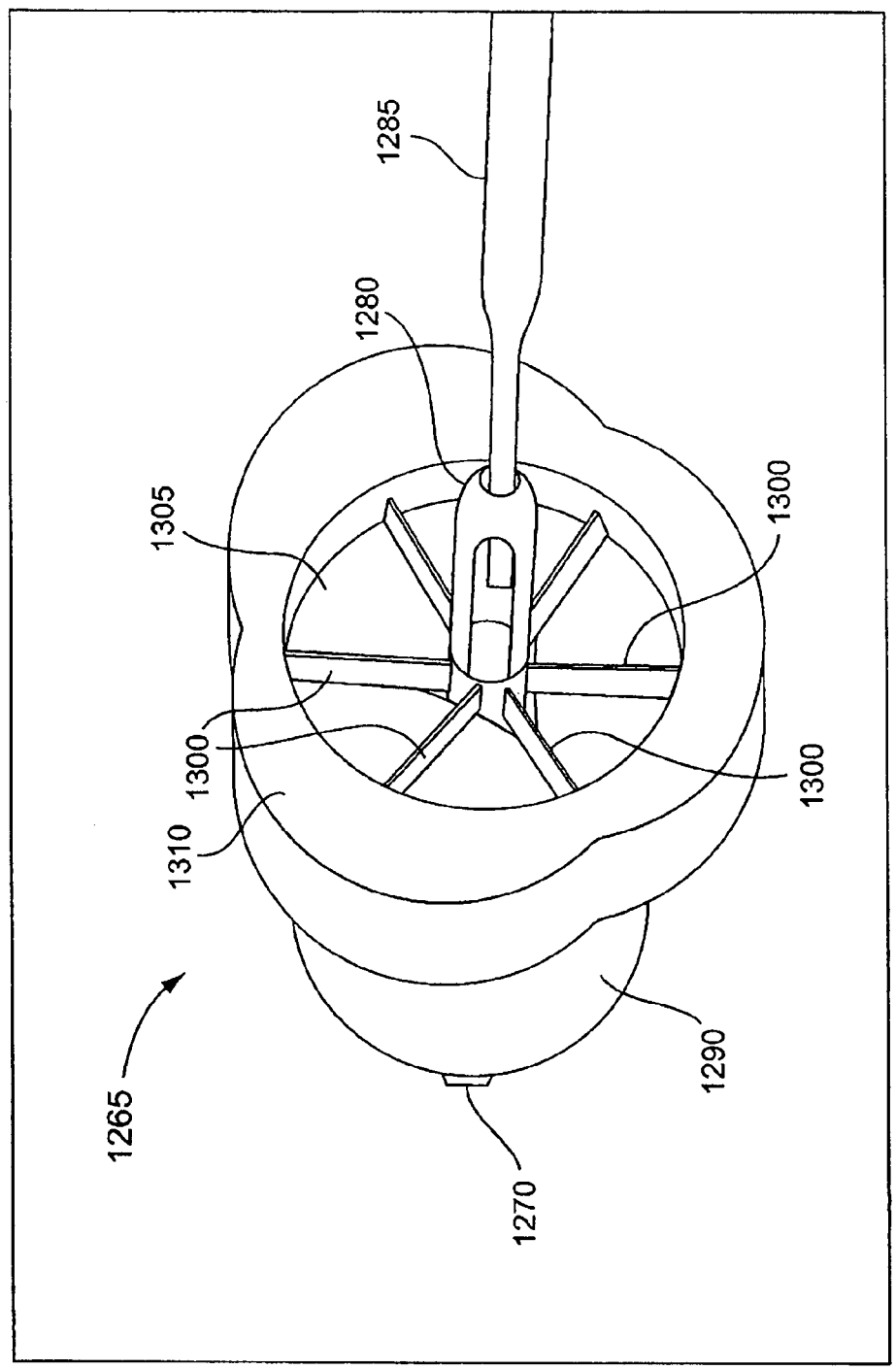
Figure 88:
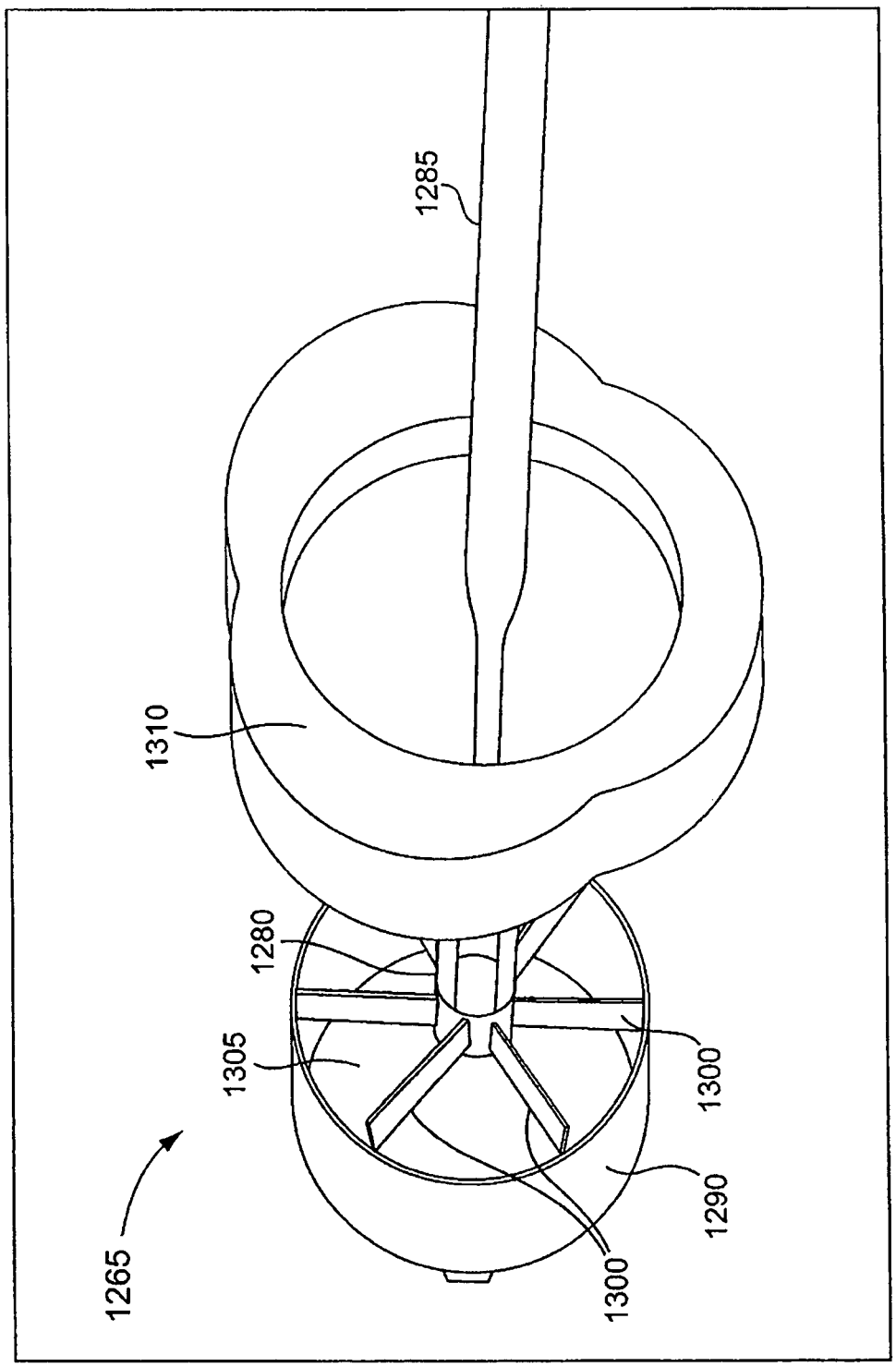
Figure 89:
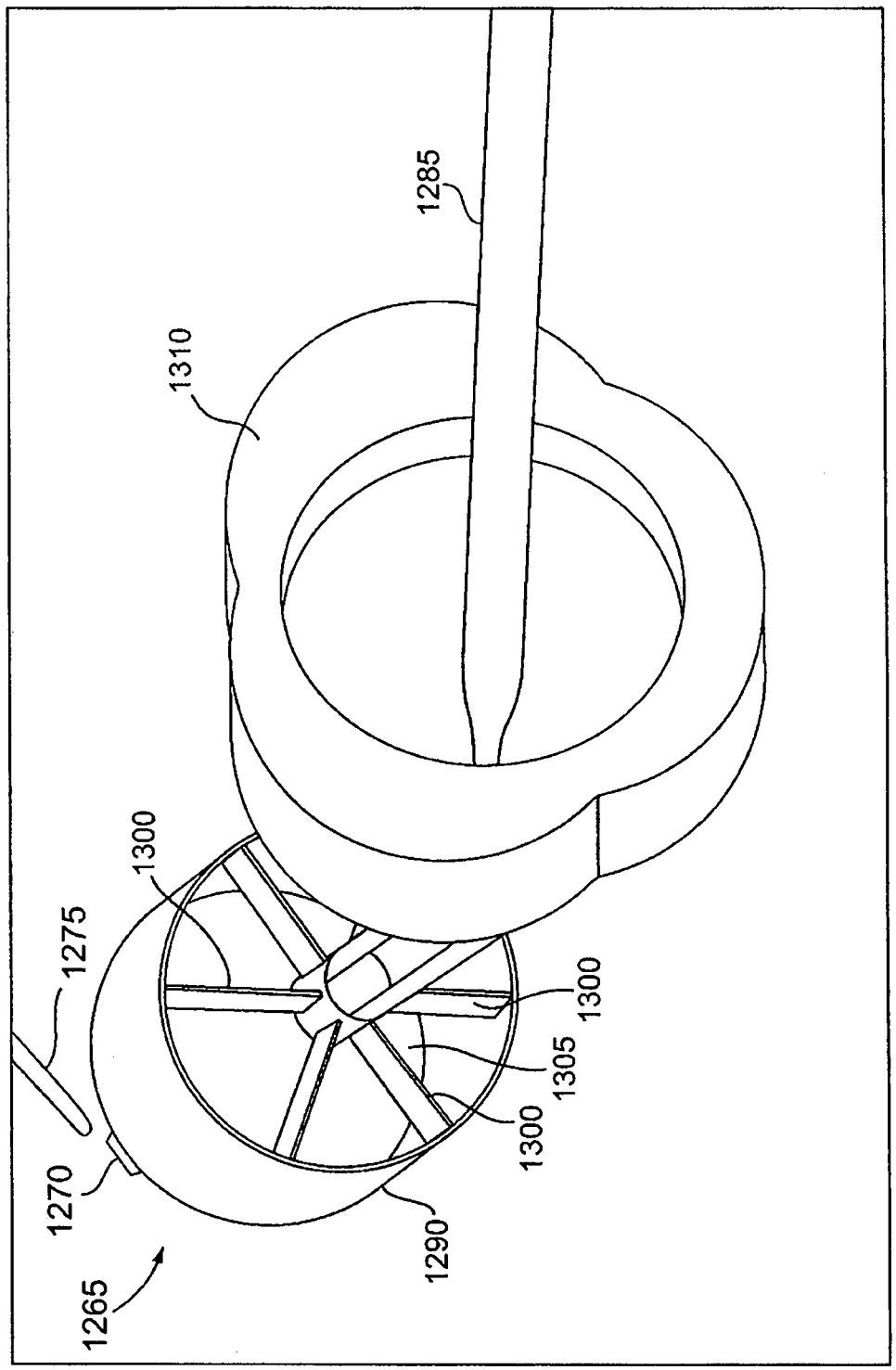
Figure 90:
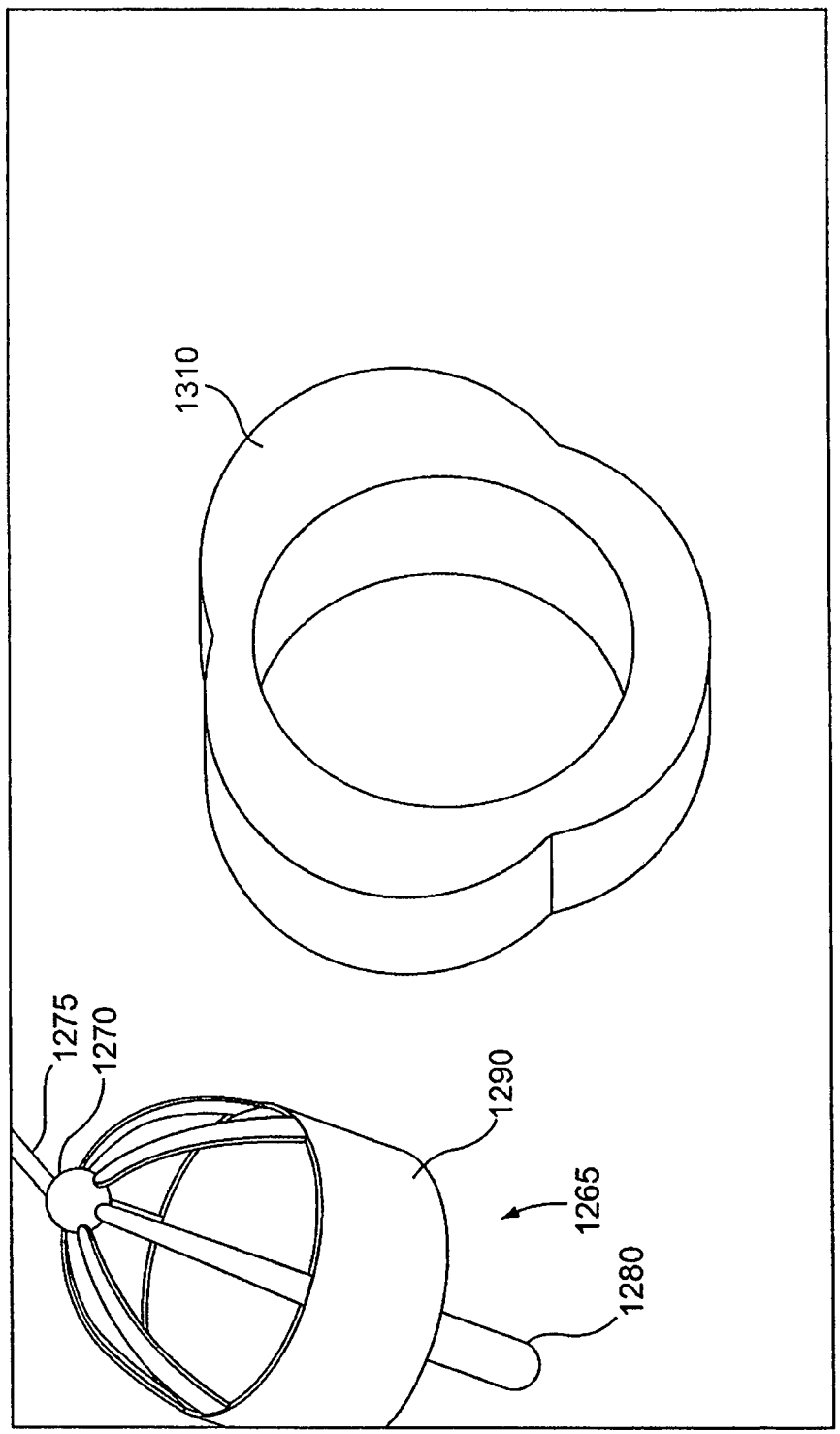

Referring now to FIGS. 58-60, in another preferred embodiment of the present invention, there is shown a power auger cutter 1155 for cutting and removing portions of a heart valve. Power auger cutter 1155 includes a tubular body 1160 containing an auger blade 1165. An opening 1170 is formed in tubular body 1160 to allow portions of a heart valve into the interior of power auger cutter 1155. Power auger cutter 1155 is configured to cut portions of the heart valve extending into opening 1170 by carrying the portions with auger blade 1165 deeper into tubular body 1160 until auger blade 1165 contacts tubular body 1160 at a junction 1180. After the severed portions of the heart valve pass junction 1180, auger blade 1165 continues to carry these portions through tubular body 1160 and out of the aorta.

Looking now at FIGS. 58 and 59, power auger cutter 1155 is provided with a set of guides 1185. Guides 1185 are positioned around at least a portion of opening 1170, which acts to shield against cutting the wall of the aorta. Preferably, the width of power auger cutter 1155 is about 0.20% of the aorta.

Looking at FIG. 60, power auger cutter 1155, configured without a set of guides, is preferably used with a delivery system. The delivery system either provides a shield against cutting the wall of the aorta or positions power auger cutter 1155. One such system is the expandable resector with three arms.

Referring now to FIGS. 61-63, in a preferred embodiment of the present invention, there is shown an offset cutter 1190. Offset cutter has an inner rod 1195, an outer shell 1200, and a cutting blade 1205 positioned at the end of outer shell 1200. The diameter of outer shell 1200 is controlled by increasing or decreasing its length extending out of inner rod 1195. The large diameter of outer shell 1200 acts as a guide to shield against cutting the wall of the aorta with cutting blade 1205 as it cuts away portions of a heart valve.

Referring now to FIGS. 64-70, in a preferred embodiment of the present invention, there is shown a trisector 1210 having three blades 1215 for resecting a heart valve. In a preferred embodiment of the present invention, barbs 1220 are provided at a center portion of the trisector to spear and hold the leaflets of the heart valve while blades 1215 spin to cut through the heart valve. Blades 1215 may be configured to cut at a forward portion of trisector 1210, in which case trisector 1210 acts as plunging cutter. Alternatively, blades 1215 may be configured to cut at a side portion of the trisector 1210, in which trisector 1210 acts as a side cutter. For very hard calcification of a heart valve, it is preferred that trisector 1210 be configured as a plunging cutter to cut in a forward direction.

In an alternative preferred embodiment of the present invention, trisector 1210 is provided with a filtering mechanism 1220 (FIG. 68) to contain cut away portions of the valve for removal from the patient's body.

Referring now to FIGS. 71-76, in a preferred embodiment of the present invention, there is shown a valve entrapment cutter 1225. Valve entrapment cutter 1225 includes a chamber 1230 with a retractable barb 1235 and a set of blades 1240 surrounding an end of chamber 1230. Blades 1240 may be configured to rotate around barb 1235 so as to cut through a portion of a valve pierced by barb 1235 as the portion enters chamber 1230. Alternatively, chamber 1230 may be configured to rotate around barb 1235 as the portion enters chamber 1230.

Referring now to FIGS. 77-79, in a preferred embodiment of the present invention, there is shown a gripper cutter 1240 for the resecting of a portion of a heart valve. Gripper cutter 1240 includes a pair of graspers 1245 contained in a body 1250 with a cutting element 1255 positioned therebetween. Graspers 1245 are extended distally from the distal end of body 1250 so as to contact a portion 1260 of a heart valve. Graspers 1245 are closed together through actuation of either graspers 1245 or body 1250. Graspers 1245 are then retracted with heart valve portion 1260 into body 1250. Cutting element 1255 closes together after graspers 1245 are retracted to a given point proximal to the end of cutting element 1255. This action causes heart valve portion 1260 to be cut away from the remaining portion of the heart valve and to be contained within body 1250.

Referring now to FIGS. 80-90, in a preferred embodiment of the present invention there is shown valve cutter and resector 1265 for use in a left ventrical approach. Valve cutter and resector 1265 includes a first handle 1270 for connection to a pass-off tool 1275 located in the left ventricle of the heart, a second handle 1280 for connection to a controller tool 1285 located in the aorta, a body portion 1290 between first handle 1270 and second handle 1280, a cutting blade 1295 axially rotatable on the inside surface of body portion 1290, and a set of retaining arms 1300 (FIG. 86) selectively expandable from second handle 1280. Valve cutter and resector 1265 is operable to resect a portion 1305 of an aortic valve 1310 by advancing through the left ventricle of the heart to aortic valve 1310 by means of pass-off tool 1275. Next, controller tool 1285 is advanced through the aorta, passes through the opening of aortic valve 1310 and is received by second handle 1280. First handle 1270 is then disengaged from pass-off tool 1275. Controller tool 1285 draws body portion 1290 distally with cutting blade 1295 spinning to cut through aortic valve 1310. Retaining arms 1300 expand from a folded configuration within second handle 1280 and hold resected portion 1305 within body portion 1290. First handle 1270 is repositioned and re-engaged to pass-off tool 1275 for removal through the left ventricle of the heart, with controller tool 1285 being disengaged from second handle 1280.

Referring now to FIG. 91, in a preferred embodiment of the present invention, there is shown a resection tool 1315 having a protective guide 1320A-1320D to prevent cutting of the aortic wall through an opening 1325. In a preferred embodiment of the present invention, protective guide 1320A is a rigid structure in a surrounding configuration to opening 1325. This embodiment is illustrated by the "double bridge" design. In another preferred embodiment of the present invention, protective guide 1320B-1320D is a flexible structure adjacent to opening 1325. This embodiment is illustrated by the "inchworm", "cantilever", and "window slide" designs, in which a maximum deformation of the flexible structure is shown in phantom.

Looking next at FIGS. 92-101, there is shown a modified form of valve cutter and resector 1265. Again, this particular embodiment of debridement tool was designed with left atrial insertion and intra-cardiac hand-off in mind. A basic idea of this embodiment is the use of a thin-walled cylinder or body portion 1290 size-specific for the patient's anatomy. Here the tolerances are fairly small. The patient's left ventricular outflow tract and aortic valve annulus are carefully measured by transesophageal echo. An appropriately sized debridement tool 1265 (with an appropriately sized thin-wall cylinder 1290) is then selected. Within the thin-walled cylinder 1290 is a cylindrical razor or cutting blade 1295 with a serrated edge. This razor can be rotated manually by means of a catheter or controller tool 1285 attached during hand-off. The razor 1295 is completely contained within the thin-walled cylinder 1290 until actuated. The back of the cylinder is attached to a wire cage 1330 that streamlines the profile to facilitate insertion and removal of the debridement tool across the mitral valve, and supports a cup of filter material 1335 (shown schematically in FIG. 92 only) to capture the valve and valve debris liberated at the time of debridement. Coaxial to, and extending a few centimeters forward of, the cylinder is the transvalvular snout, or second handle, 1280. This consists of a thin-walled tube with multiple side fenestrations that is forced across the stenotic valve. The multiple fenestrations allow the continued passage of blood across the orifice, without exacerbating the degree of stenosis or the outflow tract gradient.

The debridement tool is passed across the mitral valve on the beating heart. A catheter or controller tool 1285 based across the stenotic aortic valve (transvalvular catheter) is advanced into the left ventricular chamber, to effect an intra cardiac hand-off, as described previously. In one possible construction, the hand-off catheter 1285 is passed percutaneously, perhaps down the central lumen of a valve/filter assembly, also passed percutaneously.

Ideally, the snout 1280 of the debridement tool and the tip of the transvalvular catheter 1285 are both fitted with rare earth magnets or other appropriate structures so as to facilitate rapid reproducible alignment. Once aligned, the transvalvular catheter 1285 is actuated to achieve a mechanical coupling to allow the debridement tool to be pulled forcibly into position. The tool 1275 which was initially used to pass the debridement tool across the mitral valve is then released and removed after mechanical coupling is accomplished, but before pulling the debridement tool into position across the stenotic valve.

Attached to the aforementioned snout 1280 is an umbrella 1300 comprised of rays (or struts of nitinol or other superelastic material) or other satisfactory material supporting a disk of filter material 1340 similar to that attached to the back of the debridement tool. The umbrella 1300 is designed so that it can be pulled across the stenotic valve in a closed configuration, from the ventricular side of the valve to the aortic side of the valve, and subsequently opened. The umbrella struts form a skeleton with a radius equal to that of the thin-walled cylinder 1290, and slightly greater than the cylindrical razor 1295. The disk of filter material has a radius that is somewhat greater than that of the thin-walled cylinder 1290. The umbrella struts may be attached to a ring that slides longitudinally with respect to the snout. The transvalvular catheter, when actuated, causes both delivery of the umbrella to the aortic side of the valve as well as a configuration change from closed to open. The result is that the stenotic valve is impaled on the snout and wedged between the thin-walled cylinder on the ventricular side and the open umbrella on the aortic side.

In one embodiment, the umbrella 1300 is inverted. That is to say, when it is pulled across the stenotic valve, the apex of the umbrella is the first to pass, and the outer circumference of the umbrella tines and filter disk is last to pass. In this construction, the device is preferably spring-loaded so that when the tips of the tines clear the valve orifice and tension is released, the umbrella forms as a result of its own recoil against the aortic surface of the valve.

The geometry and construction of the debridement tool is such that it will orient coaxially with respect to the left ventricular outflow tract and the valve orifice. Once the umbrella 1300 is deployed, the position is carefully inspected by echo and/or fluoroscopy. When correctly deployed, only a small gap exists between the disk and the thin-walled cylinder. It is therefore impossible to position and deploy the device with anything other than valvular tissue within this narrow gap. Only if the debridement tool was deployed at a significant angle, or was markedly undersized, could aortic or left ventricular tissue become pinched in this gap. Once it is confirmed that the debridement tool's position is correct, and the umbrella 1300 is deployed, the cylindrical razor 1295 is manually advanced and rotated, again under echo and/or fluoroscopic guidance, while maintaining tactile feedback by way of a rotating central element of the transvalvular catheter. It is not imperative that the valve be debrided in its entirety; rather, that a hole result that has edges suitable for the fixation mechanism, and that is large enough to allow fixation of the prosthesis, and that will relieve the outflow tract gradient. As the fixation mechanism and the orifice of the prosthesis may not be co-planer in this application, the demands on debridement and orifice size may be considerably less than with a conventional prosthetic valve implantation.

As soon as the cylindrical serrated razor 1295 cuts through the last of the valvular tissue, there will be no tissue remaining to prevent the spring-loaded umbrella 1300 from retracting toward the thin-walled cylinder 1290, in effect snapping a lid on the cylinder with the valve remnants inside. Inasmuch as the umbrella 1300 and the cage 1330 at the back of the thin-walled cylinder are covered with filter material, the valve tissue cannot escape. Because the filter material is fairly transparent to blood, resistance to flow and cardiac emptying should not be significantly impacted by its presence in the left ventricular outflow tract. A single-use serrated cylindrical razor 1295, with teeth of an appropriately small size, when used in a proper fashion (multiple small amplitude rotations while applying minimal force) will be able to cut a smooth round hole out of even the most calcified and thickened valve.

Once the umbrella is seen (by echo and/or fluoro) to have snapped down on the cylinder, the inference is made that the valve has been completely excised. Valvular competence at this point is provided entirely by the down-stream valve, an embodiment of which is described as the valved arch filter (see U.S. Provisional Patent Application Ser. No. 60/425,877, filed Nov. 13, 2002 by William E. Cohn for CARDIAC VALVE PROCEDURE METHODS AND DEVICES, which patent application is hereby incorporated herein by reference). Any particulate material that escapes the debridement tool is prevented from embolizing by this down-stream filter.

The closed debridement tool, with the valve remnants inside, is then passed back across the mitral valve and removed through the left atrial blood-lock.

It should also be appreciated that a valve debridement tool may also comprise a laser, an ultrasonic device, a rotary drill bit, an auger, or any other mechanism that appropriately disrupts tissue.

Furthermore, the valve debridement tool can be passed down the aorta, through the valve and across to the ventricular side for deployment and retrograde cutting.

Preferably the valve debridement tool is formed so as to be selectively collapsible, whereby it may be advanced to the surgical site through a catheter, e.g., by a catheter introduced through a peripheral artery.

What is claimed is:

1. Apparatus for resecting a diseased heart valve of a heart, the apparatus comprising:
    an elongate member to allow the apparatus to be positioned in the heart, the elongate member having a distal end;
    a selectively expandable portion having a proximal end and a distal end, wherein the selectively expandable portion is positioned at the distal end of the elongate member, the selectively expandable portion defines a longitudinal axis from the proximal end to the distal end and is selectively expandable from a first position having a given width in a perpendicular direction to the longitudinal axis to a second position having a larger width in the perpendicular direction to the longitudinal axis; and
    at least one cutting element, for cutting the diseased heart valve, disposed on the elongate member wherein the at least one cutting element is moved from the first position to the second position by the selectively expandable portion;
    wherein the selectively expandable portion has a first opening extending into the proximal end, and the selectively expandable portion having a given width from the first opening to an outer surface in a direction perpendicular to the longitudinal axis of the selectively expandable portion, the given width configured to prevent a wall of a cardiovascular structure from being cut by the cutting element disposed on the elongate member that is within the first opening and to permit the apparatus to be placed within the diseased valve, wherein the selectively expandable portion comprises at least three expandable arms and the at least one cutting element is disposed on at least one of the at least three expandable arms, wherein at least one of the at least three expandable arms having the cutting element disposed thereon defines a window recess therein having a given depth from an outer surface, and further wherein the cutting element is disposed in the window recess.

2. Apparatus according to claim 1 wherein the at least one cutting element is disposed on the selectively expandable portion of the apparatus.

3. Apparatus according to claim 2 wherein when the selectively expandable portion is in the second position, the at least one cutting element cuts as the selectively expandable portion is rotated with respect to the longitudinal axis of the selectively expandable portion.

4. Apparatus according to claim 2 wherein the at least one cutting element extends longitudinally along the longitudinal axis of the selectively expandable portion such that when the at least one cutting element is in the second position, the at least one cutting element cuts as the selectively expandable portion is rotated with respect to the longitudinal axis of the selectively expandable portion.

5. Apparatus according to claim 2 wherein the at least one cutting element comprises a plurality of blades that move together and in a similar manner from the first position to the second position.

6. Apparatus according to claim 5 wherein the selectively expandable portion further comprises a hinge mechanism holding the blades together, the apparatus further comprises a control rod extending from the proximal end of the selectively expandable portion, and the control rod is able to position the blades from the first position to the second position.

7. Apparatus according to claim 1 wherein the at least one cutting element extends longitudinally along the elongate member and when the selectively expandable portion is in the second position, the at least one cutting element cuts as the selectively expandable portion is rotated with respect to the longitudinal axis of the selectively expandable portion.

8. Apparatus according to claim 1 further comprising a first restraining element at the proximal end of the set of expandable arms and a second restraining element at the distal end of the set of expandable arms, wherein the first and second restraining elements selectively position the set of expandable arms between the first and second positions.

9. Apparatus according to claim 1 wherein the elongate member comprises a catheter and the first position is with the selectively expandable portion being inside the distal end of the catheter and the second position is with the selectively expandable portion being outside the distal end of the catheter.

10. Apparatus of claim 1 wherein the cutting element comprises a wire.

11. Apparatus of claim 10 wherein the wire comprises an electrocautery element.

12. Apparatus of claim 10 wherein the wire is rotary driven.

13. Apparatus of claim 10 wherein the wire is reciprocally driven.

14. Apparatus of claim 10 wherein the wire comprises a rough surface.

15. Apparatus for resecting a diseased heart valve of a heart, the apparatus comprising:

an elongate member to allow the apparatus to be positioned in the heart, the elongate member having a longitudinal axis and a distal end;

a selectively expandable portion having a proximal end and a distal end, wherein the selectively expandable portion is positioned at the distal end of the elongate member, the selectively expandable portion defines a longitudinal axis from the proximal end to the distal end and is selectively expandable from a first position having a given width in a perpendicular direction to the longitudinal axis to a second position having a larger width in the perpendicular direction to the longitudinal axis; and at least one cutting element, for cutting the diseased heart valve, disposed on the elongate member within the selectively expandable portion, wherein the at least one cutting element is moved from the first position to the second position by the selectively expandable portion, and wherein the selectively expandable portion comprises at least three expandable arms and the at least one cutting element is disposed on at least one of the at least three expandable arms, wherein at least one of the at least three expandable arms having the cutting element disposed thereon defines a window recess therein having a given depth from an outer surface, and further wherein the cutting element is disposed in the window recess.

16. Apparatus for resecting a diseased heart valve of a heart, the apparatus comprising:

an elongate member to allow the apparatus to be positioned in the heart, the elongate member having a distal end;

a selectively expandable portion having a proximal end and a distal end, wherein the selectively expandable portion is positioned at the distal end of the elongate member, the selectively expandable portion defines a longitudinal axis from the proximal end to the distal end and is selectively expandable from a first position having a given width in a perpendicular direction to the longitudinal axis to a second position having a larger width in the perpendicular direction to the longitudinal axis; and at least one cutting element, for cutting the diseased heart valve, disposed on the elongate member wherein the at least one cutting element is moved from the first position to the second position by the selectively expandable portion;

wherein the selectively expandable portion comprises at least three expandable arms and the at least one cutting element is disposed on at least one of the at least three expandable arms, wherein at least one of the at least three expandable arms having the cutting element disposed thereon defines a window recess therein having a given depth from an outer surface, and further wherein the cutting element is disposed in the window recess, and wherein the elongate member comprises a catheter and the first position is with the selectively expandable portion being inside the distal end of the catheter and the second position is with the selectively expandable portion being outside the distal end of the catheter.

* * * * *